(12) United States Patent
Lu et al.

(10) Patent No.: US 10,759,787 B2
(45) Date of Patent: Sep. 1, 2020

(54) BENZOFURAN DERIVATIVE, PREPARATION METHOD THEREOF AND USE THEREOF IN MEDICINE

(71) Applicants: Jiangsu Hengrui Medicine Co., Ltd., Lianyungang, Jiangsu (CN); Shanghai Hengrui Pharmaceutical Co., Ltd., Shanghai (CN)

(72) Inventors: Biao Lu, Shanghai (CN); Xiaodong Shen, Shanghai (CN); Mingxun He, Shanghai (CN); Dong Liu, Shanghai (CN); Minsheng Zhang, Shanghai (CN)

(73) Assignees: Jiangsu Hengrui Medicine Co., Ltd., Lianyungang, Jiangsu (CN); Shanghai Hengrui Pharmaceutical Co., Ltd., Shanghai (CN)

( * ) Notice: Subject to any disclaimer, the term of this patent is extended or adjusted under 35 U.S.C. 154(b) by 0 days.

(21) Appl. No.: 15/775,958

(22) PCT Filed: Nov. 2, 2016

(86) PCT No.: PCT/CN2016/104318
§ 371 (c)(1),
(2) Date: May 14, 2018

(87) PCT Pub. No.: WO2017/084494
PCT Pub. Date: May 26, 2017

(65) Prior Publication Data
US 2018/0327394 A1 Nov. 15, 2018

(30) Foreign Application Priority Data

Nov. 19, 2015 (CN) .......................... 2015 1 0800975

(51) Int. Cl.
| | |
|---|---|
| *A61K 31/4433* | (2006.01) |
| *A61K 31/4545* | (2006.01) |
| *A61K 31/496* | (2006.01) |
| *A61K 31/5377* | (2006.01) |
| *A61P 35/00* | (2006.01) |
| *C07D 405/12* | (2006.01) |
| *C07D 405/14* | (2006.01) |
| *C07D 409/14* | (2006.01) |

(52) U.S. Cl.
CPC ........ *C07D 405/14* (2013.01); *A61K 31/4433* (2013.01); *A61K 31/4545* (2013.01); *A61K 31/496* (2013.01); *A61K 31/5377* (2013.01); *A61P 35/00* (2018.01); *C07D 405/12* (2013.01); *C07D 409/14* (2013.01)

(58) Field of Classification Search
CPC .. C07D 405/14; C07D 409/14; C07D 405/12; A61K 31/5377; A61K 31/4433; A61K 31/4545; A61K 31/496; A61P 35/00
See application file for complete search history.

(56) References Cited

U.S. PATENT DOCUMENTS 9,730,925 B2   8/2017 Creasy et al.

FOREIGN PATENT DOCUMENTS

| CN | 103987842 A | 8/2014 |
| WO | 2011140325 A1 | 11/2011 |

(Continued)

OTHER PUBLICATIONS

Schafer, S., Kolkhof, P. Failure is an option: learning from unsuccessful proof-of-concept trials. Drug Discovery Today. Nov. 2008, 13, 913-916.*

(Continued)

*Primary Examiner* — Amanda L. Aguirre

(74) *Attorney, Agent, or Firm* — Weihong Hsing; Ming He; Ice Miller LLP

(57) ABSTRACT

The present invention relates to a benzofuran derivative, a preparation method thereof and a use thereof in medicine. In particular, the present invention relates to the benzofuran derivative as shown by general formula (I), the preparation method thereof, a pharmaceutical composition containing the derivative, and uses thereof as an EZH2 inhibitor and in the prevention and/or treatment of diseases such as tumours and cancers, etc., and in particular, uses thereof in the prevention and/or treatment of non-Hodgkin's lymphoma, diffuse large B-cell lymphoma, follicular lymphoma and synovial sarcoma, wherein the definitions of the substituents in the general formula (I) are the same as those defined in the description.

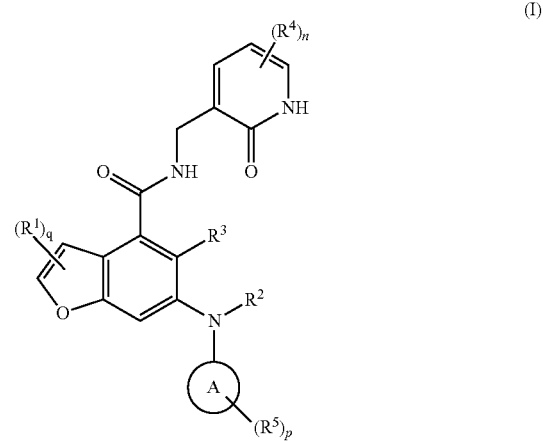

(I)

23 Claims, No Drawings

(56) References Cited

FOREIGN PATENT DOCUMENTS

| WO | 2012005805 A1 | 1/2012 |
|----|---------------|--------|
| WO | 2012050532 A1 | 4/2012 |
| WO | 2012061602 A1 | 5/2012 |
| WO | 2012118812 A2 | 9/2012 |
| WO | 2012142504 A1 | 10/2012 |
| WO | 2012142513 A1 | 10/2012 |
| WO | 2013039988 A1 | 3/2013 |
| WO | 2013049770 A2 | 4/2013 |
| WO | 2013067300 A1 | 5/2013 |
| WO | 2013173441 A2 | 11/2013 |
| WO | 2014097041 A1 | 6/2014 |
| WO | 2014177982 A1 | 11/2014 |
| WO | 2015141616 A1 | 9/2015 |

OTHER PUBLICATIONS

Honig, H., Pullman, W. From bench to clinic and back: Perspective on the 1st IQPC Translational Research conference. Journal of Translational Medicine. Dec. 2004, 2, 44.*

Lue et al., Emerging EZH2 inhibitors and Their Application in Lymphoma. Current Hematologic Malignancy Reports, 2018, 13, 369-382.*

Anandan et al., "1-(1-Acetyl-piperidin-4-yl)-3-adamantan-1-yl-urea (AR9281) as a potent, selective, and orally available soluble epoxide hydrolase inhibitor with efficacy in rodent models of hypertension and dysglycemia," Bioorganic & Medicinal Chemistry Letters, vol. 21, pp. 983-988 (2011).

Arbuckle et al., "Optimisation of Pharmacokinetic Properties to Afford an Orally Bioavailable and Selective V1A Receptor Antagonist," Bioorganic & Medicinal Chemistry Letters, vol. 21, pp. 4622-4628 (2011).

Hewings et al., "Optimization of 3,5-Dimethylisoxazole Derivatives as Potent Bromodomain Ligands," Journal of Medicinal Chemistry, vol. 56, pp. 3217-3227 (2013).

International Search Report dated Jan. 22, 2017 in International Application No. PCT/CN2016/104318.

Schultz et al., "Asymmetric Syntheses of 1,6-Dialkyl-1,4-cyclohexadiene Derivatives," Journal of American Chemical Society, vol. 113, No. 13, pp. 4931-4936 (1991).

Chang et al., "The Role of EZH2 in Tumour Progression," British Journal of Cancer, vol. 106, No. 2, pp. 243-247 (2012).

Lund et al., "EZH2 in Normal and Malignant Hematopoiesis," Leukemia, vol. 28, No. 1, pp. 44-49 (2014).

Shen et al., "Update of Research on the Role of EZH2 in Cancer Progression," OncoTargets and Therapy, vol. 6, pp. 321-324 (2013).

Yan et al., "EZH2 Overexpression in Natural Killer/T-cell Lymphoma Confers Growth Advantage Independently of Histone Methyltransferase Activity," Blood, vol. 121, pp. 4512-4520 (2013).

* cited by examiner

BENZOFURAN DERIVATIVE, PREPARATION METHOD THEREOF AND USE THEREOF IN MEDICINE

CROSS-REFERENCE TO RELATED APPLICATION

This application is a Section 371 of International Application No. PCT/CN2016/104318, filed Nov. 2, 2016, which was published in the Chinese language on May 26, 2017, under International Publication No. WO 2017/084494 A1, which claims priority under 35 U.S.C. § 119(b) to Chinese Application No. 201510800975.7, filed Nov. 19, 2015.

FIELD OF THE INVENTION

The present invention belongs to the filed of medicine and relates to a benzofuran derivative, a preparation method thereof and a use thereof in the medical research. The present invention discloses the use of the devivative as an EZH2 inhibitor in the prevention and/or treatment of diseases such as tumours and cancers, etc., in particular, in the prevention and/or treatment of non-Hodgkin's lymphoma, diffuse large B-cell lymphoma, follicular lymphoma and synovial sarcoma, etc.

BACKGROUND OF THE INVENTION

The occurrence of tumor is an evolution process of multi-factors and multi-stages, involving mutation and epigenetic changes of multiple genes such as oncogene, antioncogene and DNA damage repair gene. Strictly speaking, epigenetics is defined as a combination of genetic mechanisms capable of altering genome function in addition to the direct alteration of the DNA sequence. Herein, "epigenetics" refers broadly to elements of chromatin structure that control genome function, regardless of whether the control is heritable. Epigenetic or chromatin-based regulation plays an important role in gene expression in normal physiological function or in cancer evolution Polycomb group protein (PcG) is an important protein factor involved in the negative regulation of chromatin gene epigenetics. In mammals, PcG is mainly divided into two types with different structures and functions: polycomb repressive complex 2 (PRC2) and polycomb repressive complex 1 (PRC1). The histone methyltransferase encoded by the EZH2 gene is the catalytic component of polycomb repressive complex 2 (PRC2) and exerts the trimethyltransferase activity on the lysine 27 (H3K27) of histone H3 to generate H3K27me3 by means of the SET domain of the EZH2 subunit. It promotes transcriptional repression by means of various mechanisms including the urgent recruitment of DNA methyltransferases (DNMT) and PRC1 that ubiquitinates H2AK119. The codon mutation at codon 641 of EZH2, the most common mutation hotspot, is a gain-of-function mutation leading to an enhanced trimethylation of histone H3K27, and plays an important role in the tumorigenesis of GCB-type diffuse large B-cell lymphoma (DLBCL) and follicular lymphoma (FL). Recurrent somatic mutations in the SET domain of EZH2 are common in patients with diffused large B cell lymphomas (DLBCL). In addition, EZH2 overexpression is common in a variety of tumor types with poor prognosis, including cancers, lymphomas and soft tissue sarcomas etc. EZH2 expression in synovial sarcoma is associated with high H3K27 trimethylation. EZH2 levels are abnormally elevated in cancer tissues compared to normal tissues, and EZH2 is most highly expressed in advanced cancers or poor prognosis. In some types of cancers, EZH2 overexpression occurs simultaneously with amplification of the EZH2 gene. A large number of si/shRNA experimental studies show that reduction of EZH2 expression in tumor cell lines can inhibit tumor cell proliferation, migration, and invasion, or angiogenesis, and lead to apoptosis.

Patent applications disclosing EZH2 selective inhibitors include WO2012005805, WO2012050532, WO2012118812, WO2012142513, WO2012142504, WO2013049770, WO2013039988, WO2013067300, WO2015141616, and WO2011140325, etc.

EZH2 inhibitors as drugs have promising application prospects in the medical industry. However, there is still a need to develop new EZH2 inhibitors for achieving better therapeutic effects in tumors and cancers, and which better meets the maket demand.

SUMMARY OF THE INVENTION

The present invention is directed to a compound of formula (I) or a tautomer, mesomer, racemate, enantiomer, diastereomer, or mixture thereof, or a pharmaceutically acceptable salt thereof, wherein the structure of the compound of formula (I) is as follows:

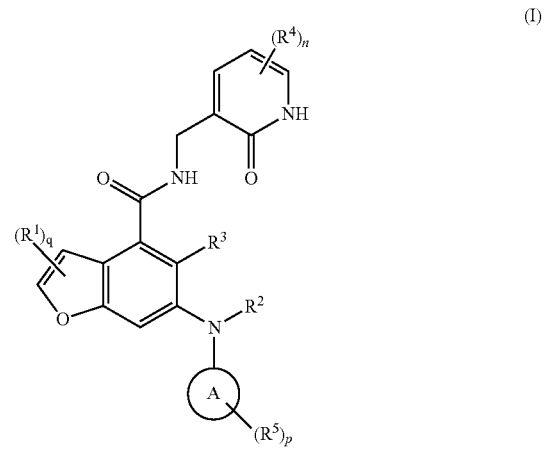

(I)

wherein:

ring A is selected from the group consisting of heterocyclyl and cycloalkyl;

each $R^1$ is identical or different and each is independently selected from the group consisting of hydrogen, halogen, alkyl, haloalkyl, alkoxy, haloalkoxy, amino, nitro, hydroxy, cyano, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$(CH_2)_xR^a$, wherein the alkyl, haloalkyl, heterocyclyl, aryl and heteroaryl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^a$ is selected from the group consisting of halogen, cycloalkyl, heterocyclyl and —$NR^7R^8$, wherein the cycloalkyl and heterocyclyl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl, and heteroaryl;

R² is hydrogen or alkyl, wherein the alkyl is optionally substituted by one or more groups selected from the group consisting of halogen, hydroxy, cyano, cycloalkyl and heterocyclyl;

R³ is selected from the group consisting of hydrogen, alkyl, halogen, cyano, alkoxy and haloalkyl;

each R⁴ is identical or different and each is independently selected from the group consisting of hydrogen, alkyl, haloalkyl, hydroxy, amino, alkoxy, haloalkoxy, cycloalkyl, heterocyclyl, aryl, heteroaryl, —OR⁶, —C(O)R⁶, —C(O)OR⁶, —S(O)$_m$R⁶, —S(O)$_m$NR⁷R⁸ and —NR⁷R⁸;

each R⁵ is identical or different and each is independently selected from the group consisting of hydrogen, alkyl, oxo, halogen, haloalkyl, hydroxy, amino, alkoxy, haloalkoxy, cycloalkyl, heterocyclyl, aryl, heteroaryl, —OR⁶, —C(O)R⁶, —C(O)OR⁶, —S(O)$_m$R⁶, —S(O)$_m$NR⁷R⁸ and —NR⁷R⁸;

R⁶ is selected from the group consisting of hydrogen, alkyl, haloalkyl, alkoxy, hydroxyalkyl, hydroxy, amino, cycloalkyl, heterocyclyl, aryl and heteroaryl;

R⁷ and R⁸ are identical or different and each is independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, amino, cycloalkyl, heterocyclyl, aryl and heteroaryl are each independently and optionally substituted by one or more groups selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

m is 0, 1 or 2;
n is 0, 1, 2 or 3;
p is 0, 1, 2, 3, 4 or 5;
q is 0, 1 or 2; and
x is 0, 1, 2 or 3.

In a preferred embodiment of the present invention, in a compound of formula (I) or a tautomer, mesomer, racemate, enantiomer, diastereomer, or mixture thereof, or a pharmaceutically acceptable salt thereof, n is 2.

In a preferred embodiment of the present invention, in a compound of formula (I) or a tautomer, mesomer, racemate, enantiomer, diastereomer, or mixture thereof, or a pharmaceutically acceptable salt thereof, q is 0 or 1.

In a preferred embodiment of the present invention, in a compound of formula (I) or a tautomer, mesomer, racemate, enantiomer, diastereomer, or mixture thereof, or a pharmaceutically acceptable salt thereof, p is 0 or 1.

In a preferred embodiment of the present invention, in a compound of formula (I) or a tautomer, mesomer, racemate, enantiomer, diastereomer, or mixture thereof, or a pharmaceutically acceptable salt thereof, each R¹ is identical or different and each is independently selected from the group consisting of hydrogen, halogen, alkyl, haloalkyl, cyano, cycloalkyl, heterocyclyl and —(CH₂)$_x$R$^a$, wherein the alkyl and heterocyclyl are each independently and optionally substituted by one or more groups selected from the group consisting of alkyl, hydroxyalkyl and halogen; and R$^a$ is selected from the group consisting of halogen, cycloalkyl, heterocyclyl and —NR⁷R⁸, wherein the cycloalkyl and heterocyclyl are each independently and optionally substituted by one or more groups selected from the group consisting of hydroxyalkyl, alkyl and halogen; and R⁷, R⁸ and x are as defined in formula (I).

In a preferred embodiment of the present invention, in a compound of formula (I) or a tautomer, mesomer, racemate, enantiomer, diastereomer, or mixture thereof, or a pharmaceutically acceptable salt thereof, each R¹ is identical or different and each is independently selected from the group consisting of hydrogen, alkyl, haloalkyl, cyano and —(CH₂)$_x$R$^a$, wherein x is 0, and R$^a$ is halogen or cycloalkyl.

In a preferred embodiment of the present invention, in a compound of formula (I) or a tautomer, mesomer, racemate, enantiomer, diastereomer, or mixture thereof, or a pharmaceutically acceptable salt thereof, R² is alkyl optionally substituted by cycloalkyl.

In a preferred embodiment of the present invention, in a compound of formula (I) or a tautomer, mesomer, racemate, enantiomer, diastereomer, or mixture thereof, or a pharmaceutically acceptable salt thereof, R³ is selected from the group consisting of alkyl, halogen and haloalkyl.

In a preferred embodiment of the present invention, in a compound of formula (I) or a tautomer, mesomer, racemate, enantiomer, diastereomer, or mixture thereof, or a pharmaceutically acceptable salt thereof, each R⁴ is identical or different and each is independently selected from the group consisting of hydrogen, alkyl and alkoxy.

In a preferred embodiment of the present invention, in a compound of formula (I), or a tautomer, mesomer, racemate, enantiomer, diastereomer, or mixture thereof, or a pharmaceutically acceptable salt thereof, each R⁵ is identical or different and each is independently selected from the group consisting of hydrogen, halogen, oxo, haloalkyl, —C(O)R⁶, —S(O)$_m$R⁶ and —NR⁷R⁸, wherein R⁶ to R⁸ and m are as defined in formula (I), preferably hydrogen.

In a preferred embodiment of the present invention, a compound of formula (I) or a tautomer, mesomer, racemate, enantiomer, diastereomer, or mixture thereof, or a pharmaceutically acceptable salt thereof, is a compound of formula (II) or a tautomer, mesomer, racemate, enantiomer, diastereomer, or mixture thereof, or a pharmaceutically acceptable salt thereof:

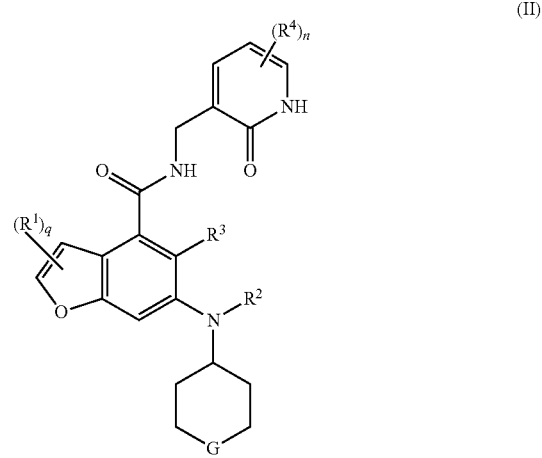

wherein:

G is selected from the group consisting of CR$^b$R$^c$, C=O, S(O)$_m$, NR$^d$ and oxygen; R$^b$ and R$^c$ are each independently selected from the group consisting of hydrogen, alkyl, alkoxy, halogen, amino, nitro, hydroxy, cyano, cycloalkyl, heterocyclyl, aryl, heteroaryl, —OR⁶, —C(O)R⁶, —C(O)OR⁶, —S(O)$_m$R⁶ and —NR⁷R⁸;

R$^d$ is selected from the group consisting of hydrogen, alkyl, cycloalkyl, haloalkyl, hydroxyalkyl, heterocyclyl, aryl, heteroaryl, —C(O)R⁶, —C(O)OR⁶ and —S(O)$_m$R⁶; and $R^1$ to $R^4$, $R^6$ to $R^8$, n, m and q are as defined in formula (I).

In a preferred embodiment of the present invention, a compound of formula (II) or a tautomer, mesomer, racemate, enantiomer, diastereomer, or mixture thereof, or a pharmaceutically acceptable salt thereof, is a compound of formula (III), or a tautomer, mesomer, racemate, enantiomer, diastereomer, or mixture thereof, or a pharmaceutically acceptable salt thereof:

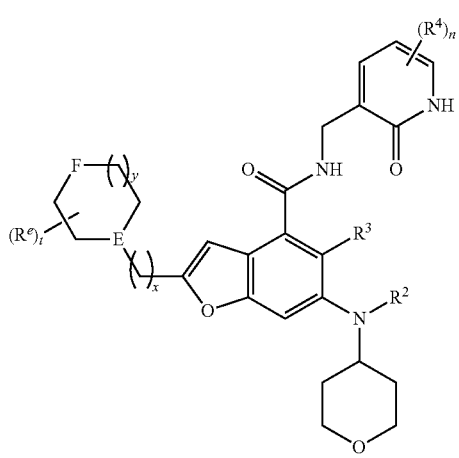

(III)

wherein:

E is CH or nitrogen;

F is selected from the group consisting of $CR^bR^c$, C=O, $NR^d$ and oxygen;

$R^b$ and $R^c$ are each independently selected from the group consisting of hydrogen, alkyl, alkoxy, halogen, amino, nitro, hydroxy, cyano, cycloalkyl, heterocyclyl, aryl, heteroaryl, —$OR^6$, —$C(O)R^6$, —$C(O)OR^6$, —$S(O)_mR^6$ and —$NR^7R^8$;

$R^d$ is selected from the group consisting of hydrogen, alkyl, cycloalkyl, haloalkyl, hydroxyalkyl, heterocyclyl, aryl, heteroaryl, —$C(O)R^6$, —$C(O)OR^6$ and —$S(O)_mR^6$;

each $R^e$ is identical or different and each is independently selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl;

t is 0, 1, 2, 3, 4 or 5;

x is 0, 1, 2 or 3;

y is 0, 1, 2 or 3; and $R^1$ to $R^4$, $R^6$ to $R^8$, m and n are as defined in formula (I).

In a preferred embodiment of the present invention, a compound of formula (III) or a tautomer, mesomer, racemate, enantiomer, diastereomer, or mixture thereof, or a pharmaceutically acceptable salt thereof, is a compound of formula (IV), or a tautomer, mesomer, racemate, enantiomer, diastereomer, or mixture thereof, or a pharmaceutically acceptable salt thereof:

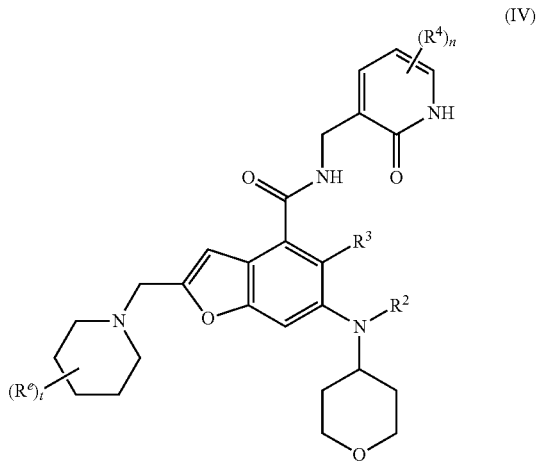

(IV)

wherein:

each $R^e$ is identical or different and is independently selected from the group consisting of hydrogen, alkyl and halogen;

t is 0, 1, 2, 3, 4 or 5; and $R^2$ to $R^4$ and n are as defined in formula (I).

In a preferred embodiment of the present invention, a compound of formula (III) or a tautomer, mesomer, racemate, enantiomer, diastereomer, or mixture thereof, or a pharmaceutically acceptable salt thereof, is a compound of formula (V), or a tautomer, mesomer, racemate, enantiomer, diastereomer, or mixture thereof, or a pharmaceutically acceptable salt thereof:

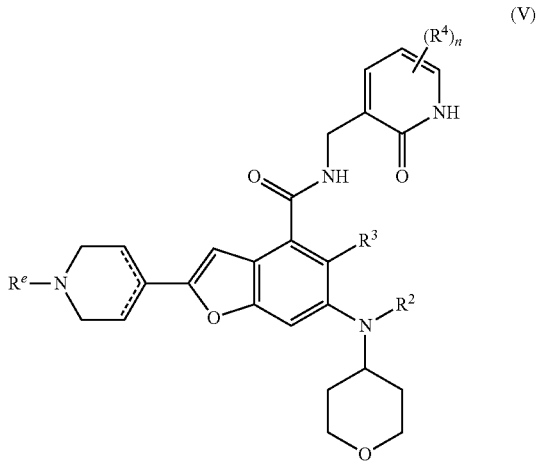

(V)

wherein:

$R^e$ is selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl; and $R^2$ to $R^4$ and n are as defined in formula (I).

Typical compounds of formula (I) or a tautomer, mesomer, racemate, enantiomer, diastereomer, or mixture thereof, or a pharmaceutically acceptable salt thereof, include, but are not limited to:

| Example No. | Structure and Name |
|---|---|
| 1 | 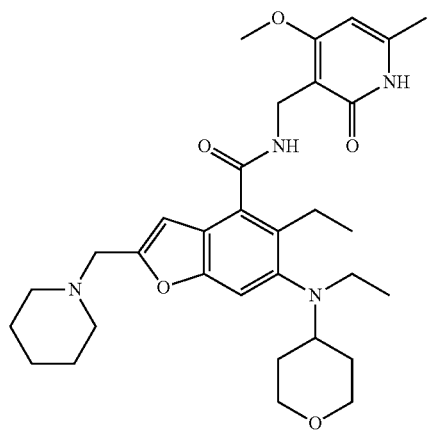<br>5-ethyl-6-(ethyl(tetrahydro-2H-pyran-4-yl)amino)-N-((4-methoxy-6-methyl-2-oxo-1,2-dihydropyridin-3-yl)methyl)-2-(piperidin-1-ylmethyl)benzofuran-4-carboxamide |
| 2 | 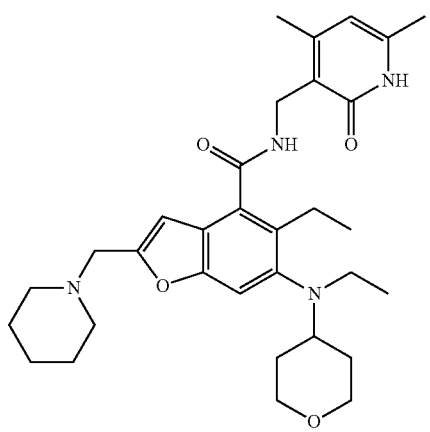<br>N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide |
| 3 | 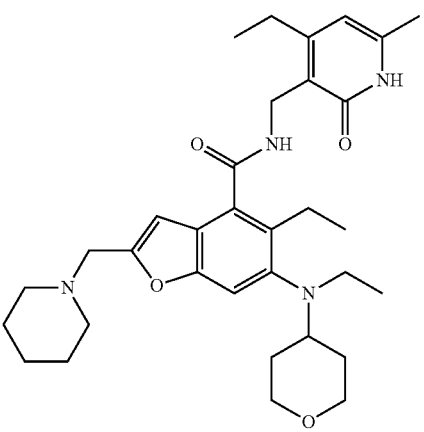<br>5-ethyl-6-(ethyl(tetrahydro-2H-pyran-4-yl)amino)-N-((4-ethyl-6-methyl-2-oxo-1,2-dihydropyridin-3-yl)methyl)-2-(piperidin-1-ylmethyl)benzofuran-4-carboxamide |
| 4 | 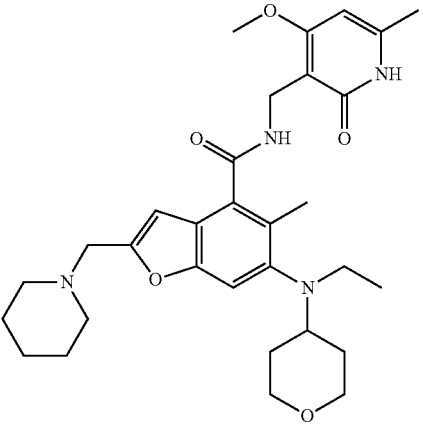<br>6-(ethyl(tetrahydro-2H-pyran-4-yl)amino)-N-((4-methoxy-6-methyl-2-oxo-1,2-dihydropyridin-3-yl)methyl)-5-methyl-2-(piperidin-1-ylmethyl)benzofuran-4-carboxamide |

| Example No. | Structure and Name |
|---|---|
| 5 | 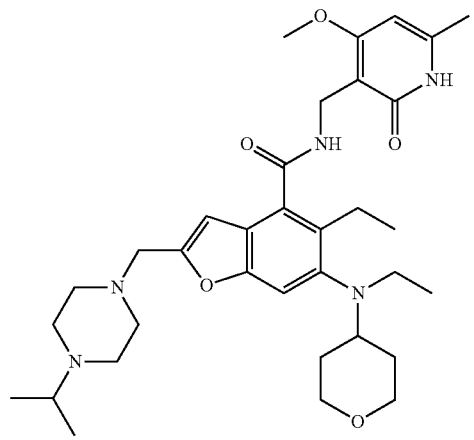

5-ethyl-6-(ethyl(tetrahydro-2H-pyran-4-yl)amino)-2-((4-isopropylpiperazin-1-yl)methyl)-N-((4-methoxy-6-methyl-2-oxo-1,2-dihydropyridin-3-yl)methyl)benzofuran-4-carboxamide |
| 6 | 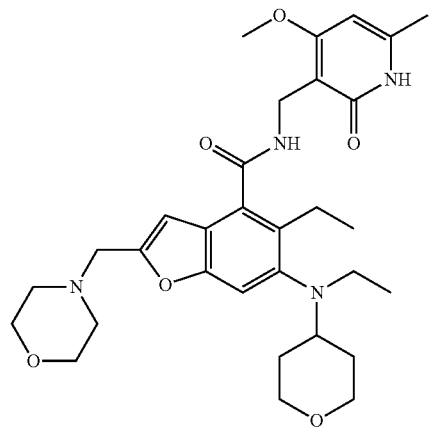

5-ethyl-6-(ethyl(tetrahydro-2H-pyran-4-yl)amino)-N-((4-methoxy-6-methyl-2-oxo-1,2-dihydropyridin-3-yl)methyl)-2-(morpholinomethyl)benzofuran-4-carboxamide |
| 7 | 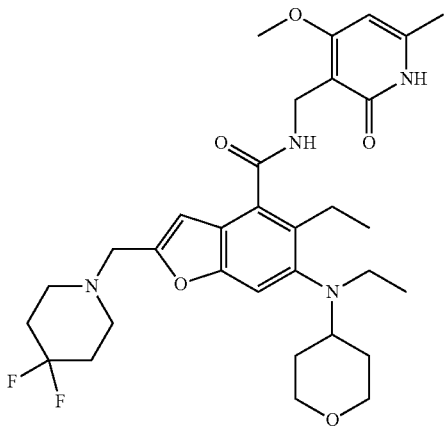

2-((4,4-difluoropiperidin-1-yl)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide |
| 8 | 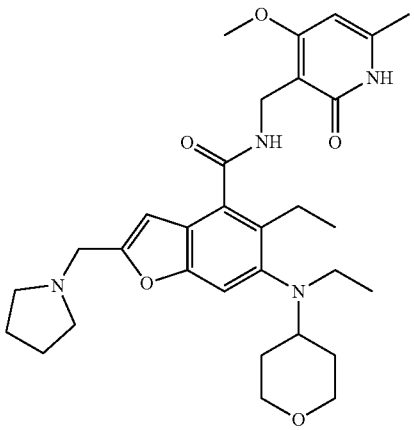

5-ethyl-6-(ethyl(tetrahydro-2H-pyran-4-yl)amino)-N-((4-methoxy-6-methyl-2-oxo-1,2-dihydropyridin-3-yl)methyl)-2-(pyrrolidin-1-ylmethyl)benzofuran-4-carboxamide |

| Example No. | Structure and Name |
|---|---|
| 9 | 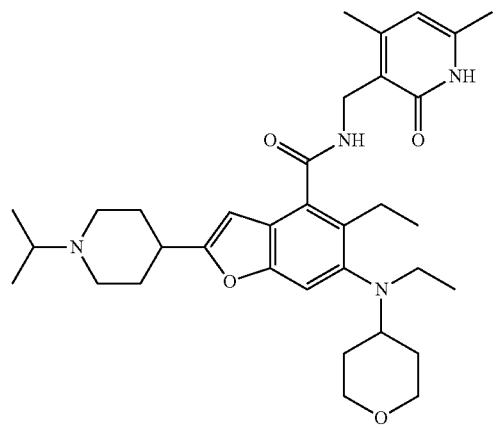<br>9<br>N-((4,6-dimethyl-2-oxo-1,2-dihydropyridin-3-yl)methyl)-5-ethyl-6-(ethyl(tetrahydro-2H-pyran-4-yl)amino)-2-(1-isopropyl-piperidin-4-yl)benzofuran-4-carboxamide |
| 10 | 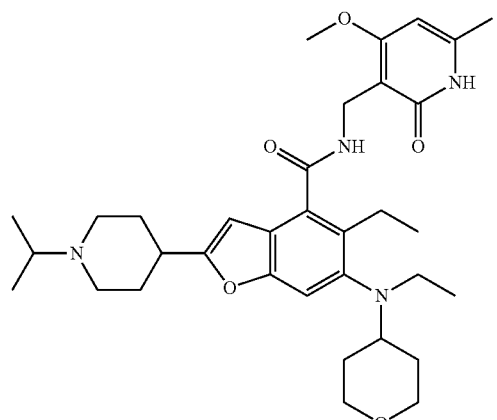<br>10<br>5-ethyl-6-(ethyl(tetrahydro-2H-pyran-4-yl)amino)-2-(1-isopropylpiperidin-4-yl)-N-((4-methoxy-6-methyl-2-oxo-1,2-dihydropyridin-3-yl)methyl)benzofuran-4-carboxamide |
| 11 | 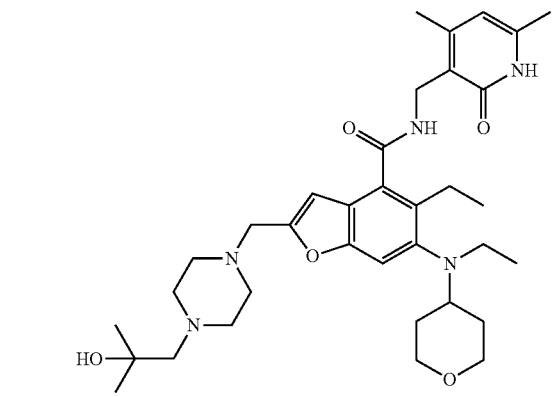<br>11<br>N-((4,6-dimethyl-2-oxo-1,2-dihydropyridin-3-yl)methyl)-5-ethyl-6-(ethyl(tetrahydro-2H-pyran-4-yl)amino)-2-((4-(2-hydroxy-2-methylpropyl)piperazin-1-yl)methyl)benzofuran-4-carboxamide |
| 12 | 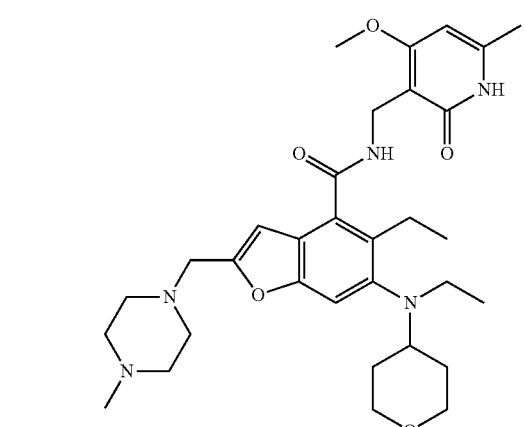<br>12<br>5-ethyl-6-(ethyl(tetrahydro-2H-pyran-4-yl)amino)-N-((4-methoxy-6-methyl-2-oxo-1,2-dihydropyridin-3-yl)methyl)-2-((4-methylpiperazin-1-yl)methyl)benzofuran-4-carboxamide |

| Example No. | Structure and Name |
|---|---|
| 13 | 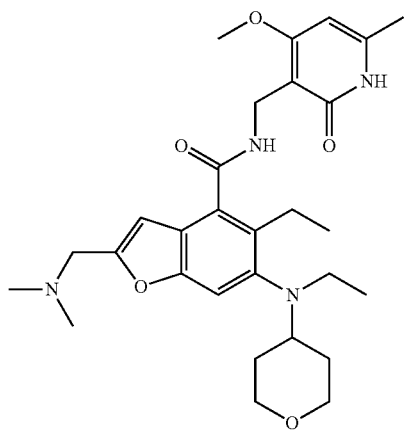<br>13<br>2-((dimethylamino)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide |
| 14 | 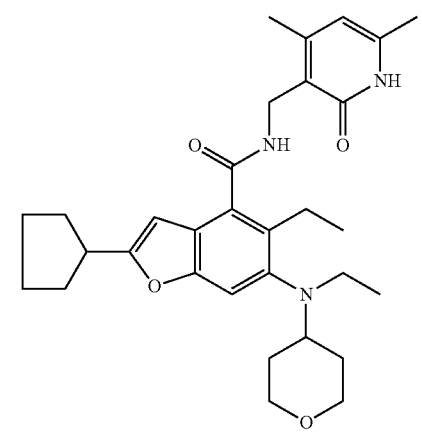<br>14<br>2-cyclopentyl-N-((4,6-dimethyl-2-oxo-1,2-dihydropyridin-3-yl)methyl)-5-ethyl-6-(ethyl(tetrahydro-2H-pyran-4-yl)amino)benzofuran-4-carboxamide |
| 15 | 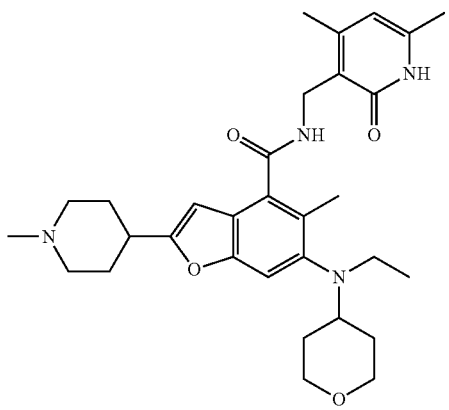<br>15<br>N-((4,6-dimethyl-2-oxo-1,2-dihydropyridin-3-yl)methyl)-6-(ethyl(tetrahydro-2H-pyran-4-yl)amino)-5-methyl-2-(1-methylpiperidin-4-yl)benzofuran-4-carboxamide |
| 16 | 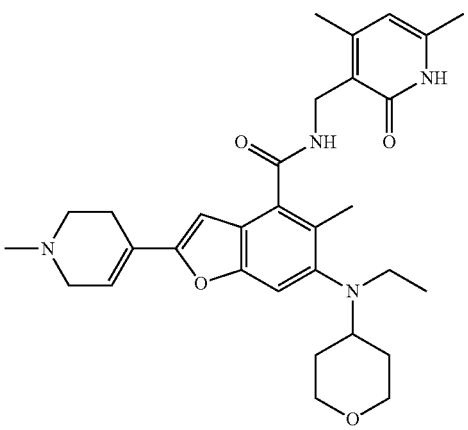<br>16<br>N-((4,6-dimethyl-2-oxo-1,2-dihydropyridin-3-yl)methyl)-6-(ethyl(tetrahydro-2H-pyran-4-yl)amino)-5-methyl-2-(1-methyl-1,2,3,6-tetrahydropyridin-4-yl)benzofuran-4-carboxamide |

| Example No. | Structure and Name |
|---|---|
| 17 | 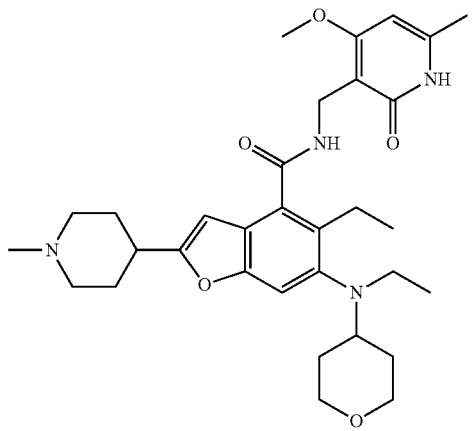

5-ethyl-6-(ethyl(tetrahydro-2H-pyran-4-yl)amino)-N-((4-methoxy-6-methyl-2-oxo-1,2-dihydropyridin-3-yl)methyl)-2-(1-methylpiperidin-4-yl)benzofuran-4-carboxamide |
| 18 | 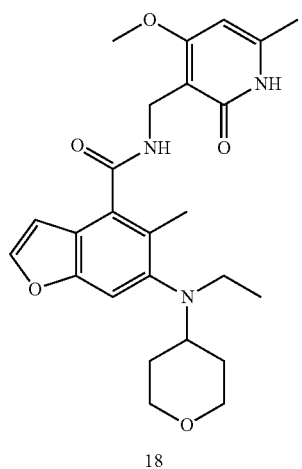

6-(ethyl(tetrahydro-2H-pyran-4-yl)amino)-N-((4-methoxy-6-methyl-2-oxo-1,2-dihydropyridin-3-yl)methyl)-5-methylbenzofuran-4-carboxamide |
| 19 | 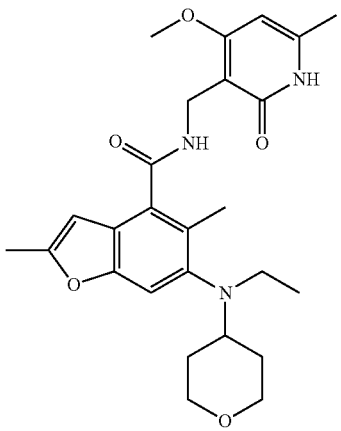

6-(ethyl(tetrahydro-2H-pyran-4-yl)amino)-N-((4-methoxy-6-methyl-2-oxo-1,2-dihydropyridin-3-yl)methyl)-2,5-dimethylbenzofuran-4-carboxamide |
| 20 | 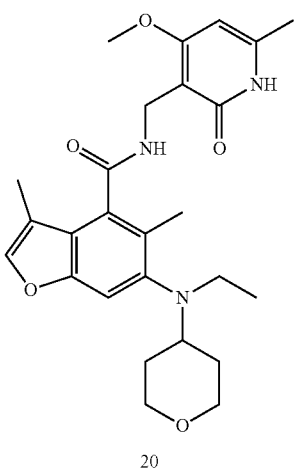

6-(ethyl(tetrahydro-2H-pyran-4-yl)amino)-N-((4-methoxy-6-methyl-2-oxo-1,2-dihydropyridin-3-yl)methyl)-3,5-dimethylbenzofuran-4-carboxamide |

| Example No. | Structure and Name |
|---|---|
| 21 | 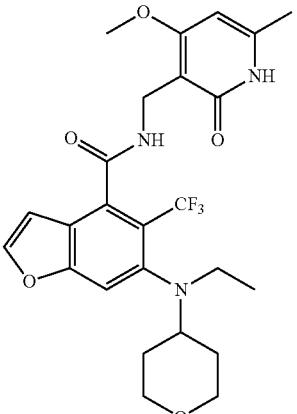<br>6-(ethyl(tetrahydro-2H-pyran-4-yl)amino)-N-((4-methoxy-6-methyl-2-oxo-1,2-dihydropyridin-3-yl)methyl)-5-(trifluoromethyl)benzofuran-4-carboxamide |
| 22 | 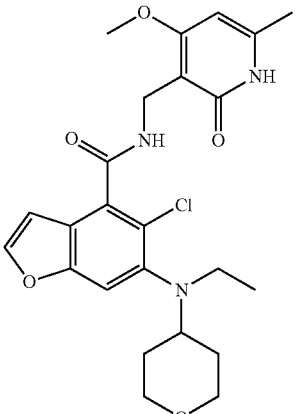<br>5-chloro-6-(ethyl(tetrahydro-2H-pyran-4-yl)amino)-N-((4-methoxy-6-methyl-2-oxo-1,2-dihydropyridin-3-yl)methyl)benzofuran-4-carboxamide |
| 23 | 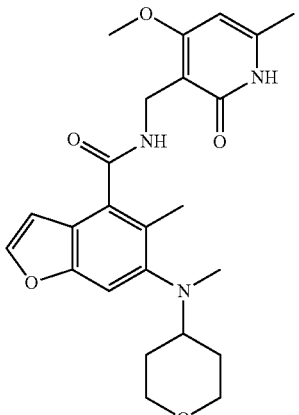<br>N-((4-methoxy-6-methyl-2-oxo-1,2-dihydropyridin-3-yl)methyl)-5-methyl-6-(methyl(tetrahydro-2H-pyran-4-yl)amino)benzofuran-4-carboxamide |
| 24 | 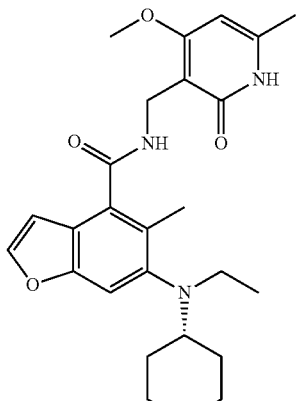<br>6-(((1r,4r)-4-(dimethylamino)cyclohexyl)(ethyl)amino)-N-((4-methoxy-6-methyl-2-oxo-1,2-dihydropyridin-3-yl)methyl)-5-methylbenzofuran-4-carboxamide |

| Example No. | Structure and Name |
|---|---|
| 25 | 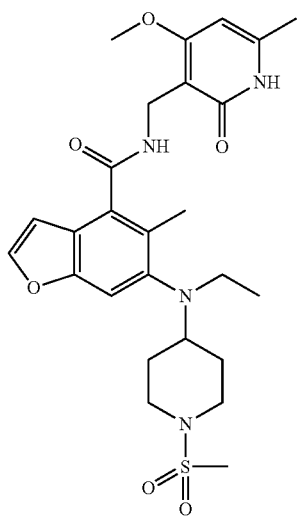<br>25<br>6-(ethyl(1-(methylsulfonyl)piperidin-4-yl)amino)-N-((4-methoxy-6-methyl-2-oxo-1,2-dihydropyridin-3-yl)methyl)-5-methyl-benzofuran-4-carboxamide |
| 26 | 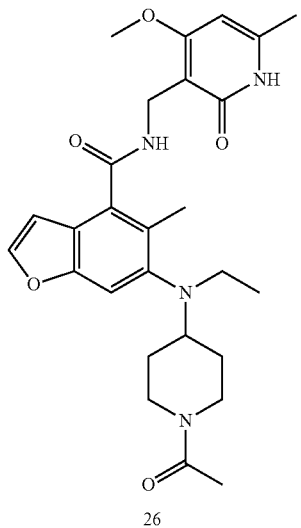<br>26<br>6-((1-acetylpiperidin-4-yl)(ethyl)amino)-N-((4-methoxy-6-methyl-2-oxo-1,2-dihydropyridin-3-yl)methyl)-5-methylbenzofuran-4-carboxamide |
| 27 | 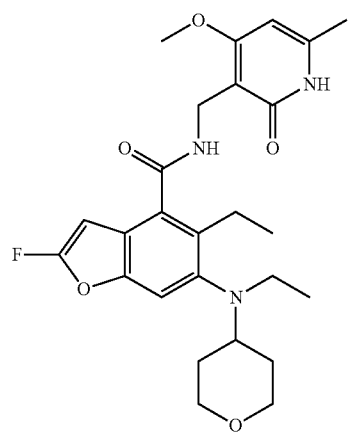<br>27<br>5-ethyl-6-(ethyl(tetrahydro-2H-pyran-4-yl)amino)-2-fluoro-N-((4-methoxy-6-methyl-2-oxo-1,2-dihydropyridin-3-yl)methyl)benzofuran-4-carboxamide |
| 28 | 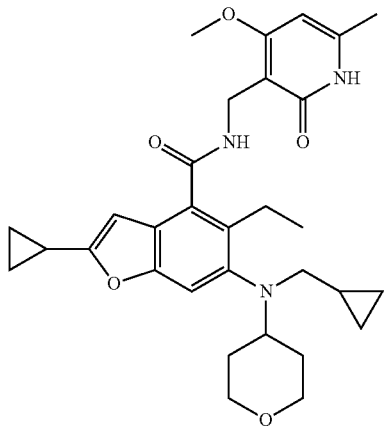<br>28<br>2-cyclopropyl-6-((cyclopropylmethyl)(tetrahydro-2H-pyran-4-yl)amino)-5-ethyl-N-((4-methoxy-6-methyl-2-oxo-1,2-dihydro-pyridin-3-yl)methyl)benzofuran-4-carboxamide |

| Example No. | Structure and Name |
|---|---|
| 29 | 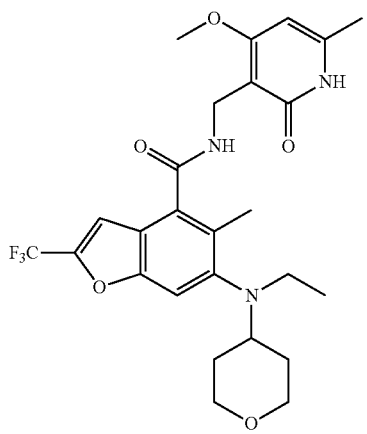

29

6-(ethyl(tetrahydro-2H-pyran-4-yl)amino)-N-((4-methoxy-6-methyl-2-oxo-1,2-dihydropyridin-3-yl)methyl)-5-methyl-2-(trifluoromethyl)benzofuran-4-carboxamide |
| 30 | 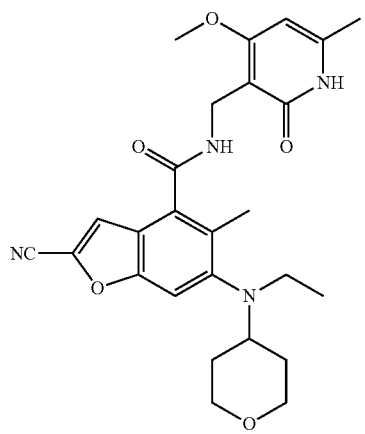

30

2-cyano-6-(ethyl(tetrahydro-2H-pyran-4-yl)amino)-N-((4-methoxy-6-methyl-2-oxo-1,2-dihydropyridin-3-yl)methyl)-5-methylbenzofuran-4-carboxamide |

| Example No. | Structure and Name |
|---|---|
| 31 | 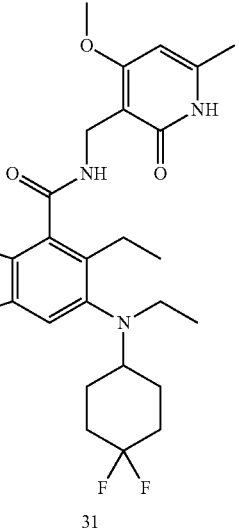

31

6-((4,4-difluorocyclohexyl)(ethyl)amino)-5-ethyl-N-((4-methoxy-6-methyl-2-oxo-1,2-dihydropyridin-3-yl)methyl)benzofuran-4-carboxamide |
| 32 | 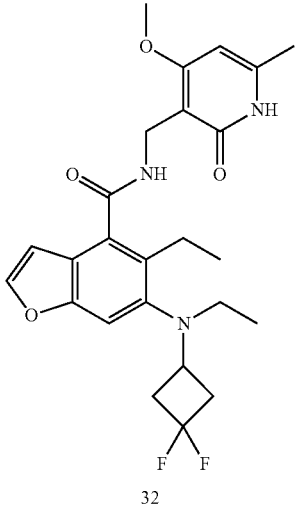

32

6-((3,3-difluorocyclobutyl)(ethyl)amino)-5-ethyl-N-((4-methoxy-6-methyl-2-oxo-1,2-dihydropyridin-3-yl)methyl)benzofuran-4-carboxamide |

-continued

| Example No. | Structure and Name |
|---|---|
| 33 | 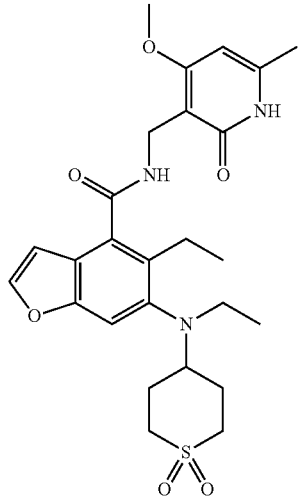

33

6-((1,1-dioxidotetrahydro-2H-thiopyran-4-yl)(ethyl)amino)-5-ethyl-N-((4-methoxy-6-methyl-2-oxo-1,2-dihydropyridin-3-yl)methyl)benzofuran-4-carboxamide |
| 34 | 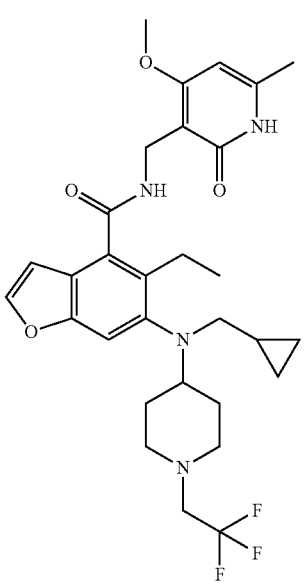

34

6-((cyclopropylmethyl)(1-(2,2,2-trifluoroethyl)piperidin-4-yl)amino)-5-ethyl-N-((4-methoxy-6-methyl-2-oxo-1,2-dihydropyridin-3-yl)methyl)benzofuran-4-carboxamide | or a tautomer, mesomer, racemate, enantiomer, diastereomer, or mixture thereof, or a pharmaceutically acceptable salt thereof.

The present invention further provides an intermediate for preparing the compound of formula (I) or a tautomer, mesomer, racemate, enantiomer, diastereomer, or mixture thereof, or a pharmaceutically acceptable salt thereof, i.e., a compound of formula (VI):

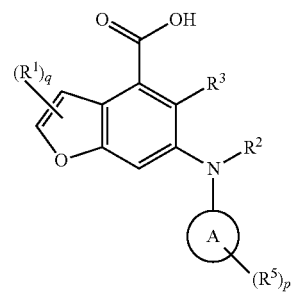

or a tautomer, mesomer, racemate, enantiomer, diastereomer, or mixture thereof, or a pharmaceutically acceptable salt thereof, wherein:

ring A, $R^1$ to $R^3$, $R^5$, p and q are as defined in formula (I).

In another aspect, the present invention is also directed to a process for preparing a compound of formula (I) or a tautomer, mesomer, racemate, enantiomer, diastereomer, or mixture thereof, or a pharmaceutically acceptable salt thereof, comprising:

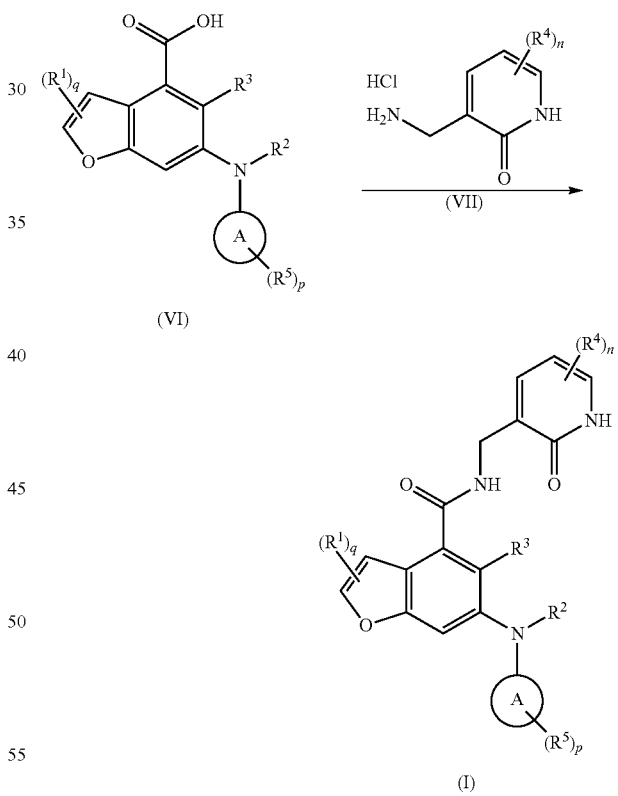

condensing a compound of formula (VI) with a compound of formula (VII) at room temperature to obtain the compound of formula (I);

wherein:

$R^1$ to $R^5$, ring A, p, q and n are as defined in (I).

In another aspect, the present invention is directed to a pharmaceutical composition comprising a therapeutically effective amount of a compound of formula (I), (II), (III), (IV) or (V), or a tautomer, mesomer, racemate, enantiomer, diastereomer, or mixture thereof, or a pharmaceutically acceptable salt thereof, and one or more pharmaceutically acceptable carriers, diluents or excipients. The present invention is also directed to a process for the preparation of the aforementioned composition comprising mixing a compound of formula (I), (II), (III), (IV) or (V) or a tautomer, mesomer, racemate, enantiomer, diastereomer, or mixture thereof, or a pharmaceutically acceptable salt thereof, with one or more pharmaceutically acceptable carriers, diluents or excipients.

The present invention is further directed to use of a compound of formula (I) or a tautomer, mesomer, racemate, enantiomer, diastereomer, or mixture thereof, or a pharmaceutically acceptable salt thereof, or a pharmaceutical composition comprising the same, in the preparation of a medicament for preventing and/or treating tumor and cancer, wherein the cancer is selected from the group consisting of lymphoma, leukemia, breast cancer, lung cancer, prostate cancer, ovarian cancer, liver cancer, melanoma, rhabdomyosarcoma, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck cancer, and myeloma; preferably lymphoma, leukemia, breast cancer, lung cancer, prostate cancer, ovarian cancer, liver cancer, melanoma, rhabdomyosarcoma, synovial sarcoma and mesothelioma; wherein the lung cancer is selected from the group consisting of small cell lung cancer and non-small cell lung cancer; wherein the leukemia is selected from the group consisting of chronic myeloid leukemia, acute myeloid leukemia and mixed lineage leukemia; wherein the lymphoma is selected from non-Hodgkin's lymphoma, diffuse large B-cell lymphoma and follicular lymphoma.

The present invention is further directed to a compound of formula (I) or a tautomer, mesomer, racemate, enantiomer, diastereomer, or mixture thereof, or a pharmaceutically acceptable salt thereof, or a pharmaceutical composition comprising the same for use as a medicament for preventing and/or treating tumor and cancer, wherein the tumor and cancer are as defined above.

The present invention is also directed to a method for the preventing and/or treating tumor and cancer, comprising administering to a patient in need thereof a therapeutically effective amount of a compound of formula (I) or a tautomer, mesomer, racemate, enantiomer, diastereomer, or mixture thereof, or a pharmaceutically acceptable salt thereof, or a pharmaceutical composition comprising the same, wherein the tumor and cancer are as defined above.

The present invention is further directed to use of a compound of formula (I) or a tautomer, mesomer, racemate, enantiomer, diastereomer, or mixture thereof, or a pharmaceutically acceptable salt thereof, or a pharmaceutical composition comprising the same, as an EZH2 inhibitor in the preparation of a medicament for preventing and/or treating tumor and cancer, wherein the tumor and cancer are as defined above.

The present invention is further directed to use of a compound of formula (I) or a tautomer, mesomer, racemate, enantiomer, diastereomer, or mixture thereof, or a pharmaceutically acceptable salt thereof, or a pharmaceutical composition comprising the same, in the preparation of a medicament for inhibiting EZH2.

The present invention is further directed to a compound of formula (I) or a tautomer, mesomer, racemate, enantiomer, diastereomer, or mixture thereof, or a pharmaceutically acceptable salt thereof, or a pharmaceutical composition comprising the same for use as a medicament for inhibiting EZH2.

The present invention also directed to a method for inhibiting EZH2, comprising administering to a patient in need thereof a therapeutically effective amount of the compound of formula (I) or a tautomer, mesomer, racemate, enantiomer, diastereomer, or mixture thereof, or a pharmaceutically acceptable salt thereof, or a pharmaceutical composition comprising the same.

Pharmaceutical compositions containing the active ingredient can be in a form suitable for oral administration, for example, a tablet, troche, lozenge, aqueous or oily suspension, dispersible powder or granule, emulsion, hard or soft capsule, or syrup or elixir. Oral compositions can be prepared according to any method known in the art for the preparation of pharmaceutical compositions. Such compositions can contain one or more agents selected from the group consisting of sweetening agents, flavoring agents, coloring agents and preservatives, in order to provide a pleasing and palatable pharmaceutical formulation. The tablet contains the active ingredient in admixture with non-toxic pharmaceutically acceptable excipients suitable for the manufacture of a tablet.

An aqueous suspension contains the active ingredient in admixture with excipients suitable for the manufacture of an aqueous suspension. The aqueous suspension can also contain one or more preservatives, such as ethylparaben or n-propylparaben, one or more coloring agents, one or more flavoring agents, and one or more sweetening agents, such as sucrose, saccharin or aspartame.

An oil suspension can be formulated by suspending the active ingredient in a vegetable oil. The oil suspension can contain a thickener. The aforementioned sweetening agents and flavoring agents can be added to provide a palatable preparation.

The active ingredient in admixture with the dispersing or wetting agents, suspending agents or one or more preservatives can be prepared as a dispersible powder or granule suitable for the preparation of an aqueous suspension by adding water. Suitable dispersant or wetting agents and suspending agents are exemplified by those already mentioned above. Additional excipients, such as sweetening, flavoring, and coloring agents, can also be added. These compositions can be preserved by adding an antioxidant such as ascorbic acid.

The present pharmaceutical composition can also be in the form of an oil-in-water emulsion.

The pharmaceutical composition can be in the form of sterile injectable aqueous solution. The acceptable vehicles and solvents that can be employed are water, Ringer's solution and isotonic sodium chloride solution. The sterile injectable preparation can also be a sterile injectable oil-in-water microemulsion in which the active ingredient is dissolved in the oil phase. For example, the active ingredient can be firstly dissolved in a mixture of soybean oil and lecithin, the oil solution is then introduced into a mixture of water and glycerol and processed to form a microemulsion. The injectable solution or microemulsion can be introduced into an individual's bloodstream by local bolus injection. Alternatively, it can be advantageous to administer the solution or microemulsion in such a way as to maintain a constant circulating concentration of the present compound. In order to maintain such a constant concentration, a continuous intravenous delivery device can be utilized. An example of such a device is Deltec CADD-PLUS.™5400 intravenous injection pump.

The pharmaceutical composition can be in the form of a sterile injectable aqueous or oily suspension for intramuscular and subcutaneous administration. Such a suspension can be formulated with suitable dispersants or wetting agents and suspending agents as described above according to known techniques. The sterile injectable preparation can also be a sterile injectable solution or suspension prepared in a nontoxic parenterally acceptable diluent or solvent. Moreover, a sterile fixed oil can easily be used as a solvent or suspending medium.

The present compound can be administrated in the form of a suppository for rectal administration. These pharmaceutical compositions can be prepared by mixing drug with a suitable non-irritating excipient that is solid at ordinary temperatures, but liquid in the rectum, thereby melting in the rectum to release the drug. Such materials include cocoa butter, glycerin gelatin, hydrogenated vegetable oils, mixtures of polyethylene glycols with various molecular weights and fatty acid esters of polyethylene glycols.

It is well known to those skilled in the art that the dosage of a drug depends on a variety of factors including, but not limited to, the following factors: activity of a specific compound, age of the patient, weight of the patient, general health of the patient, behavior of the patient, diet of the patient, administration time, administration route, excretion rate, drug combination and the like. In addition, the best treatment, such as treatment mode, daily dose of the compound of formula (I) or the type of pharmaceutically acceptable salt thereof can be verified by traditional therapeutic regimens.

DETAILED DESCRIPTION OF THE INVENTION

Unless otherwise stated, the terms used in the specification and claims have the meanings described below.

"Alkyl" refers to a saturated aliphatic hydrocarbon group including $C_1$ to $C_{20}$ straight chain and branched chain groups, preferably an alkyl having 1 to 12 carbon atoms, and more preferably an alkyl having 1 to 6 carbon atoms. Non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, n-heptyl, 2-methylhexyl, 3-methylhexyl, 4-methylhexyl, 5-methylhexyl, 2,3-dimethylpentyl, 2,4-dimethylpentyl, 2,2-dimethylpentyl, 3,3-dimethylpentyl, 2-ethylpentyl, 3-ethylpentyl, n-octyl, 2,3-dimethylhexyl, 2,4-dimethylhexyl, 2,5-dimethylhexyl, 2,2-dimethylhexyl, 3,3-dimethylhexyl, 4,4-dimethylhexyl, 2-ethylhexyl, 3-ethylhexyl, 4-ethylhexyl, 2-methyl-2-ethylpentyl, 2-methyl-3-ethylpentyl, n-nonyl, 2-methyl-2-ethylhexyl, 2-methyl-3-ethylhexyl, 2,2-diethylpentyl, n-decyl, 3,3-diethylhexyl, 2,2-diethylhexyl, and branched isomers thereof. More preferably, an alkyl group is a lower alkyl having 1 to 6 carbon atoms, and non-limiting examples include methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and the like. The alkyl group can be substituted or unsubstituted. When substituted, the substituent group(s) can be substituted at any available connection point. The substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy, and alkoxycarbonyl.

"Alkylene" refers to an alkyl of which a hydrogen atom is further substituted, for example, "methylene" refers to —$CH_2$—, "ethylene" refers to —$(CH_2)_2$—, "propylene" refers to —$(CH_2)_3$—, "butylene" refers to —$(CH_2)_4$— and the like.

"Alkenyl" refers to an alkyl as defined above that has at least two carbon atoms and at least one carbon-carbon double bond, for example, ethenyl, 1-propenyl, 2-propenyl, 1-, 2- or 3-butenyl and the like. The alkenyl group can be substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio and heterocyclic alkylthio.

"Cycloalkyl" refers to a saturated and/or partially unsaturated monocyclic or polycyclic hydrocarbon group having 3 to 20 carbon atoms, preferably 3 to 12 carbon atoms, and more preferably 3 to 6 carbon atoms. Non-limiting examples of monocyclic cycloalkyl include cyclopropyl, cyclobutyl, cyclopentyl, cyclopentenyl, cyclohexyl, cyclohexenyl, cyclohexadienyl, cycloheptyl, cycloheptatrienyl, cyclooctyl, and the like. Polycyclic cycloalkyl includes a cycloalkyl having a spiro ring, fused ring or bridged ring.

"Spiro cycloalkyl" refers to a 5 to 20 membered polycyclic group with rings connected through one common carbon atom (called a spiro atom), wherein one or more of the rings can contain one or more double bonds, but none of the rings has a completely conjugated pi-electron system, preferably 6 to 14 membered spiro cycloalkyl, and more preferably 7 to 10 membered spiro cycloalkyl. According to the number of the spiro atoms shared between the rings, spiro cycloalkyl can be divided into mono-spiro cycloalkyl, di-spiro cycloalkyl, or poly-spiro cycloalkyl, preferably a mono-spiro cycloalkyl or di-spiro cycloalkyl, and more preferably 4-membered/4-membered, 4-membered/5-membered, 4-membered/6-membered, 5-membered/5-membered, or 5-membered/6-membered mono-spiro cycloalkyl. Non-limiting examples of spiro cycloalkyls include:

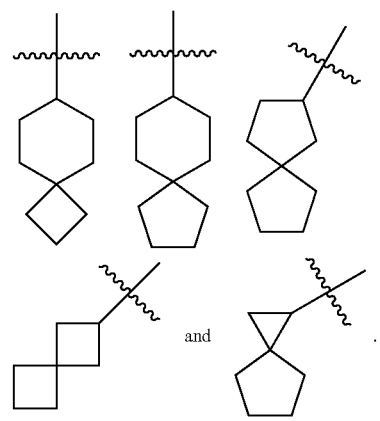

"Fused cycloalkyl" refers to a 5 to 20 membered full-carbon polycyclic group, wherein each ring in the system shares an adjacent pair of carbon atoms with another ring, wherein one or more rings can contain one or more double bonds, but none of the rings has a completely conjugated pi-electron system, preferably 6 to 14 membered fused cycloalkyl, more preferably 7 to 10 membered fused cycloalkyl. According to the number of membered rings, fused cycloalkyl can be divided into bicyclic, tricyclic, tetracyclic or polycyclic fused cycloalkyl, preferably bicyclic or tricyclic fused cycloalkyl, and more preferably 5-membered/5-membered, or 5-membered/6-membered bicyclic fused cycloalkyl. Non-limiting examples of fused cycloalkyls include:

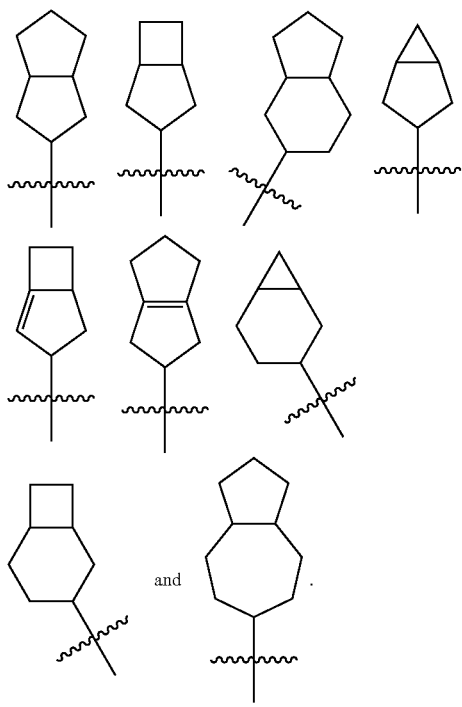

"Bridged cycloalkyl" refers to a 5 to 20 membered full-carbon polycyclic group, wherein every two rings in the system share two disconnected atoms, wherein the rings can have one or more double bonds, but none of the rings has a completely conjugated pi-electron system, preferably 6 to 14 membered bridged cycloalkyl, and more preferably 7 to 10 membered bridged cycloalkyl. According to the number of membered rings, bridged cycloalkyl can be divided into bicyclic, tricyclic, tetracyclic or polycyclic bridged cycloalkyl, preferably bicyclic, tricyclic or tetracyclic bridged cycloalkyl, and more preferably bicyclic or tricyclic bridged cycloalkyl. Non-limiting examples of bridged cycloalkyls include:

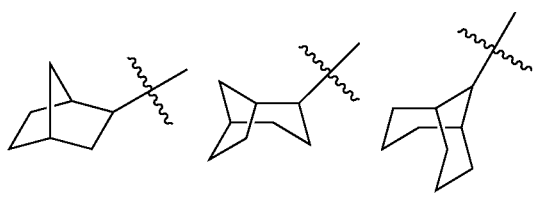

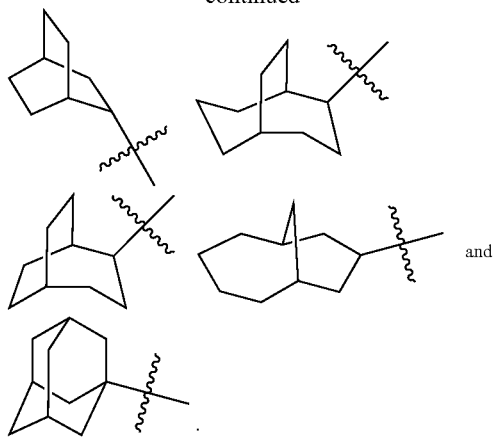

and

The aforementioned cycloalkyl ring can be fused to the ring of aryl, heteroaryl or heterocyclyl, wherein the ring bound to the parent structure is cycloalkyl. Non-limiting examples include indanyl, tetrahydronaphthyl, benzocycloheptyl and the like. The cycloalkyl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy and alkoxycarbonyl.

"Heterocyclyl" refers to a 3 to 20 membered saturated and/or partially unsaturated monocyclic or polycyclic hydrocarbon group having one or more heteroatoms selected from the group consisting of N, O, and S(O)m (wherein m is an integer of 0 to 2) as ring atoms, but excluding —O—O—, —O—S— or —S—S— in the ring, with the remaining ring atoms being carbon atoms. Preferably, heterocyclyl has 3 to 12 atoms wherein 1 to 4 atoms are heteroatoms, more preferably 3 to 8 atoms wherein 1 to 3 atoms are heteroatoms, and most preferably 3 to 6 atoms wherein 1 to 2 atoms are heteroatoms. Non-limiting examples of monocyclic heterocyclyl include pyrrolidinyl, imidazolidinyl, tetrahydrofuranyl, tetrahydrothienyl, dihydroimidazolyl, dihydrofuryl, dihydropyrazolyl, dihydropyrrolyl, piperidinyl, piperazinyl, morpholinyl, thiomorpholinyl, homopiperazinyl, pyranyl and the like, preferably piperidinyl, pyrrolidinyl, pyranyl, morpholinyl or

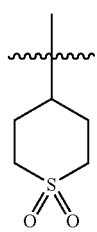

Polycyclic heterocyclyl includes a heterocyclyl having a spiro ring, fused ring or bridged ring.

"Spiro heterocyclyl" refers to a 5 to 20 membered polycyclic heterocyclyl with rings connected through one common atom (called a spiro atom), wherein the rings have one or more heteroatoms selected from the group consisting of N, O, and S(O)m (wherein m is an integer of 0 to 2) as ring atoms, with the remaining ring atoms being carbon atoms, wherein one or more rings can contain one or more double bonds, but none of the rings has a completely conjugated pi-electron system, preferably 6 to 14 membered spiro heterocyclyl, and more preferably 7 to 10 membered spiro heterocyclyl. According to the number of the spiro atoms shared between the rings, spiro heterocyclyl can be divided into mono-spiro heterocyclyl, di-spiro heterocyclyl, or polyspiro heterocyclyl, preferably mono-spiro heterocyclyl or di-spiro heterocyclyl, and more preferably 4-membered/4-membered, 4-membered/5-membered, 4-membered/6-membered, 5-membered/5-membered, or 5-membered/6-membered mono-spiro heterocyclyl. Non-limiting examples of spiro heterocyclyls include:

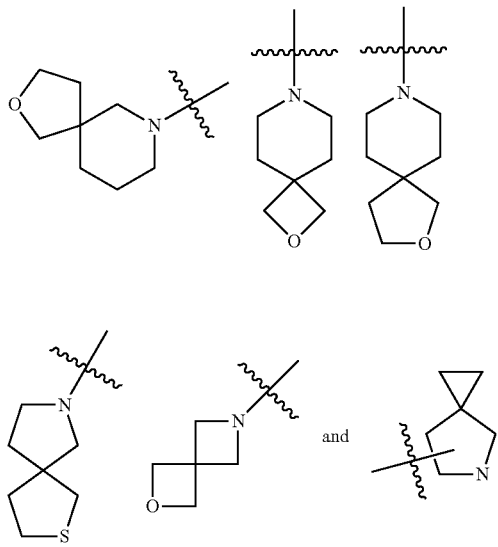

"Fused heterocyclyl" refers to a 5 to 20 membered polycyclic heterocyclyl group, wherein each ring in the system shares an adjacent pair of atoms with another ring, wherein one or more rings can contain one or more double bonds, but none of the rings has a completely conjugated pi-electron system, and wherein the rings have one or more heteroatoms selected from the group consisting of N, O, and S(O)m (wherein m is an integer of 0 to 2) as ring atoms, with the remaining ring atoms being carbon atoms, preferably 6 to 14 membered fused heterocyclyl, and more preferably 7 to 10 membered fused heterocyclyl. According to the number of membered rings, fused heterocyclyl can be divided into bicyclic, tricyclic, tetracyclic or polycyclic fused heterocyclyl, preferably bicyclic or tricyclic fused heterocyclyl, and more preferably 5-membered/5-membered, or 5-membered/6-membered bicyclic fused heterocyclyl. Non-limiting examples of fused heterocyclyls include:

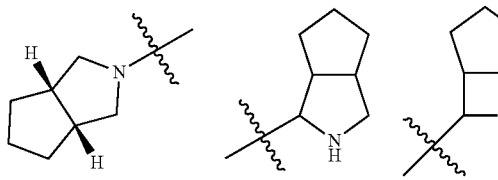

-continued

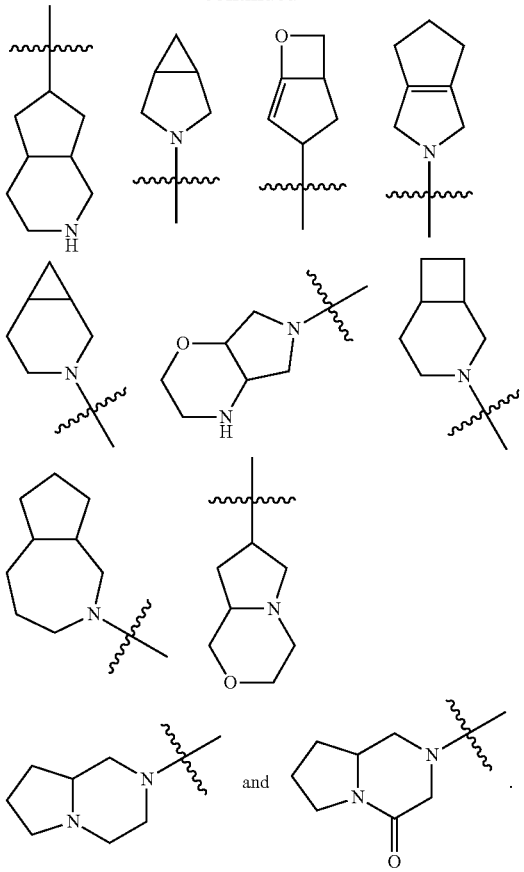

"Bridged heterocyclyl" refers to a 5 to 14 membered polycyclic heterocyclyl group, wherein every two rings in the system share two disconnected atoms, wherein the rings can have one or more double bonds, but none of the rings has a completely conjugated pi-electron system, and the rings have one or more heteroatoms selected from the group consisting of N, O, and S (O)m (wherein m is an integer of 0 to 2) as ring atoms, with the remaining ring atoms being carbon atoms, preferably 6 to 14 membered bridged heterocyclyl, and more preferably 7 to 10 membered bridged heterocyclyl. According to the number of membered rings, bridged heterocyclyl can be divided into bicyclic, tricyclic, tetracyclic or polycyclic bridged heterocyclyl, preferably bicyclic, tricyclic or tetracyclic bridged heterocyclyl, and more preferably bicyclic or tricyclic bridged heterocyclyl. Non-limiting examples of bridged heterocyclyls include:

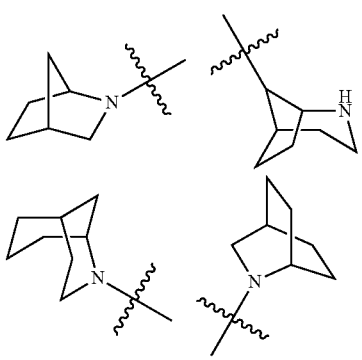

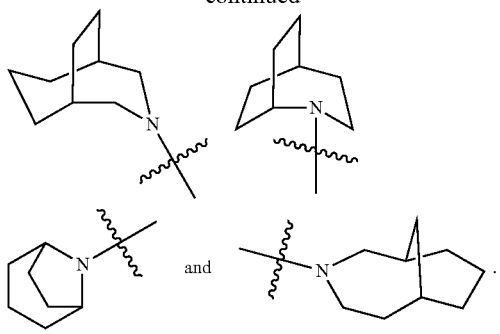

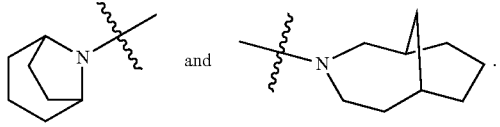

The heterocyclyl ring can be fused to the ring of aryl, heteroaryl or cycloalkyl, wherein the ring bound to the parent structure is heterocyclyl. Non-limiting examples include:

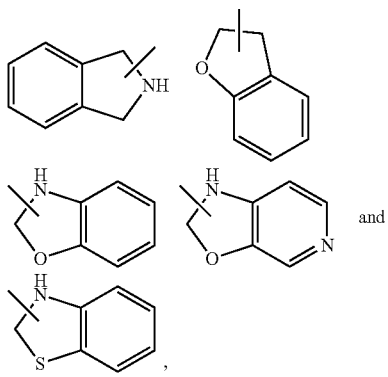

etc.

The heterocyclyl can be optionally substituted or unsubstituted. When substituted, the substituent group(s) is preferably one or more group(s) independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, oxo, carboxy and alkoxycarbonyl.

"Aryl" refers to a 6 to 14 membered full-carbon monocyclic ring or polycyclic fused ring (i.e. each ring in the system shares an adjacent pair of carbon atoms with another ring in the system) having a completely conjugated pi-electron system, preferably 6 to 10 membered aryl, for example, phenyl and naphthyl, and more preferably phenyl. The aryl ring can be fused to the ring of heteroaryl, heterocyclyl or cycloalkyl, wherein the ring bound to the parent structure is aryl ring. Non-limiting examples include:

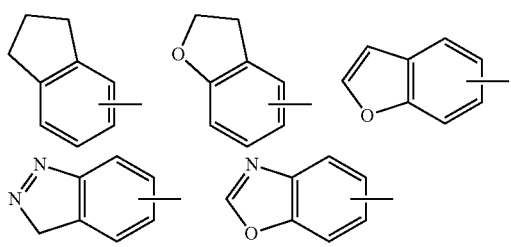

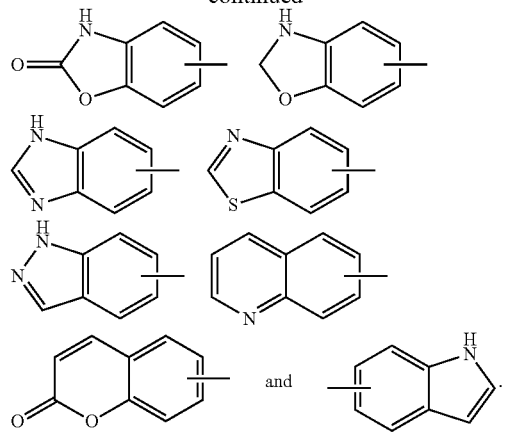

The aryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocyclic alkoxy, cycloalkylthio, heterocyclic alkylthio, carboxy and alkoxycarbonyl.

"Heteroaryl" refers to a 5 to 14 membered heteroaromatic system having 1 to 4 heteroatoms selected from the group consisting of O, S and N as ring atoms, preferably 5 to 10 membered heteroaryl with 1 to 3 heteroatoms, more preferably 5 or 6 membered heteroaryl with 1 to 2 heteroatoms, for example, imidazolyl, furyl, thienyl, thiazolyl, pyrazolyl, oxazolyl, pyrrolyl, tetrazolyl, pyridinyl, pyrimidinyl, thiadiazole, pyrazinyl and the like, preferably imidazolyl, tetrazolyl, thienyl, pyrazolyl, pyrimidinyl or thiazolyl, and more preferably pyrazolyl or thiazolyl. The heteroaryl ring can be fused to the ring of aryl, heterocyclyl or cycloalkyl, wherein the ring bound to the parent structure is heteroaryl ring. Non-limiting examples include:

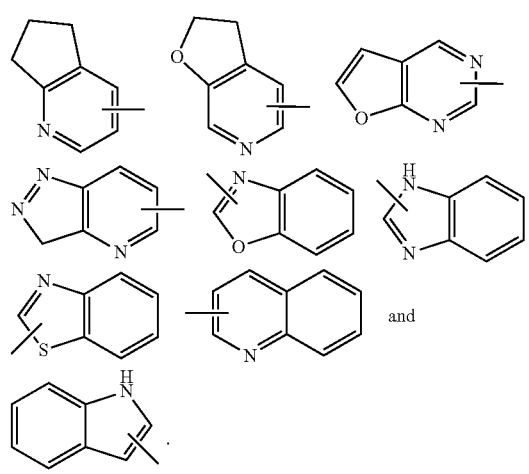

The heteroaryl can be optionally substituted or unsubstituted. When substituted, the substituent group(s) is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy and alkoxycarbonyl.

"Alkoxy" refers to an —O-(alkyl) or an —O-(unsubstituted cycloalkyl) group, wherein the alkyl is as defined above. Non-limiting examples include methoxy, ethoxy, propoxy, butoxy, cyclopropyloxy, cyclobutyloxy, cyclopentyloxy, cyclohexyloxy, and the like. The alkoxy can be optionally substituted or unsubstituted. When substituted, the substituent is preferably one or more groups independently selected from the group consisting of alkyl, alkenyl, alkynyl, alkoxy, alkylthio, alkylamino, halogen, thiol, hydroxy, nitro, cyano, cycloalkyl, heterocyclyl, aryl, heteroaryl, cycloalkoxy, heterocylic alkoxy, cycloalkylthio, heterocyclic alkylthio, carboxy and alkoxycarbonyl.

"Haloalkyl" refers to an alkyl group substituted by one or more halogens, wherein the alkyl is as defined above.

"Haloalkoxy" refers to an alkoxy group substituted by one or more halogens, wherein the alkoxy is as defined above.

"Hydroxyalkyl" refers to an alkyl substituted by hydroxy (s), wherein the alkyl is as defined above.

"Hydroxy" refers to an —OH group.

"Halogen" refers to fluorine, chlorine, bromine or iodine.

"Amino" refers to a —NH$_2$ group.

"Cyano" refers to a —CN group.

"Nitro" refers to a —NO$_2$ group.

"Oxo" refers to a =O group.

"Carbonyl" refers to a C=O group.

"Carboxy" refers to a —C(O)OH group.

"Isocyanato" refers to a —NCO group.

"Hydroxyimino" refers to a =N—OH group.

"Alkoxycarbonyl" refers to a —C(O)O(alkyl) or —C(O)O(cycloalkyl) group, wherein the alkyl and cycloalkyl are as defined above.

"Acyl halide" refers to a compound comprising a —C(O)-halogen group.

"Optional" or "optionally" means that the event or circumstance described subsequently can, but need not, occur, and such a description includes the situation in which the event or circumstance does or does not occur. For example, "the heterocyclyl group optionally substituted by an alkyl" means that an alkyl group can be, but need not be, present, and such a description includes the situation of the heterocyclyl group being substituted by an alkyl and the heterocyclyl group being not substituted by an alkyl.

"Substituted" refers to one or more hydrogen atoms in a group, preferably up to 5, more preferably 1 to 3 hydrogen atoms, independently substituted by a corresponding number of substituents. It goes without saying that the substituents only exist in their possible chemical position. The person skilled in the art is able to determine whether the substitution is possible or impossible by experiments or theory without paying excessive efforts. For example, the combination of amino or hydroxy having free hydrogen and carbon atoms having unsaturated bonds (such as olefinic) can be unstable.

A "pharmaceutical composition" refers to a mixture of one or more of the compounds according to the present invention or physiologically/pharmaceutically acceptable salts or prodrugs thereof and other chemical components, and other components such as physiologically/pharmaceutically acceptable carriers and excipients. The purpose of a pharmaceutical composition is to facilitate administration of a compound to an organism, which is conducive to the absorption of the active ingredient, thus displaying biological activity.

"Pharmaceutically acceptable salt" refers to a salt of the compound of the present invention, which is safe and effective in mammals and has the desired biological activity.

Synthesis Method of the Compound of the Present Invention

In order to achieve the object of the present invention, the present invention applies the following synthesis technical solutions.

A process for preparing a compound of formula (I) of the present invention or a tautomer, mesomer, racemate, enantiomer, diastereomer, or mixture thereof, or a pharmaceutically acceptable salt thereof, comprises the following steps:

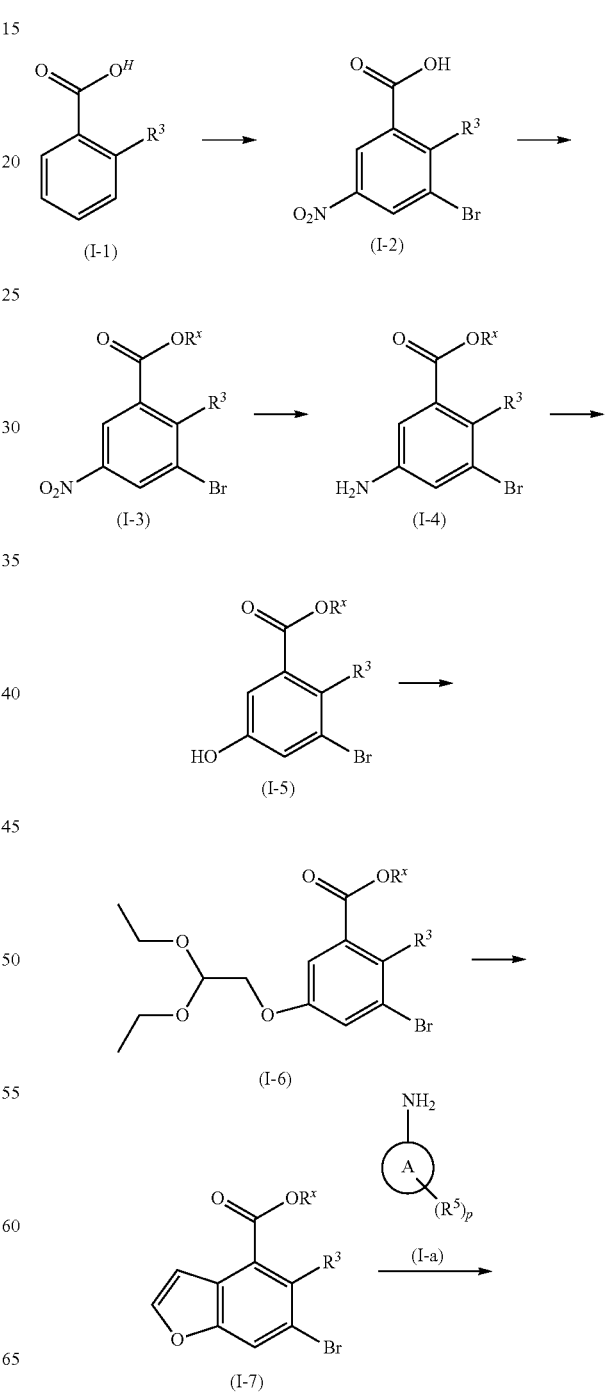

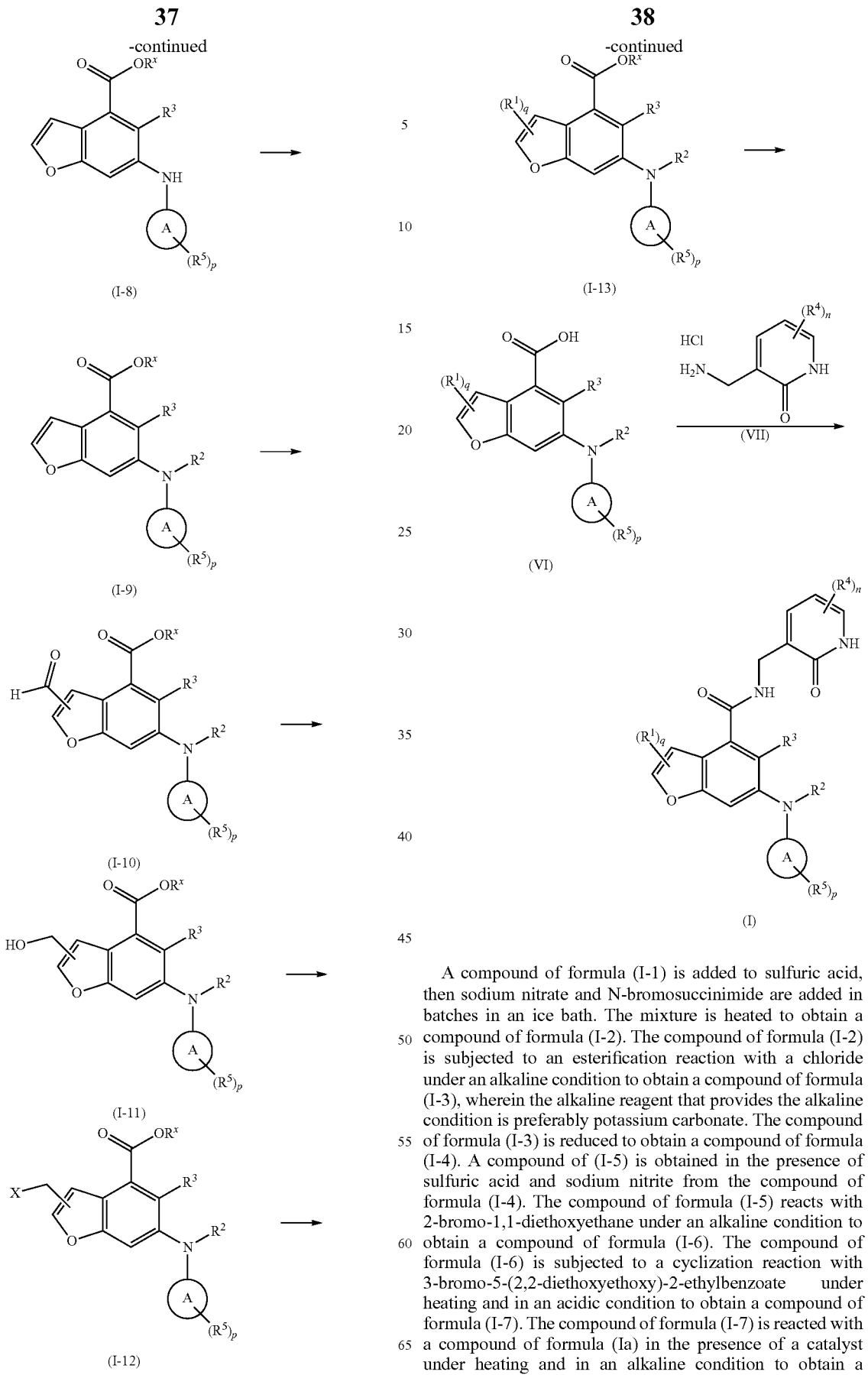

A compound of formula (I-1) is added to sulfuric acid, then sodium nitrate and N-bromosuccinimide are added in batches in an ice bath. The mixture is heated to obtain a compound of formula (I-2). The compound of formula (I-2) is subjected to an esterification reaction with a chloride under an alkaline condition to obtain a compound of formula (I-3), wherein the alkaline reagent that provides the alkaline condition is preferably potassium carbonate. The compound of formula (I-3) is reduced to obtain a compound of formula (I-4). A compound of (I-5) is obtained in the presence of sulfuric acid and sodium nitrite from the compound of formula (I-4). The compound of formula (I-5) reacts with 2-bromo-1,1-diethoxyethane under an alkaline condition to obtain a compound of formula (I-6). The compound of formula (I-6) is subjected to a cyclization reaction with 3-bromo-5-(2,2-diethoxyethoxy)-2-ethylbenzoate under heating and in an acidic condition to obtain a compound of formula (I-7). The compound of formula (I-7) is reacted with a compound of formula (Ia) in the presence of a catalyst under heating and in an alkaline condition to obtain a compound of of formula (I-8), wherein the alkaline reagent that provides the alkaline condition for this reaction is preferably potassium carbonate, and the catalyst is preferably tris(dibenzylideneacetone)dipalladium, or (±)-2,2'-bis(diphenylphosphino)-1,1'-binaphthalene. The compound of formula (I-8) is reacted with an alkyl halide under an alkaline condition to obtain a compound of formula (I-9). The compound of formula (I-9) is reacted with N,N-dimethylformamide under an alkaline condition to obtain a compound of formula (I-10), wherein the alkaline reagent that provides the alkaline condition for this reaction is preferably lithium diisopropylamide. The compound of formula (I-10) is reduced to a compound of formula (I-11) in the presence of a reducing agent, wherein the reducing agent under this condition is preferably sodium borohydride. The compound of formula (I-11) is reacted with phosphorus tribromide to obtain a compound of formula (I-12). The compound of formula (I-12) is reacted with $R^1H$ to obtain a compound of formula (I-13). The compound of formula (I-13) is hydrolyzed under an alkaline condition to obtain a compound of formula (VI), wherein the alkaline reagent that provides the alkaline condition for this reaction is preferably sodium hydroxide. The compound of formula (VI) is subjected to an acylation reaction with a compound of formula (VII) to obtain a compound of formula (I).

The reagent that provides an alkaline condition includes organic bases and inorganic bases, wherein the organic bases include, but are not limited to, triethylamine, N,N-diisopropylethylamine, n-butyllithium, lithium diisopropylamide, potassium acetate, sodium tert-butoxide and potassium tert-butoxide, and wherein the inorganic bases include, but are not limited to, sodium hydride, potassium phosphate, sodium carbonate, potassium carbonate and cesium carbonate.

The catalyst involved includes, but is not limited to, 2-dicyclohexylphosphino-2',4',6'-triisopropylbiphenyl, (±)-2,2'-bis(diphenylphosphino)-1,1'-binaphthalene, tris(dibenzylideneacetone)dipalladium, palladium acetate, [1,1'-bis(diphenylphosphino)ferrocene]dichloropalladium, triphenylphosphine, and tetrakistriphenylphosphine palladium.

Wherein:

$R^x$ is selected from the group consisting of hydrogen, alkyl, haloalkyl, hydroxyalkyl, cycloalkyl, heterocyclyl, aryl and heteroaryl, wherein the alkyl, cycloalkyl, heterocyclyl, aryl and heteroaryl are each independently and optionally substituted by one or more groups selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

X is halogen; and $R^1$ to $R^5$, ring A, p, q and n are as defined in formula (I).

Preferred Embodiments

The present invention will be further described with reference to the following examples, but the examples should not be considered as limiting the scope of the invention.

EXAMPLES

The structures of the compounds are identified by nuclear magnetic resonance (NMR) and/or mass spectrometry (MS). NMR is determined by a Bruker AVANCE-400 machine. The solvents for determination are deuterated-dimethyl sulfoxide (DMSO-$d_6$), deuterated-chloroform (CDCl$_3$) and deuterated-methanol (CD$_3$OD), the internal standard is tetramethylsilane (TMS), and NMR chemical shifts (δ) are given in $10^{-6}$ (ppm).

MS is determined by a FINNIGAN LCQAd (ESI) mass spectrometer (manufacturer: Thermo, type: Finnigan LCQ advantage MAX).

High performance liquid chromatography (HPLC) is determined on an Agilent 1200DAD high pressure liquid chromatography spectrometer (Sunfire C18 150×4.6 mm chromatographic column) and a Waters 2695-2996 high pressure liquid chromatography spectrometer (Gimini C18 150×4.6 mm chromatographic column).

The average kinase inhibition rates and $IC_{50}$ values are determined by a NovoStar ELISA (BMG Co., Germany).

Yantai Huanghai HSGF254 or Qingdao GF254 silica gel plate is used for thin-layer silica gel chromatography (TLC). The dimension of the silica gel plate used in TLC is 0.15 mm to 0.2 mm, and the dimension of the silica gel plate used in product purification is 0.4 mm to 0.5 mm.

Yantai Huanghai 200 to 300 mesh silica gel is used as a carrier for column chromatography.

The known starting materials of the present invention can be prepared by the conventional synthesis methods in the art, or can be purchased from ABCR GmbH & Co. KG, Acros Organnics, Aldrich Chemical Company, Accela ChemBio Inc., or Dari chemical Company, etc.

Unless otherwise stated, the reactions are carried out under an argon atmosphere or nitrogen atmosphere.

The term "argon atmosphere" or "nitrogen atmosphere" means that a reaction flask is equipped with a 1 L argon or nitrogen balloon.

The term "hydrogen atmosphere" means that a reaction flask is equipped with a 1 L hydrogen balloon.

Pressurized hydrogenation reactions are performed with a Parr 3916EKX hydrogenation instrument and a QL-500 hydrogen generator or HC2-SS hydrogenation instrument.

In hydrogenation reactions, the reaction system is generally vacuumed and filled with hydrogen, with the above operation repeated three times.

CEM Discover-S 908860 type microwave reactor is used in microwave reaction.

Unless otherwise stated, the solution used in the reactions refers to an aqueous solution.

Unless otherwise stated, the reaction temperature in the reactions refers to room temperature.

Room temperature is the most appropriate reaction temperature, and ranges from 20° C. to 30° C.

The reaction process is monitored by thin layer chromatography (TLC), and the developing solvent system includes: A: dichloromethane and methanol system, B: n-hexane and ethyl acetate system, C: petroleum ether and ethyl acetate system, D: acetone. The ratio of the volume of the solvent can be adjusted according to the polarity of the compounds.

The elution system for purification of the compounds by column chromatography and thin layer chromatography includes: A: dichloromethane and methanol system, B: n-hexane and ethyl acetate system, C: n-hexane, ethyl acetate and dichloromethane system, D: petroleum ether and ethyl acetate system, E: ethyl acetate. The ratio of the volume of the solvent can be adjusted according to the polarity of the compounds, and sometimes a little alkaline reagent such as triethylamine or acidic reagent can be added.

Example 1
5-Ethyl-6-(ethyl(tetrahydro-2H-pyran-4-yl)amino)-N-((4-methoxy-6-methyl-2-oxo-1,2-dihydropyridin-3-yl)methyl)-2-(piperidin-1-ylmethyl)benzofuran-4-carboxamide
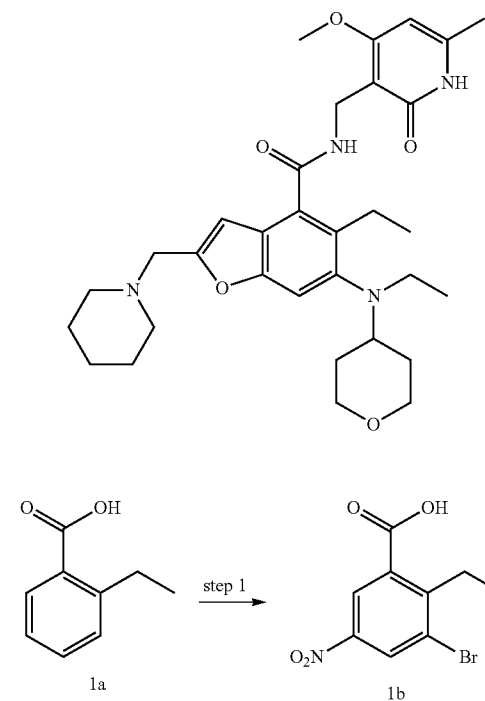
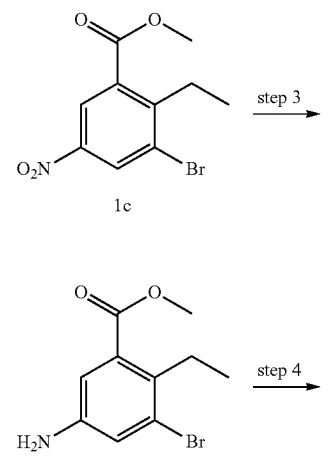
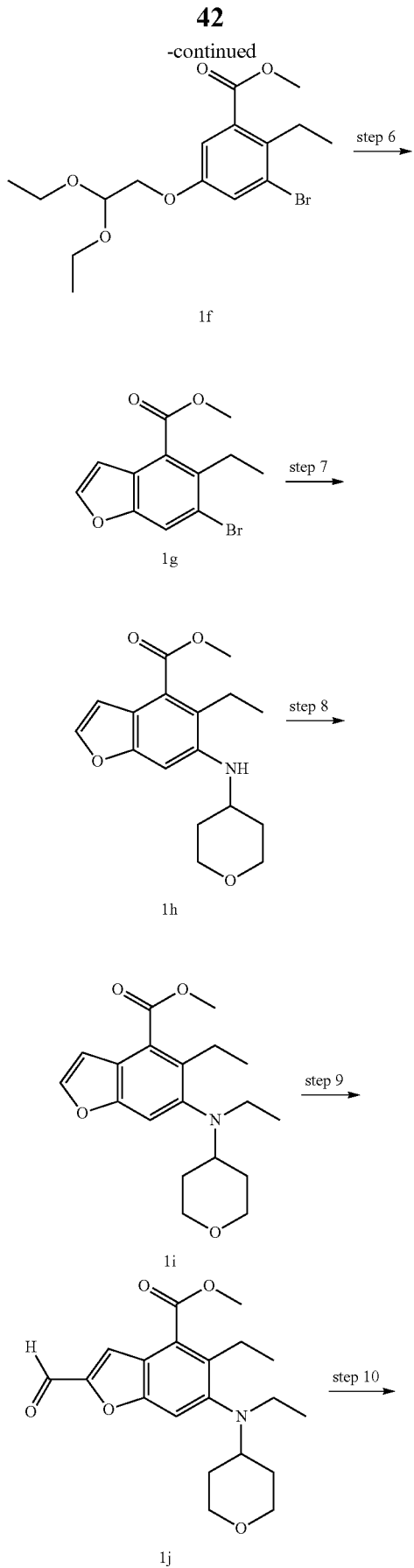

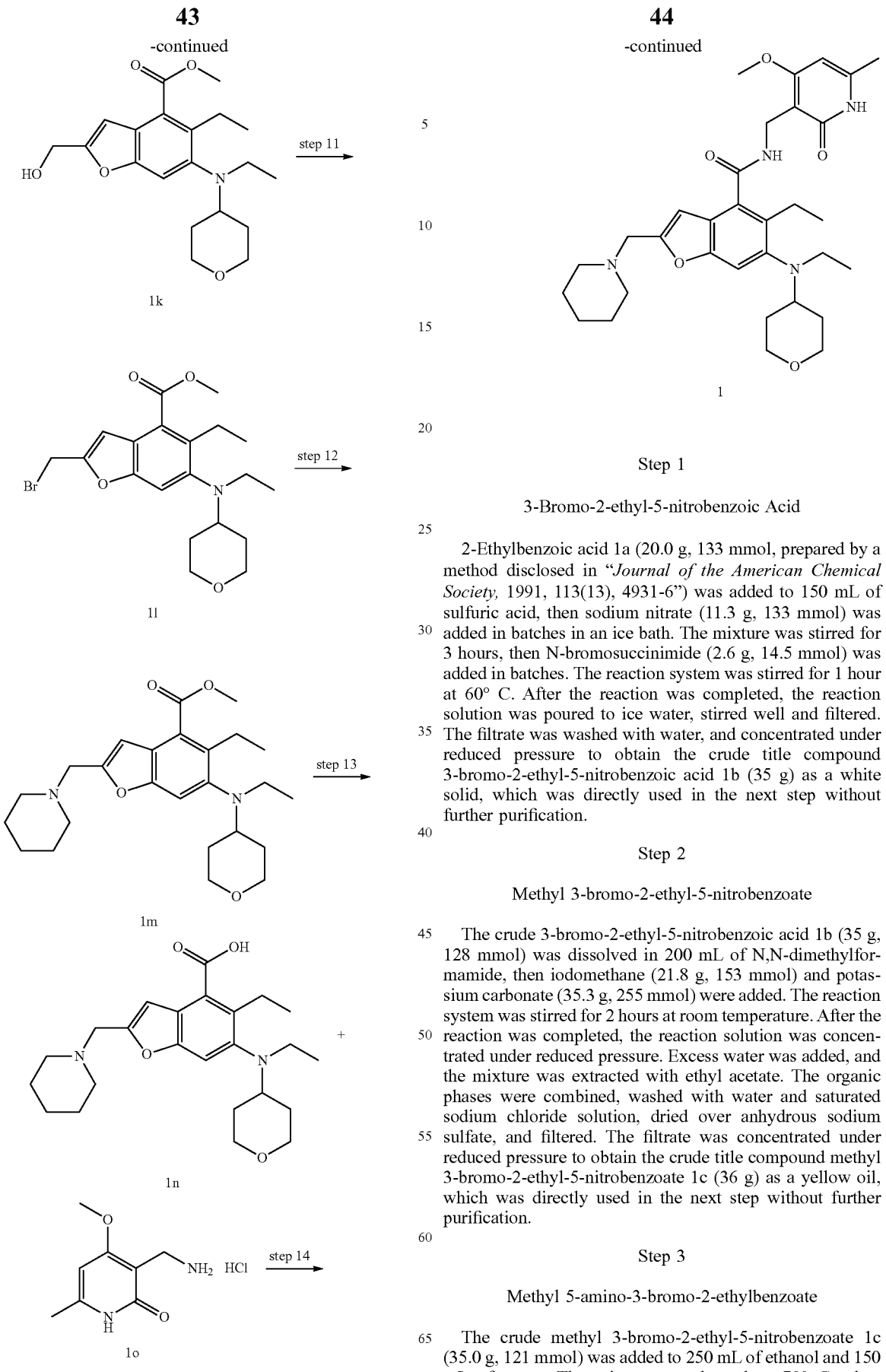

Step 1

3-Bromo-2-ethyl-5-nitrobenzoic Acid

2-Ethylbenzoic acid 1a (20.0 g, 133 mmol, prepared by a method disclosed in "*Journal of the American Chemical Society,* 1991, 113(13), 4931-6") was added to 150 mL of sulfuric acid, then sodium nitrate (11.3 g, 133 mmol) was added in batches in an ice bath. The mixture was stirred for 3 hours, then N-bromosuccinimide (2.6 g, 14.5 mmol) was added in batches. The reaction system was stirred for 1 hour at 60° C. After the reaction was completed, the reaction solution was poured to ice water, stirred well and filtered. The filtrate was washed with water, and concentrated under reduced pressure to obtain the crude title compound 3-bromo-2-ethyl-5-nitrobenzoic acid 1b (35 g) as a white solid, which was directly used in the next step without further purification.

Step 2

Methyl 3-bromo-2-ethyl-5-nitrobenzoate

The crude 3-bromo-2-ethyl-5-nitrobenzoic acid 1b (35 g, 128 mmol) was dissolved in 200 mL of N,N-dimethylformamide, then iodomethane (21.8 g, 153 mmol) and potassium carbonate (35.3 g, 255 mmol) were added. The reaction system was stirred for 2 hours at room temperature. After the reaction was completed, the reaction solution was concentrated under reduced pressure. Excess water was added, and the mixture was extracted with ethyl acetate. The organic phases were combined, washed with water and saturated sodium chloride solution, dried over anhydrous sodium sulfate, and filtered. The filtrate was concentrated under reduced pressure to obtain the crude title compound methyl 3-bromo-2-ethyl-5-nitrobenzoate 1c (36 g) as a yellow oil, which was directly used in the next step without further purification.

Step 3

Methyl 5-amino-3-bromo-2-ethylbenzoate

The crude methyl 3-bromo-2-ethyl-5-nitrobenzoate 1c (35.0 g, 121 mmol) was added to 250 mL of ethanol and 150 mL of water. The mixture was heated to 70° C., then ammonium chloride (52.8 g, 969 mmol) was added, then iron powder (34 g, 606 mmol) was added in batches. The reaction system was stirred for 2 hours at 70° C. After the reaction was completed, the mixture was filtered through celite while hot. The filter cake was washed with hot ethanol, then the filtrate was combined and concentrated under reduced pressure. Ethyl acetate and saturated sodium bicarbonate solution were added. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 5-amino-3-bromo-2-ethylbenzoate 1d (22.0 g, yield 70%) as a yellow solid.

Step 4

Methyl 3-bromo-2-ethyl-5-hydroxybenzoate

Methyl 5-amino-3-bromo-2-ethylbenzoate 1d (15.0 g, 58 mmol) was dissolved in 10 mL of acetonitrile, then 200 mL of 10% sulfuric acid was added. The mixture was stirred well and cooled down to 3° C. in an ice-salt bath, then 10 mL of a pre-prepared solution of sodium nitrite (4.4 g, 64 mmol) was added. The mixture was stirred for 4 hours at the above temperature, added dropwise with 200 mL of 50% sulfuric acid, then stirred for 1 hour at 90° C. After the reaction was completed, the reaction solution was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 3-bromo-2-ethyl-5-hydroxybenzoate 1e (5.5 g, yield 37%) as a brown solid.

Step 5

Methyl 3-bromo-5-(2,2-diethoxyethoxy)-2-ethylbenzoate

Methyl 3-bromo-2-ethyl-5-hydroxybenzoate 1e (35 g, 135 mmol) was dissolved in 200 mL of N,N-dimethylformamide, then 2-bromo-1,1-diethoxyethane (40 g, 202 mmol) and potassium carbonate (37 g, 269 mmol) were added. The reaction system was stirred at 120° C. for 12 hours. After the reaction was completed, the reaction solution was concentrated under reduced pressure to remove N,N-dimethylformamide. Water was added, and the mixture was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 3-bromo-5-(2,2-diethoxyethoxy)-2-ethylbenzoate 1f (40 g, yield 80%) as a light yellow oil.

Step 6

Methyl 6-bromo-5-ethylbenzofuran-4-carboxylate

Polyphosphoric acid (30 g) was added to 400 mL of toluene. The mixture was heated to 100° C., 50 mL of a pre-prepared solution of methyl 3-bromo-5-(2,2-diethoxyethoxy)-2-ethylbenzoate 1f (40 g, 107 mmol) in toluene was added with stirring. The mixture was stirred for 16 hours at 100° C. After the reaction was completed, the supernatant was decanted. Water and ethyl acetate were added to the residue. Two phases were separated, and the aqueous phase was extracted with ethyl acetate. The organic phases were combined, washed with saturated sodium carbonate solution and saturated sodium chloride solution, dried over anhydrous sodium sulfate, and filtered. The filtrate was concentrated under reduced pressure, and the resulting residue was purified by silica gel column chromatography with elution system B to obtain the title compound methyl 6-bromo-5-ethylbenzofuran-4-carboxylate 1g (11.8 g, yield 39%) as a yellow solid.

Step 7

Methyl 5-ethyl-6-((tetrahydro-2H-pyran-4-yl)amino) benzofuran-4-carboxylate

Methyl 6-bromo-5-ethylbenzofuran-4-carboxylate 1g (11.0 g, 39 mmol), tetrahydro-2H-pyran-4-amine (5.89 g, 58 mmol), tris(dibenzylideneacetone)dipalladium (3.6 g, 3.9 mmol), (±)-2,2'-bis(diphenylphosphino)-1,1'-binaphthalene (4.86 g, 7.8 mmol) and cesium carbonate (38 g, 117 mmol) were dissolved in 100 mL of toluene. The mixture was stirred for 12 hours at 100° C. After the reaction was completed, the mixture was filtered through a pad of celite, and the filter cake was washed with ethyl acetate. The organic phases were combined, dried over anhydrous sodium sulfate, and filtered. The filtrate was concentrated under reduced pressure, and the resulting residue was purified by silica gel column chromatography with elution system B to obtain the title compound methyl 5-ethyl-6-((tetrahydro-2H-pyran-4-yl)amino)benzofuran-4-carboxylate 1h (10.0 g, yield 85%) as a yellow solid.

Step 8

Methyl 5-ethyl-6-(ethyl(tetrahydro-2H-pyran-4-yl) amino)benzofuran-4-carboxylate Methyl 5-ethyl-6-((tetrahydro-2H-pyran-4-yl)amino)benzofuran-4-carboxylate 1h (10.0 g, 0.033 mmol) was dissolved in 150 mL of 1,2-dichloroethane, then acetaldehyde (7.2 g, 0.165 mmol) and acetic acid (9.9 g, 0.165 mmol) were added. The mixture was stirred for 1 hour, then sodium triacetoxyborohydride (20.8 g, 0.1 mmol) was added. The mixture was stirred for 12 hours at room temperature. After the reaction was completed, the reaction solution was concentrated under reduced pressure, neutralized with saturated sodium bicarbonate solution, and extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 5-ethyl-6-(ethyl(tetrahydro-2H-pyran-4-yl)amino)benzofuran-4-carboxylate 1i (7.8 g, yield 71%) as a white solid.

MS m/z (LC-MS): 332.4 [M+1]

Step 9

Methyl 5-ethyl-6-(ethyl(tetrahydro-2H-pyran-4-yl) amino)-2-formylbenzofuran-4-carboxylate Methyl 5-ethyl-6-(ethyl(tetrahydro-2H-pyran-4-yl) amino)benzofuran-4-carboxylate 1i (1.6 g, 4.8 mmol) was dissolved in 25 mL of tetrahydrofuran. The mixture was cooled down to −70° C., then 2.0 M lithium diisopropylamide (3.6 mL, 7.3 mmol) was added dropwise under an argon atmosphere. At −70° C., the mixture was stirred for 90 minutes, then N,N-dimethylformamide (536 mg, 7.3 mmol) was added. The mixture was stirred for 2 hours, then slowly warmed up to room temperature. Excess ammonium chloride was added. The mixture was stirred well and extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 5-ethyl-6-(ethyl(tetrahydro-2H-pyran-4-yl)amino)-2-formylbenzofuran-4-carboxylate 1j (1.3 g, yield 75%) as a yellow oil.

MS m/z (ESI):360.2 [M+1]

Step 10

Methyl 5-ethyl-6-(ethyl(tetrahydro-2H-pyran-4-yl)amino)-2-(hydroxymethyl)benzofuran-4-carboxylate Methyl 5-ethyl-6-(ethyl(tetrahydro-2H-pyran-4-yl)amino)-2-formylbenzofuran-4-carboxylate 1j (1.4 g, 3.9 mmol) was dissolved in 5 mL of tetrahydrofuran and 10 mL of methanol, then sodium borohydride (222 mg, 5.8 mmol) was added. The mixture was stirred for 30 minutes at room temperature. After the reaction was completed, the reaction solution was concentrated under reduced pressure, water and saturated sodium bicarbonate solution were added, and the mixture was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 5-ethyl-6-(ethyl(tetrahydro-2H-pyran-4-yl)amino)-2-(hydroxymethyl)benzofuran-4-carboxylate 1k (1.4 g, yield 99%) as a yellow oil.

Step 11

Methyl 2-(bromomethyl)-5-ethyl-6-(ethyl(tetrahydro-2H-pyran-4-yl)amino)benzofuran-4-carboxylate Methyl 5-ethyl-6-(ethyl(tetrahydro-2H-pyran-4-yl)amino)-2-(hydroxymethyl) benzofuran-4-carboxylate 1k (1.0 g, 2.8 mmol) was dissolved in 30 mL of tetrahydrofuran, then phosphorus tribromide (1.12 g, 4.2 mmol) was added dropwise. The mixture was stirred for 12 hours at room temperature. After the reaction was completed, the mixture was neutralized with saturated sodium bicarbonate solution, and extracted with ethyl acetate. The organic phases were combined, washed with saturated sodium chloride solution, dried over anhydrous sodium sulfate, and filtered. The filtrate was concentrated under reduced pressure to obtain the crude title compound methyl 2-(bromomethyl)-5-ethyl-6-(ethyl(tetrahydro-2H-pyran-4-yl)amino) benzofuran-4-carboxylate 1l (1.15 g) as a yellow oil, which was directly used in the next step without further purification.

Step 12

Methyl 5-ethyl-6-(ethyl(tetrahydro-2H-pyran-4-yl)amino)-2-(piperidin-1-ylmethyl)benzofuran-4-carboxylate The crude methyl 2-(bromomethyl)-5-ethyl-6-(ethyl(tetrahydro-2H-pyran-4-yl)amino)benzofuran-4-carboxylate 1l (1.15 g, 2.7 mmol) was dissolved in 15 mL of acetonitrile, then 10 mL of a pre-prepared solution of piperidine (362 mg, 4.3 mmol) in acetonitrile were added dropwise. The mixture was stirred for 30 minutes at room temperature. After the reaction was completed, the reaction solution was concentrated under reduced pressure. Ethyl acetate and saturated sodium bicarbonate solution were added. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system A to obtain the title compound methyl 5-ethyl-6-(ethyl(tetrahydro-2H-pyran-4-yl)amino)-2-(piperidin-1-ylmethyl)benzofuran-4-carboxylate 1m (1.2 g, yield 99%) as a yellow oil.

MS m/z (LC-MS): 429.2[M+1]

Step 13

5-Ethyl-6-(ethyl(tetrahydro-2H-pyran-4-yl)amino)-2-(piperidin-1-ylmethyl)benzofuran-4-carboxylic acid Methyl 5-ethyl-6-(ethyl(tetrahydro-2H-pyran-4-yl)amino)-2-(piperidin-1-ylmethyl) benzofuran-4-carboxylate 1m (1.2 g, 2.7 mmol) was dissolved in 5 mL of tetrahydrofuran and 20 mL of methanol, then 5 mL of 4M sodium hydroxide solution were added. The mixture was stirred for 12 hours at 60° C. After the reaction was completed, concentrated hydrochloric acid was added to adjust the pH of the reaction solution to 4. The mixture was concentrated under reduced pressure, and the residue was dissolved in a mixture of dichloromethane and methanol (V:V=5:1) and filtered. The filter cake was washed with a mixture of dichoromethane and methanol (V:V=5:1). The filtrate was combined, and concentrated under reduced pressure to obtain the crude title compound 5-ethyl-6-(ethyl(tetrahydro-2H-pyran-4-yl)amino)-2-(piperidin-1-ylmethyl)benzofuran-4-carboxylic acid 1n (1.1 g) as a yellow solid, which was directly used in the next step without further purification.

MS m/z (LC-MS): 415.2[M+1]

Step 14

5-Ethyl-6-(ethyl(tetrahydro-2H-pyran-4-yl)amino)-N-((4-methoxy-6-methyl-2-oxo-1,2-dihydropyridin-3-yl)methyl)-2-(piperidin-1-ylmethyl)benzofuran-4-carboxamide The crude 5-ethyl-6-(ethyl(tetrahydro-2H-pyran-4-yl)amino)-2-(piperidin-1-ylmethyl)benzofuran-4-carboxylic acid 1n (150 mg, 0.36 mmol) was dissolved in 5 mL of N,N-dimethylformamide, then 1-ethyl-3-(3-dimethylaminopropyl)carbodiimide (104 mg, 0.54 mmol), 1-hydroxybenzotriazole (73 mg, 0.54 mmol) and N,N-diisopropylethylamine (232 mg, 1.8 mmol) were added. The mixture was stirred 1 hour, then 3-(aminomethyl)-4-methoxy-6-methylpyridin-2(1H)-one hydrochloride 1o (96 mg, 0.47 mmol, prepared by a method disclosed in the patent application "WO2014177982") was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl (tetrahydro-2H-pyran-4-yl)amino)-N-((4-methoxy-6-methyl-2-oxo-1,2-dihydropyridin-3-yl)methyl)-2-(piperidin-1-ylmethyl)benzofuran-4-carboxamide 1 (155 mg, yield 76%) as a white solid.

MS m/z (ESI): 565.3 [M+1]

$^1$H NMR (400 MHz, DMSO-$d_6$): δ 11.44 (s, 1H), 8.00 (s, 1H), 7.40 (s, 1H), 6.53 (brs, 1H), 6.10 (s, 1H), 4.29 (d, 2H), 3.85 (brs, 2H), 3.83 (s, 3H), 3.56 (brs, 2H), 3.22 (t, 2H), 3.03-3.08 (m, 2H), 2.93-2.98 (m, 1H), 2.78-2.84 (m, 2H), 2.42 (brs, 4H), 2.18 (s, 3H), 1.64-1.67 (brd, 2H), 1.47-1.56 (m, 6H), 1.38 (brs, 2H), 1.06 (t, 3H), 0.83 (t, 3H).

Example 2

N-((4,6-Dimethyl-2-oxo-1,2-dihydropyridin-3-yl) methyl)-5-ethyl-6-(ethyl(tetrahydro-2H-pyran-4-yl) amino)-2-(piperidin-1-ylmethyl)benzofuran-4-carboxamide

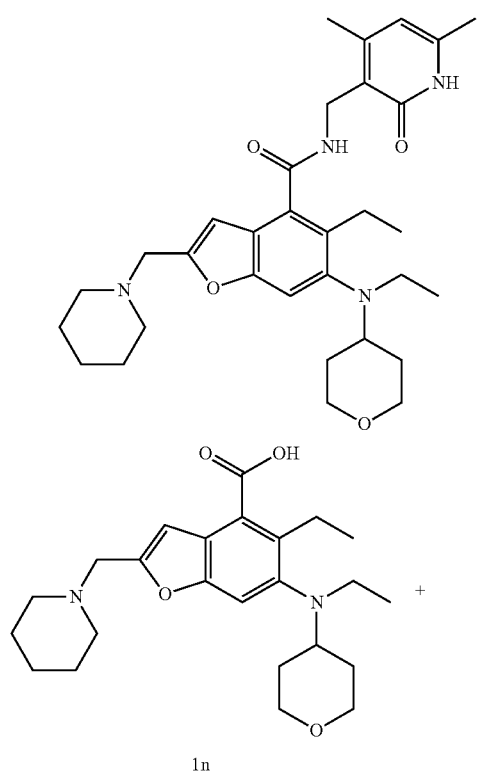

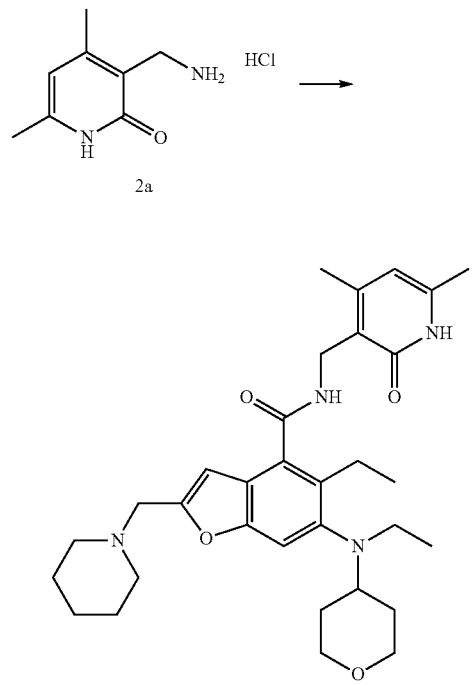

5-Ethyl-6-(ethyl(tetrahydro-2H-pyran-4-yl)amino)-2-(piperidin-1-ylmethyl)benzofuran-4-carboxylic acid in (1.0 g, 2.4 mmol) was dissolved in 30 mL of N,N-dimethylformamide, then 1-ethyl-3-(3-dimethylaminopropyl)carbodiimide (696 mg, 3.6 mmol), 1-hydroxybenzotriazole (490 mg, 3.6 mmol) and N,N-diisopropylethylamine (1.56 g, 12.1 mmol) were added. The mixture was stirred for 1 hour, then 3-(aminomethyl)-4,6-dimethylpyridin-2(1H)-one hydrochloride 2a (593 mg, 3.0 mmol, prepared by a method disclosed in the patent application "WO2014097041") was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by silica gel column chromatography with elution system A to obtain the title compound N-((4,6-dimethyl-2-oxo-1,2-dihydropyridin-3-yl)methyl)-5-ethyl-6-(ethyl(tetrahydro-2H-pyran-4-yl)amino)-2-(piperidin-1-ylmethyl)benzofuran-4-carboxamide 2 (750 mg, yield 57%) as a white solid.

MS m/z (ESI): 549.7 [M+1]

$^1$H NMR (400 MHz, DMSO-$d_6$): δ 11.48 (s, 1H), 8.15 (t, 1H), 7.39 (s, 1H), 6.46 (s, 1H), 5.86 (s, 1H), 4.32 (d, 2H), 3.83 (d, 2H), 3.54 (s, 2H), 3.21 (t, 2H), 3.01-3.07 (m, 2H), 2.92-2.97 (m, 1H), 2.77-2.82 (m, 2H), 2.39 (brs, 4H), 2.23 (s, 3H), 2.11 (s, 3H), 1.64-1.67 (brd, 2H), 1.47-1.55 (m, 6H), 1.36-1.37 (brd, 2H), 1.02 (t, 3H), 0.82 (t, 3H).

Example 3

5-Ethyl-6-(ethyl(tetrahydro-2H-pyran-4-yl)amino)-N-((4-ethyl-6-methyl-2-oxo-1,2-dihydropyridin-3-yl)methyl)-2-(piperidin-1-ylmethyl)benzofuran-4-carboxamide

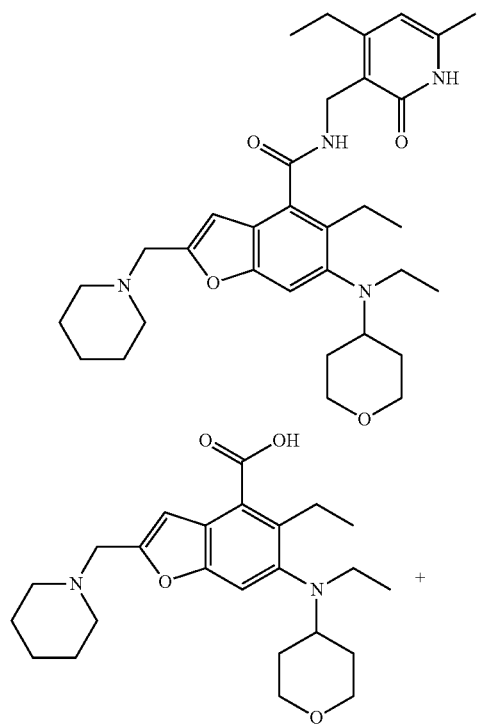

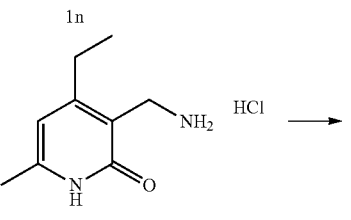

5-Ethyl-6-(ethyl(tetrahydro-2H-pyran-4-yl)amino)-2-(piperidin-1-ylmethyl)benzofuran-4-carboxylic acid 1n (50 mg, 0.12 mmol) was dissolved in 3 mL of N,N-dimethylformamide, then 1-ethyl-3-(3-dimethylaminopropyl)carbodiimide (35 mg, 0.18 mmol), 1-hydroxybenzotriazole (24 mg, 0.18 mmol) and N,N-diisopropylethylamine (78 mg, 0.60 mmol) were added. The mixture was stirred for 1 hour, then 3-(aminomethyl)-4-ethyl-6-methylpyridin-2(1H)-one hydrochloride 3a (36 mg, 0.18 mmol, prepared by a method disclosed in the patent application "WO2013173441") was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl(tetrahydro-2H-pyran-4-yl)amino)-N-((4-ethyl-6-methyl-2-oxo-1,2-dihydropyridin-3-yl)methyl)-2-(piperidin-1-ylmethyl)benzofuran-4-carboxamide 3 (58 mg, yield 85%) as a white solid.

MS m/z (ESI): 563.7 [M+1]

$^1$H NMR (400 MHz, DMSO-d$_6$): δ 11.51 (s, 1H), 8.12 (t, 1H), 7.39 (s, 1H), 6.47 (s, 1H), 5.91 (s, 1H), 4.33 (d, 2H), 3.81-3.83 (brd, 2H), 3.54 (brs, 2H), 3.20 (t, 2H), 3.01-3.06 (m, 2H), 2.91-2.97 (m, 1H), 2.76-2.82 (m, 2H), 2.59 (q, 2H), 2.39 (brs, 4H), 2.13 (s, 3H), 1.63-1.66 (brd, 2H), 1.48-1.50 (m, 6H), 1.36 (brs, 2H), 1.37 (t, 3H), 1.01 (t, 3H), 0.81 (t, 3H).

Example 4

6-(Ethyl(tetrahydro-2H-pyran-4-yl)amino)-N-((4-methoxy-6-methyl-2-oxo-1,2-dihydro pyridin-3-yl)methyl)-5-methyl-2-(piperidin-1-ylmethyl)benzofuran-4-carboxamide

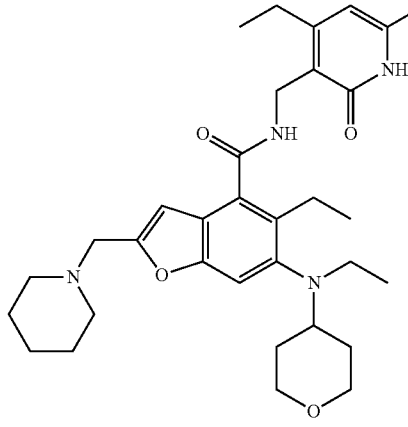

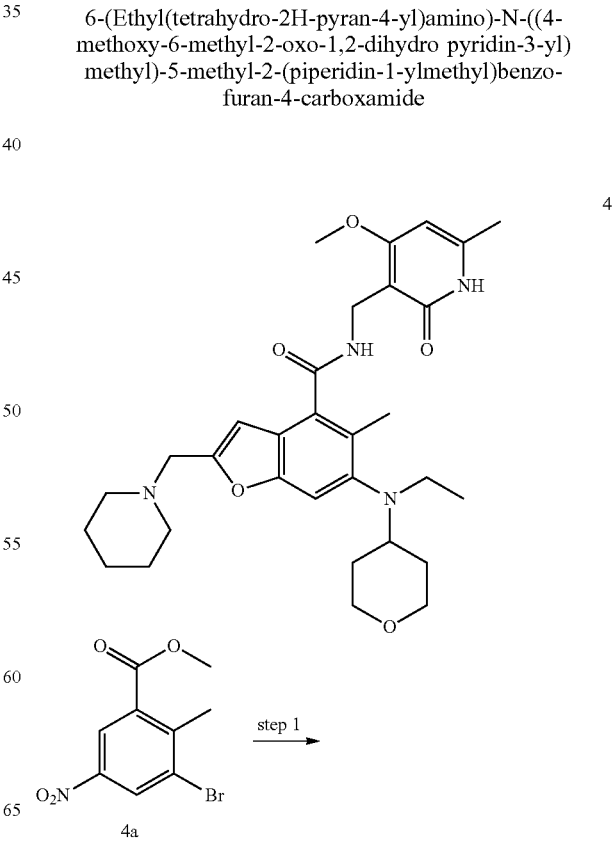

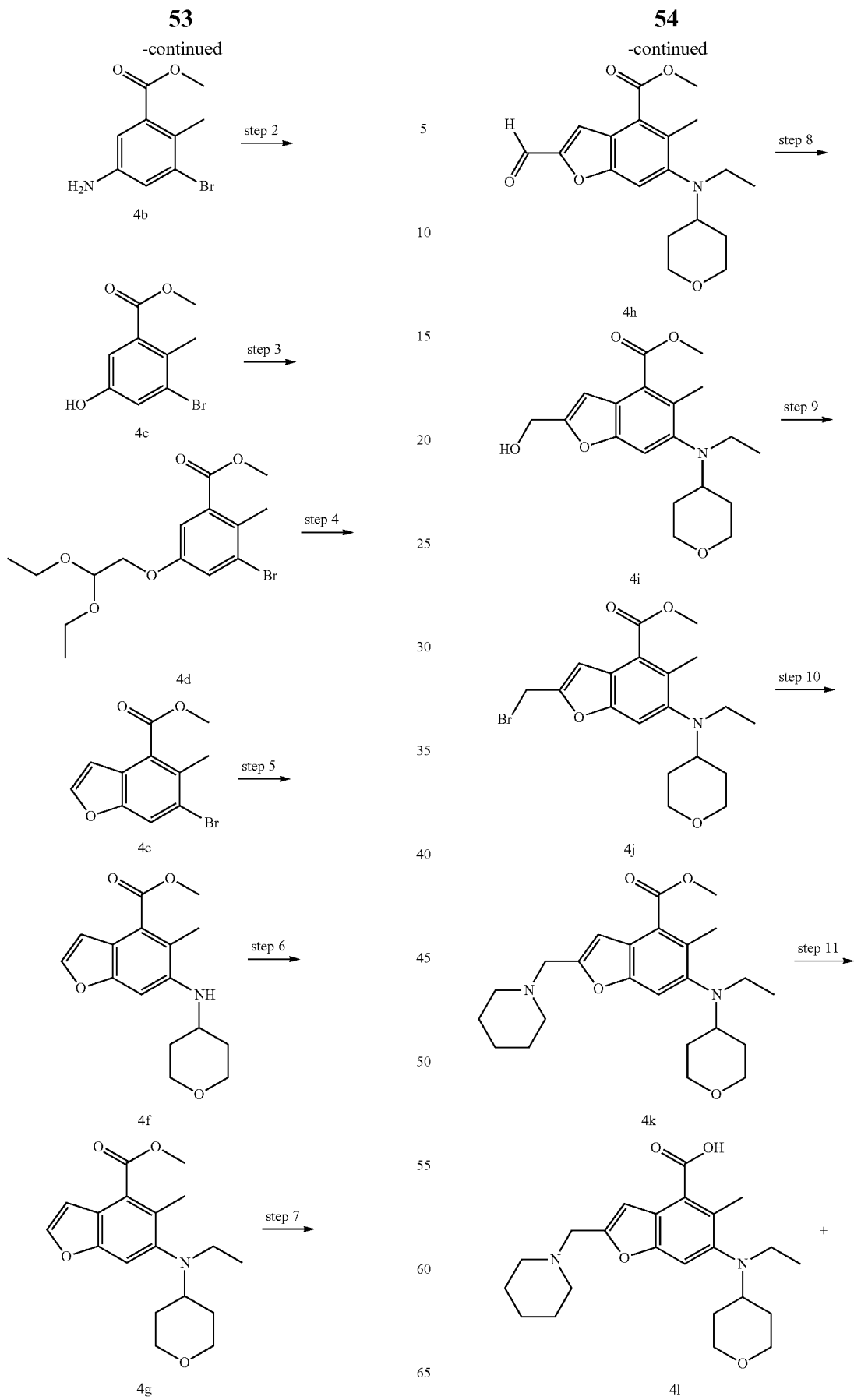

-continued

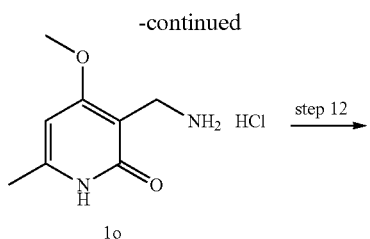

1o

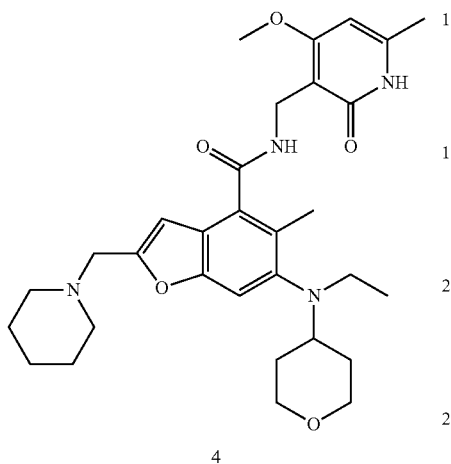

4

Step 1

Methyl 5-amino-3-bromo-2-methylbenzoate

Methyl 3-bromo-2-methyl-5-nitrobenzoate 4a (13 g, 47.3 mmol, prepared by a method disclosed in the patent application "WO2012061602") was added to 200 mL of ethanol and 50 mL of water. The mixture was heated to 70° C., then ammonium chloride (20.6 g, 378 mmol) was added, and iron powder (13.3 g, 236 mmol) was added in batches. The reaction system was stirred for 2 hours at 70° C. After the reaction was completed, the mixture was filtered through a pad of celite while hot. The filter cake was washed with hot ethanol, then the filtrate was combined and concentrated under reduced pressure. The residue was neutralized with saturated sodium bicarbonate solution, and extracted three times with ethyl acetate. The organic phases were combined, dried over anhydrous sodium sulfate, and filtered. The filtrate was concentrated under reduced pressure, and the resulting residue was purified by silica gel column chromatography with elution system B to obtain the title compound methyl 5-amino-3-bromo-2-methylbenzoate 4b (11.0 g, yield 95%) as a yellow solid.

Step 2

Methyl 3-bromo-5-hydroxy-2-methylbenzoate

Methyl 5-amino-3-bromo-2-methylbenzoate 4b (3.0 g, 0.012 mmol) was suspended in 20 mL of 10% sulfuric acid. The mixture was cooled down to 0° C., then 5 mL of a pre-prepared solution of sodium nitrite (1.0 g, 14.7 mmol) were added dropwise. After stirring for 3 hours at the above temperature, the reaction solution was poured into 30 mL of pre-prepared 10% sulfuric acid at 80° C., then stirred for 1 hour at 80° C. After the reaction was completed, the reaction solution was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 3-bromo-5-hydroxy-2-methylbenzoate 4c (1.1 g, yield 32%) as a yellow solid.

Step 3

Methyl 3-bromo-5-(2,2-diethoxyethoxy)-2-methylbenzoate

Methyl 3-bromo-5-hydroxy-2-methylbenzoate 4c (800 mg, 3.3 mmol) was dissolved in 15 mL of N,N-dimethylformamide, then 2-bromo-1,1-diethoxyethane (965 mg, 4.9 mmol) and potassium carbonate (900 mg, 6.5 mmol) were added. The reaction system was stirred for 12 hours at 120° C. After the reaction was completed, excess water was added, and the mixture was extracted three times with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound methyl 3-bromo-5-(2,2-diethoxyethoxy)-2-methylbenzoate 4d (820 mg, yield 69%) as a light yellow oil.

Step 4

Methyl 6-bromo-5-methylbenzofuran-4-carboxylate

Methyl 3-bromo-5-(2,2-diethoxyethoxy)-2-methylbenzoate 4d (650 mg, 1.8 mmol) was dissolved in 10 mL of toluene, then 10 mL of a pre-prepared solution of polyphosphoric acid (10 g) in toluene was added. The mixture was stirred for 5 hours at 100° C. After the reaction was completed, the upper organic phase was decanted. The residue was added with water, and extracted with ethyl acetate. The organic phases were combined, washed with saturated sodium carbonate solution and saturated sodium chloride solution, dried over anhydrous sodium sulfate, and filtered. The filtrate was concentrated under reduced pressure, and the resulting residue was purified by thin-layer chromatography with elution system B to obtain the title compound methyl 6-bromo-5-methylbenzofuran-4-carboxylate 4e (220 mg, yield 45%) as a yellow solid.

Step 5

Methyl 5-methyl-6-((tetrahydro-2H-pyran-4-yl)amino)benzofuran-4-carboxylate

Methyl 6-bromo-5-methylbenzofuran-4-carboxylate 4e (250 mg, 0.93 mmol), tetrahydro-2H-pyran-4-amine (141 mg, 1.4 mmol), tris(dibenzylideneacetone)dipalladium (85 mg, 0.09 mmol), (±)-2,2'-bis(diphenylphosphino)-1,1'-binaphthalene (116 mg, 0.19 mmol) and cesium carbonate (909 mg, 2.79 mmol) were dissolved in 10 mL of toluene. The mixture was stirred for 12 hours at 100° C. After the reaction was completed, the mixture was filtered through a pad of celite, and the filter cake was washed with ethyl acetate. The organic phases were combined, dried over anhydrous sodium sulfate, and filtered. The filtrate was concentrated under reduced pressure, and the resulting residue was purified by thin-layer chromatography with elution system B to obtain the title compound methyl 5-methyl-6-

((tetrahydro-2H-pyran-4-yl)amino)benzofuran-4-carboxylate 4f (250 mg, yield 90%) as a yellow solid.

Step 6

Methyl 6-(ethyl(tetrahydro-2H-pyran-4-yl)amino)-5-methylbenzofuran-4-carboxylate Methyl 5-methyl-6-((tetrahydro-2H-pyran-4-yl)amino)benzofuran-4-carboxylate 4f (250 mg, 0.87 mmol) was dissolved in 10 mL of 1,2-dichloroethane, then acetaldehyde (190 mg, 4.3 mmol) and acetic acid (260 mg, 4.3 mmol) were added. The mixture was stirred for 1 hour, then sodium triacetoxyborohydride (545 mg, 2.6 mmol) was added. The mixture was stirred for 12 hours at room temperature. After the reaction was completed, the reaction solution was concentrated under reduced pressure. Ethyl acetate and saturated sodium bicarbonate solution were added. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound methyl 6-(ethyl(tetrahydro-2H-pyran-4-yl)amino)-5-methylbenzofuran-4-carboxylate 4g (180 mg, yield 56%) as a yellow oil.

MS m/z (LC-MS): 318.2[M+1]

Step 7

Methyl 6-(ethyl(tetrahydro-2H-pyran-4-yl)amino)-2-formyl-5-methylbenzofuran-4-carboxylate Methyl 6-(ethyl(tetrahydro-2H-pyran-4-yl)amino)-5-methylbenzofuran-4-carboxylate 4g (180 mg, 0.57 mmol) was dissolved in 5 mL of tetrahydrofuran. The mixture was cooled down to −70° C., and 2.0 M lithium diisopropylamide (0.57 mL, 1.14 mmol) was added dropwise under an argon atmosphere. At −70° C., the mixture was stirred for 1 hour, then 4-formylmorpholine (98 mg, 0.85 mmol) was added. The mixture was stirred for 1 hour, then slowly warmed up to room temperature, and ammonium chloride solution was added. The mixture was stirred for 20 minutes, and extracted three times with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound methyl 6-(ethyl(tetrahydro-2H-pyran-4-yl)amino)-2-formyl-5-methylbenzofuran-4-carboxylate 4h (130 mg, yield 66%) as a yellow oil.

Step 8

Methyl 6-(ethyl(tetrahydro-2H-pyran-4-yl)amino)-2-(hydroxymethyl)-5-methylbenzofuran-4-carboxylate Methyl 6-(ethyl(tetrahydro-2H-pyran-4-yl)amino)-2-formyl-5-methylbenzofuran-4-carboxylate 4h (130 mg, 0.38 mmol) was dissolved in 1 mL of tetrahydrofuran and 5 mL of methanol, then sodium borohydride (22 mg, 0.57 mmol) was added in batches. The reaction mixture was stirred for 1 hour at room temperature. After the reaction was completed, the reaction solution was concentrated under reduced pressure. Saturated sodium bicarbonate solution was added, and the mixture was extracted three times with ethyl acetate. The organic phases were combined, washed with saturated sodium chloride solution, dried over anhydrous sodium sulfate, and filtered. The filtrate was concentrated under reduced pressure to obtain the crude title compound methyl 6-(ethyl(tetrahydro-2H-pyran-4-yl)amino)-2-(hydroxymethyl)-5-methylbenzofuran-4-carboxylate 4i (120 mg) as a yellow oil, which was directly used in the next step without further purification.

MS m/z (LC-MS): 348.0 [M+1]

Step 9

Methyl 2-(bromomethyl)-6-(ethyl(tetrahydro-2H-pyran-4-yl)amino)-5-methylbenzofuran-4-carboxylate The crude methyl 6-(ethyl(tetrahydro-2H-pyran-4-yl)amino)-2-(hydroxymethyl)-5-methylbenzofuran-4-carboxylate 4i (130 mg, 0.36 mmol) was dissolved in 5 mL of tetrahydrofuran, then phosphorus tribromide (146 mg, 0.54 mmol) was added dropwise. The mixture was stirred for 12 hours at room temperature. After the reaction was completed, water was added, and the mixture was extracted three times with ethyl acetate. The organic phases were combined, washed with saturated sodium bicarbonate solution and saturated sodium chloride solution, dried over anhydrous sodium sulfate, and filtered. The filtrate was concentrated under reduced pressure to obtain the crude title compound methyl 2-(bromomethyl)-6-(ethyl(tetrahydro-2H-pyran-4-yl)amino)-5-methylbenzofuran-4-carboxylate 4j (152 mg) as a yellow oil, which was directly used in the next step without further purification.

Step 10

Methyl 6-(ethyl(tetrahydro-2H-pyran-4-yl)amino)-5-methyl-2-(piperidin-1-ylmethyl)benzofuran-4-carboxylate The crude methyl 2-(bromomethyl)-6-(ethyl(tetrahydro-2H-pyran-4-yl)amino)-5-methylbenzofuran-4-carboxylate 4j (140 mg, 0.33 mmol) was dissolved in 5 mL of acetonitrile, then 5 mL of a pre-prepared solution of piperidine (56 mg, 0.66 mmol) in acetonitrile was added dropwise. The mixture was stirred for 1 hour at room temperature. After the reaction was completed, the reaction solution was concentrated under reduced pressure, then ethyl acetate and saturated sodium bicarbonate solution were added. Two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound methyl 6-(ethyl(tetrahydro-2H-pyran-4-yl)amino)-5-methyl-2-(piperidin-1-ylmethyl)benzofuran-4-carboxylate 4k (120 mg, yield 86%) as a colorless oil.

Step 11

6-(Ethyl(tetrahydro-2H-pyran-4-yl)amino)-5-methyl-2-(piperidin-1-ylmethyl)benzofuran-4-carboxylic acid Methyl 6-(ethyl(tetrahydro-2H-pyran-4-yl)amino)-5-methyl-2-(piperidin-1-ylmethyl)benzofuran-4-carboxylate 4k (120 mg, 0.29 mmol) was dissolved in 10 mL of methanol, then 3 mL of 4M sodium hydroxide solution was added. The mixture was stirred for 12 hours at 60° C. After the reaction was completed, concentrated hydrochloric acid was added to adjust the pH of the reaction solution to 4. The mixture was concentrated under reduced pressure, and the residue was dissolved in a mixture of dichloromethane and methanol (V:V=5:1) and filtered. The filter cake was washed with a mixture of dichoromethane and methanol (V:V=5:1). The filtrate was combined, and concentrated under reduced pressure to obtain the crude title compound 6-(ethyl(tetrahydro-2H-pyran-4-yl)amino)-5-methyl-2-(piperidin-1-ylmethyl)benzofuran-4-carboxylic acid 4i (120 mg) as a yellow solid, which was used directly in the next step without further purification.

MS m/z (LC-MS): 399.0[M+1]

Step 12

6-(Ethyl(tetrahydro-2H-pyran-4-yl)amino)-N-((4-methoxy-6-methyl-2-oxo-1,2-dihydro pyridin-3-yl)methyl)-5-methyl-2-(piperidin-1-ylmethyl)benzofuran-4-carboxamide The crude 6-(ethyl(tetrahydro-2H-pyran-4-yl)amino)-5-methyl-2-(piperidin-1-ylmethyl)benzofuran-4-carboxylic acid 4i (40 mg, 0.1 mmol) was dissolved in 3 mL of N,N-dimethylformamide, then 1-ethyl-3-(3-dimethylaminopropyl)carbodiimide (29 mg, 0.15 mmol), 1-hydroxybenzotriazole (20 mg, 0.15 mmol) and N,N-diisopropylethylamine (63 mg, 0.48 mmol) were added. The mixture was stirred for 16 hours, then 3-(aminomethyl)-4-methoxy-6-methylpyridin-2(1H)-one hydrochloride 1o (26 mg, 0.13 mmol) was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 6-(ethyl(tetrahydro-2H-pyran-4-yl)amino)-N-((4-methoxy-6-methyl-2-oxo-1,2-dihydropyridin-3-yl)methyl)-5-methyl-2-(piperidin-1-ylmethyl)benzofuran-4-carboxamide 4 (35 mg, yield 64%) as a white solid.

MS m/z (ESI): 551.7 [M+1]

$^1$H NMR (400 MHz, DMSO-d$_6$) δ 11.45 (s, 1H), 8.01 (s, 1H), 7.40 (s, 1H), 6.91 (brs, 1H), 6.12 (s, 1H), 4.30 (d, 2H), 3.84 (brs, 5H), 3.23 (t, 2H), 3.04-3.09 (m, 2H), 2.95-3.01 (m, 1H), 2.62 (s, 3H), 2.19 (s, 3H), 1.64-1.81 (brd, 6H), 1.50-1.55 (m, 4H), 1.38 (brs, 2H), 0.81 (t, 3H).

Example 5

5-Ethyl-6-(ethyl(tetrahydro-2H-pyran-4-yl)amino)-2-((4-isopropylpiperazin-1-yl)methyl)-N-((4-methoxy-6-methyl-2-oxo-1,2-dihydropyridin-3-yl)methyl)benzofuran-4-carboxamide

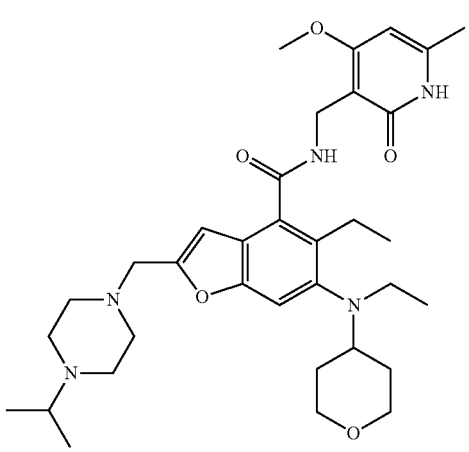

5

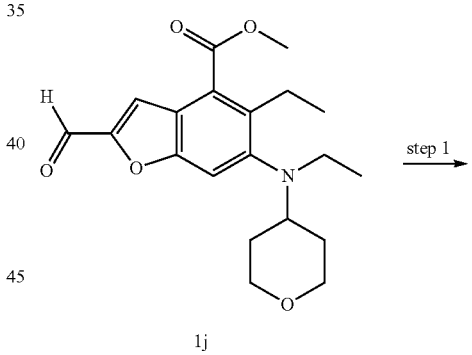

1j

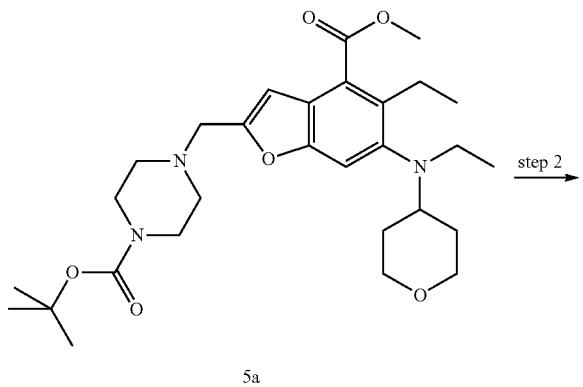

5a

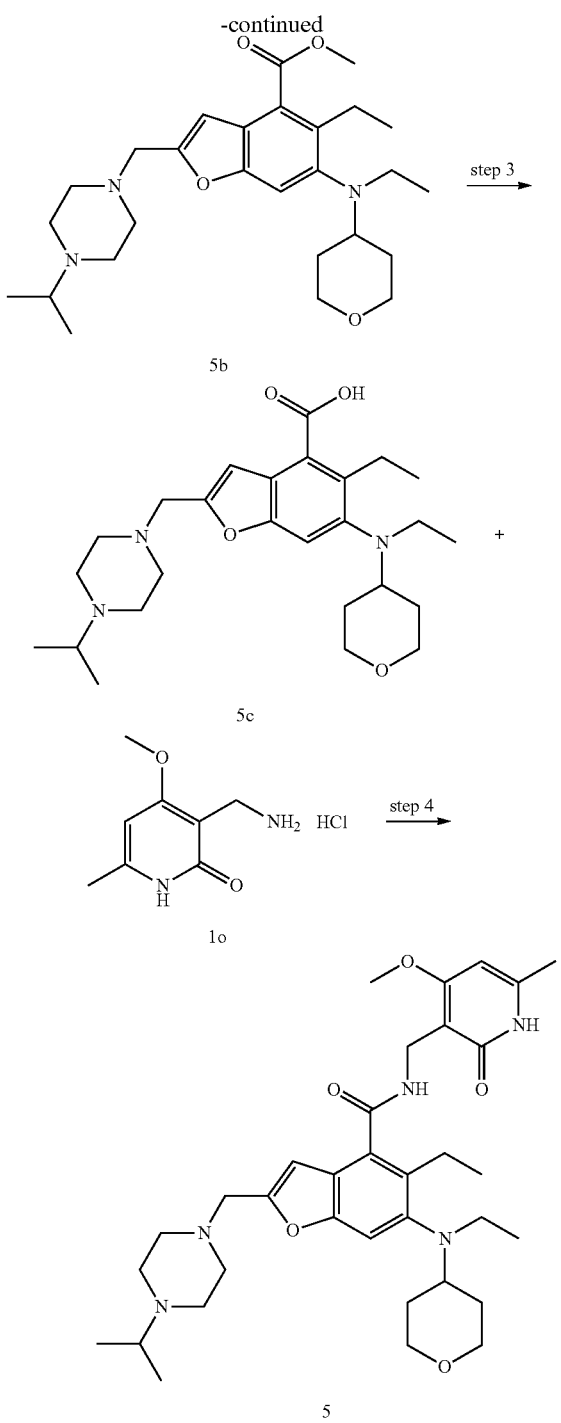

Step 1 tert-Butyl 4-((5-ethyl-6-(ethyl(tetrahydro-2H-pyran-4-yl)amino)-4-(methoxycarbonyl)benzofuran-2-yl)methyl)piperazine-1-carboxylate Methyl 5-ethyl-6-(ethyl(tetrahydro-2H-pyran-4-yl)amino)-2-formylbenzofuran-4-carboxylate 1j (30 mg, 0.083 mmol), 1-(tert-butoxycarbonyl)piperazine (24 mg, 0.13 mmol) and acetic acid (25 mg, 0.42 mmol) were added to 5 mL of methanol. The mixture was stirred for 1 hour, then sodium triacetoxyborohydride (53 mg, 0.25 mmol) was added. The mixture was stirred for 12 hours. After the reaction was completed, the reaction solution was concentrated under reduced pressure, neutralized with saturated sodium bicarbonate solution, extracted three times with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound tert-butyl 4-((5-ethyl-6-(ethyl(tetrahydro-2H-pyran-4-yl)amino)-4-(methoxycarbonyl)benzofuran-2-yl)methyl)piperazine-1-carboxylate 5a (40 mg, yield 90%) as a yellow oil.

MS m/z (LC-MS): 530.3 [M+1]

Step 2

Methyl 5-ethyl-6-(ethyl(tetrahydro-2H-pyran-4-yl)amino)-2-((4-isopropylpiperazin-1-yl)methyl)benzofuran-4-carboxylate tert-Butyl 4-((5-ethyl-6-(ethyl(tetrahydro-2H-pyran-4-yl)amino)-4-(methoxycarbonyl)benzofuran-2-yl)methyl)piperazine-1-carboxylate 5a (40 mg, 0.075 mmol) was added to 10 mL of trifluoroacetic acid. The mixture was stirred for 1 hour at room temperature, then concentrated under reduced pressure. Then, 5 mL of N,N-dimethylformamide and potassium carbonate (21 mg, 0.15 mmol) were added to the residue, and the mixture was stirred for 30 minutes. Then, 1-iodopropane (20 mg, 0.11 mmol) was added, and the reaction system was stirred for 1 hour at 70° C. After the reaction was completed, the reaction solution was poured into excess water, and extracted three times with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound methyl 5-ethyl-6-(ethyl(tetrahydro-2H-pyran-4-yl)amino)-2-((4-isopropylpiperazin-1-yl)methyl)benzofuran-4-carboxylate 5b (25 mg, yield 70%) as a colorless oil.

MS m/z (LC-MS): 472.3 [M+1]

Step 3

5-Ethyl-6-(ethyl(tetrahydro-2H-pyran-4-yl)amino)-2-((4-isopropylpiperazin-1-yl)methyl)benzofuran-4-carboxylic acid Methyl 5-ethyl-6-(ethyl(tetrahydro-2H-pyran-4-yl)amino)-2-((4-isopropylpiperazin-1-yl)methyl)benzofuran-4-carboxylate 5b (10 mg, 0.021 mmol) was dissolved in 3 mL of methanol and 1 mL of tetrahydrofuran, then 13 mL of 2M sodium hydroxide solution was added. The reaction system was stirred for 12 hours at 60° C. After the reaction was completed, the reaction solution was neutralized with concentrated sulfuric acid, then concentrated under reduced pressure. The residue was dissolved in a mixture of dichloromethane and methanol (V:V=5:1) and filtered. The filter cake was washed with a mixture of dichloromethane and methanol (V:V=5:1). The filtrate was combined, and concentrated under reduced pressure to obtain the crude title compound 5-ethyl-6-(ethyl(tetrahydro-2H-pyran-4-yl)amino)-2-((4-isopropylpiperazin-1-yl)methyl)benzofuran- 4-carboxylic acid 5c (9 mg) as a white solid, which was used directly in the next step without further purification.

MS m/z (LC-MS): 458.4 [M+1]

Step 4

5-Ethyl-6-(ethyl(tetrahydro-2H-pyran-4-yl)amino)-2-((4-isopropylpiperazin-1-yl)methyl)-N-((4-methoxy-6-methyl-2-oxo-1,2-dihydropyridin-3-yl)methyl)benzofuran-4-carboxamide The crude 5-ethyl-6-(ethyl(tetrahydro-2H-pyran-4-yl)amino)-2-((4-isopropylpiperazin-1-yl)methyl)benzofuran-4-carboxylic acid 5c (10 mg, 0.022 mmol) was dissolved in 3 mL of N,N-dimethylformamide, then 1-ethyl-3-(3-dimethylaminopropyl)carbodiimide (7 mg, 0.033 mmol), 1-hydroxybenzotriazole (5 mg, 0.033 mmol) and N,N-diisopropylethylamine (6 mg, 0.044 mmol) were added. The mixture was stirred for 30 minutes, then 3-(aminomethyl)-4-methoxy-6-methylpyridin-2(1H)-one hydrochloride 1o (5.8 mg, 0.028) was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl(tetrahydro-2H-pyran-4-yl)amino)-2-((4-isopropylpiperazin-1-yl)methyl)-N-((4-methoxy-6-methyl-2-oxo-1,2-dihydropyridin-3-yl)methyl)benzofuran-4-carboxamide 5 (9 mg, yield 69%) as a white solid.

MS m/z (ESI): 608.6 [M+1]

$^1$H NMR (400 MHz, DMSO-$d_6$) δ 11.45 (s, 1H), 8.01 (s, 1H), 7.39 (s, 1H), 6.56 (brs, 1H), 6.11 (s, 1H), 4.29 (d, 2H), 3.85 (brs, 2H), 3.83 (s, 3H), 3.63 (brs, 3H), 3.22 (t, 2H), 3.03-3.07 (m, 2H), 2.93-2.99 (m, 2H), 2.79-2.82 (m, 2H), 2.34-2.68 (brs, 8H), 2.19 (s, 3H), 1.64-1.67 (brd, 2H), 1.50-1.52 (m, 2H), 1.24-1.26 (brd, 2H), 1.06 (t, 3H), 0.98 (brs, 6H), 0.83 (t, 3H).

Example 6

5-Ethyl-6-(ethyl(tetrahydro-2H-pyran-4-yl)amino)-N-((4-methoxy-6-methyl-2-oxo-1,2-dihydropyridin-3-yl)methyl)-2-(morpholinomethyl)benzofuran-4-carboxamide

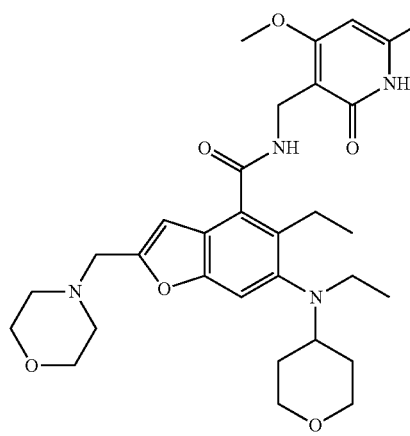

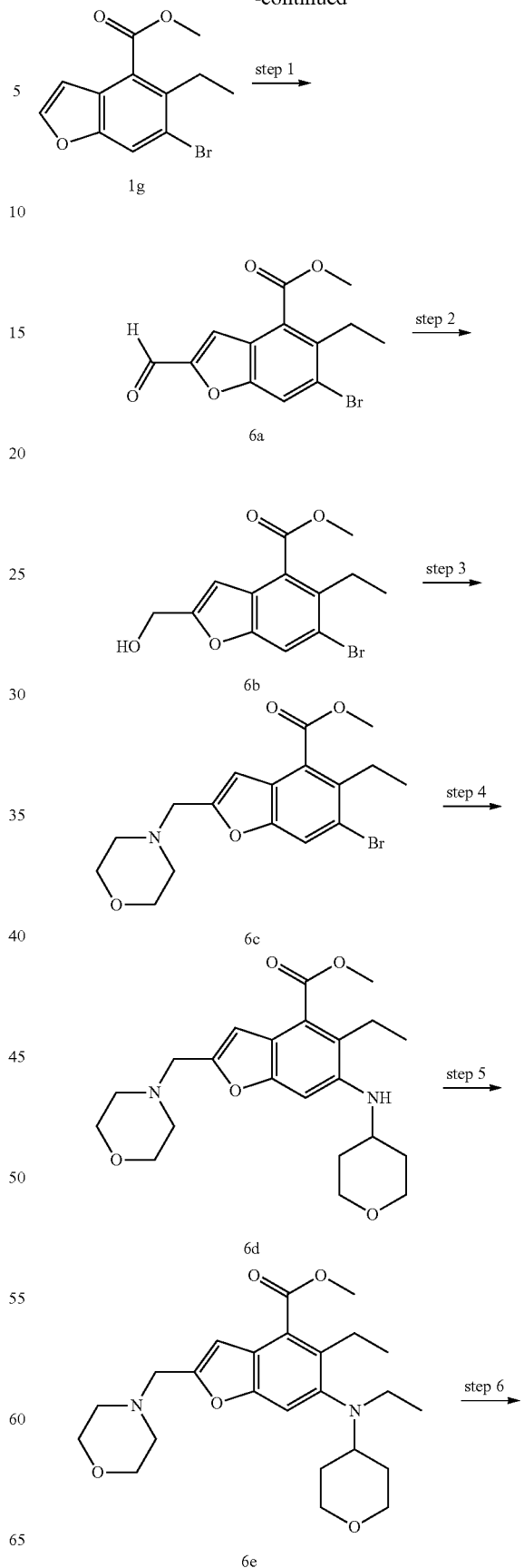

-continued

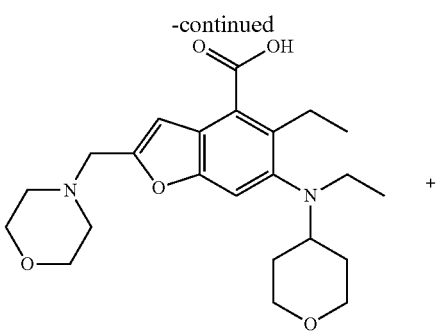

6f

+

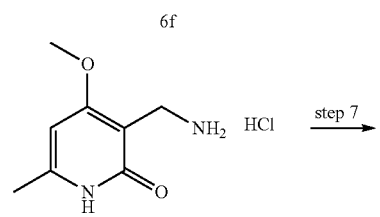

1o step 7 →

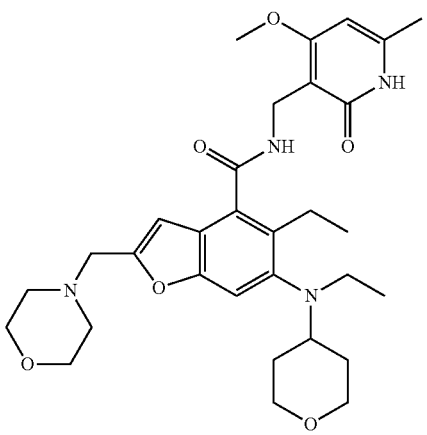

6

Step 1

Methyl 6-bromo-5-ethyl-2-formylbenzofuran-4-carboxylate

Methyl 6-bromo-5-ethylbenzofuran-4-carboxylate g (260 mg, 0.92 mmol) was dissolved in 8 mL of tetrahydrofuran. The mixture was cooled down to −70° C., then 2.0 M lithium diisopropylamide (0.92 mL, 1.84 mmol) was added dropwise under an argon atmosphere. At −70° C., the mixture was stirred for 1 hour, then 4-formylmorpholine (158 mg, 1.38 mmol) was added. The reaction was slowly warmed up to room temperature, and excess ammonium chloride was added. The mixture was stirred well, and extracted three times with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound methyl 6-bromo-5-ethyl-2-formylbenzofuran-4-carboxylate 6a (80 mg, yield 48%) as a yellow and white solid.

Step 2

Methyl 6-bromo-5-ethyl-2-(hydroxymethyl)benzofuran-4-carboxylate

Methyl 6-bromo-5-ethyl-2-formylbenzofuran-4-carboxylate 6a (80 mg, 0.26 mmol)) was dissolved in 4 mL of methanol and 0.5 mL of tetrahydrofuran, then sodium borohydride (20 mg, 0.51 mmol) was added in batches at room temperature. The mixture was stirred for 3 minutes. After the reaction was completed, ethyl acetate and saturated sodium bicarbonate solution were added. Two phases was separated, and the mixture was extracted three times with ethyl acetate. The organic phases were combined, washed with saturated sodium chloride solution, dried over anhydrous sodium sulfate, and filtered. The filtrate was concentrated under reduced pressure to obtain the crude title compound methyl 6-bromo-5-ethyl-2-(hydroxymethyl)benzofuran-4-carboxylate 6b (80 mg) as a white solid, which was directly used in the next step without further purification.

Step 3

Methyl 6-bromo-5-ethyl-2-(morpholinomethyl)benzofuran-4-carboxylate

The crude methyl 6-bromo-5-ethyl-2-(hydroxymethyl)benzofuran-4-carboxylate 6b (80 mg, 0.26 mmol) was dissolved in 5 mL of dichloromethane, then methanesulfonyl chloride (45 mg, 0.38 mmol) and trifluoroacetic acid (130 mg, 1.29 mmol) were added. The mixture was stirred for 12 hours. The mixture was concentrated under reduced pressure, then 5 mL of N,N-dimethylformamide, potassium carbonate (71 mg, 0.51 mmol) and morpholine (40 mg, 0.51 mmol) were added. The reaction system was stirred for 1 hour at 80° C. After the reaction was completed, water was added, and the mixture was extracted three times with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound methyl 6-bromo-5-ethyl-2-(morpholinomethyl)benzofuran-4-carboxylate 6c (65 mg, yield 64%) as a white solid.

MS m/z (ESI): 382.0 [M+1]

Step 4

Methyl 5-ethyl-2-(morpholinomethyl)-6-((tetrahydro-2H-pyran-4-yl)amino)benzofuran-4-carboxylate Methyl 6-bromo-5-ethyl-2-(morpholinomethyl)benzofuran-4-carboxylate 6c (90 mg, 0.24 mmol), tetrahydro-2H-pyran-4-amine (36 mg, 0.35 mmol), tris(dibenzylideneacetone)dipalladium (22 mg, 0.02 mmol), (±)-2,2'-bis(diphenylphosphino)-1,1'-binaphthalene (30 mg, 0.05 mmol) and cesium carbonate (230 mg, 0.71 mmol) were dissolved in 5 mL of toluene. The mixture was stirred for 12 hours at 100° C. After the reaction was completed, the mixture was filtered through a pad of celite. The filtrate was concentrated under reduced pressure, and the resulting residue was purified by thin-layer chromatography with elution system A to obtain the title compound methyl 5-ethyl-2-

(morpholinomethyl)-6-((tetrahydro-2H-pyran-4-yl)amino) benzofuran-4-carboxylate 6d (85 mg, yield 89%) as a white solid.

MS m/z (LC-MS): 401.2 [M+1]

Step 5

Methyl 5-ethyl-6-(ethyl(tetrahydro-2H-pyran-4-yl) amino)-2-(morpholinomethyl)benzofuran-4-carboxylate Methyl 5-ethyl-2-(morpholinomethyl)-6-((tetrahydro-2H-pyran-4-yl)amino) benzofuran-4-carboxylate 6d (85 mg, 0.21 mmol) was dissolved in 5 mL of 1,2-dichloroethane, then acetaldehyde (93 mg, 2.1 mmol) and acetic acid (63 mg, 1.06 mmo) were added. The mixture was stirred for 2 hours, then sodium triacetoxyborohydride (133 mg, 0.63 mmol) was added. The mixture was stirred for 12 hours at room temperature. After the reaction was completed, the reaction solution was concentrated under reduced pressure, neutralized with saturated sodium bicarbonate solution, and extracted with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound methyl 5-ethyl-6-(ethyl(tetrahydro-2H-pyran-4-yl)amino)-2-(morpholinomethyl)benzofuran-4-carboxylate 6e (75 mg, yield 82%) as a white solid.

MS m/z (LC-MS): 344.1 [M−86]

Step 6

5-Ethyl-6-(ethyl(tetrahydro-2H-pyran-4-yl)amino)-2-(morpholinomethyl)benzofuran-4-carboxylic acid Methyl 5-ethyl-6-(ethyl(tetrahydro-2H-pyran-4-yl) amino)-2-(morpholinomethyl) benzofuran-4-carboxylate 6e (75 mg, 0.17 mmol) was dissolved in 1 mL of tetrahydrofuran and 3 mL of methanol, then 3 mL of 4M sodium hydroxide solution was added. The mixture was stirred for 12 hours at 60° C. After the reaction was completed, concentrated hydrochloric acid was added to adjust the pH of the reaction solution to 4. The mixture was concentrated under reduced pressure. The residue was washed with methanol and filtered to remove a white solid. The filtrate was concentrated under reduced pressure to obtain the crude title compound 5-ethyl-6-(ethyl(tetrahydro-2H-pyran-4-yl) amino)-2-(morpholinomethyl)benzofuran-4-carboxylic acid 6f (71 mg) as a white solid, which was directly used in the next step without further purification.

Step 7

5-Ethyl-6-(ethyl(tetrahydro-2H-pyran-4-yl)amino)-N-((4-methoxy-6-methyl-2-oxo-1,2-dihydropyridin-3-yl)methyl)-2-(morpholinomethyl)benzofuran-4-carboxamide The crude 5-ethyl-6-(ethyl(tetrahydro-2H-pyran-4-yl) amino)-2-(morpholinomethyl)benzofuran-4-carboxylic acid 6f (45 mg, 0.11 mmol) was dissolved in 5 mL of N,N-dimethylformamide, then 1-ethyl-3-(3-dimethylaminopropyl)carbodiimide (31 mg, 0.16 mmol), 1-hydroxybenzotriazole (22 mg, 0.16 mmol) and N,N-diisopropylethylamine (70 mg, 0.54 mmol) were added. The mixture was stirred for 1 hour, then 3-(aminomethyl)-4-methoxy-6-methylpyridin-2(1H)-one hydrochloride 1o (33 mg, 0.16 mmol) was added. The mixture was stirred for 36 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl(tetrahydro-2H-pyran-4-yl)amino)-N-((4-methoxy-6-methyl-2-oxo-1,2-dihydropyridin-3-yl)methyl)-2-(morpholinomethyl)benzofuran-4-carboxamide 6 (35 mg, yield 57%) as a white solid.

MS m/z (ESI): 567.4 [M+1]

$^1$H NMR (400 MHz, DMSO-$d_6$) δ 11.43 (s, 1H), 7.99 (t, 1H), 7.39 (s, 1H), 6.54 (s, 1H), 6.10 (s, 1H), 4.28 (d, 2H), 3.84 (brs, 2H), 3.82 (s, 3H), 3.59 (s, 2H), 3.55-3.57 (m, 4H), 3.21 (t, 2H), 3.02-3.07 (m, 2H), 2.92-2.97 (m, 1H), 2.78-2.83 (m, 2H), 2.43 (brs, 4H), 2.18 (s, 3H), 1.64-1.67 (brd, 2H), 1.45-1.55 (m, 2H), 1.05 (t, 3H), 0.82 (t, 3H).

Example 7

2-((4,4-Difluoropiperidin-1-yl)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide

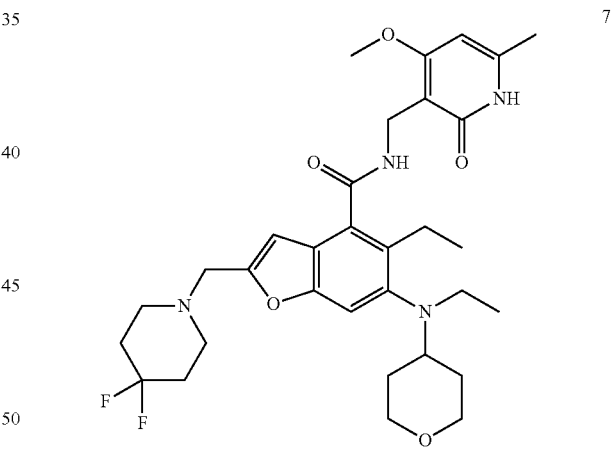

7

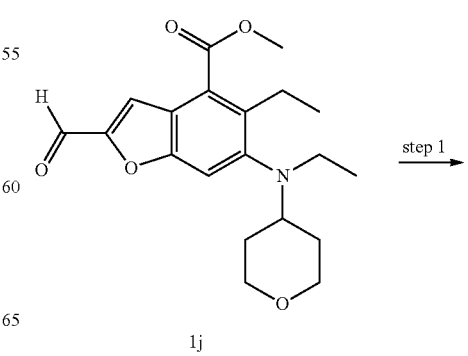

1j step 1

-continued

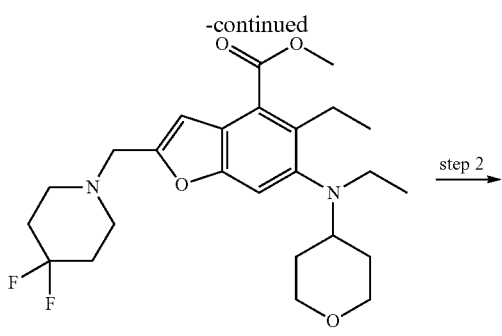

7a

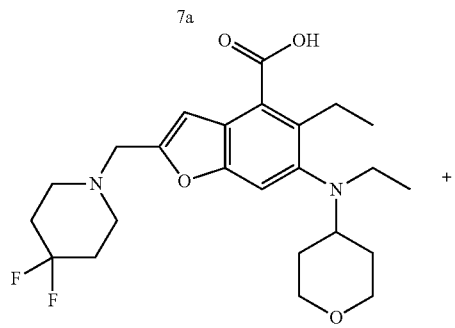

7b lo

7

Step 1

Methyl 2-((4,4-difluoropiperidin-1-yl)methyl)-5-ethyl-6-(ethyl(tetrahydro-2H-pyran-4-yl)amino)benzofuran-4-carboxylate Methyl 5-ethyl-6-(ethyl(tetrahydro-2H-pyran-4-yl)amino)-2-formylbenzofuran-4-carboxylate 1j (50 mg, 0.14 mmol), 4,4-difluoropiperidine hydrochloride (33 mg, 0.21 mmol) and acetic acid (42 mg, 0.49 mmol) were added to 5 mL of methanol. The mixture was stirred 1 hour, then molecular sieves and sodium triacetoxyborohydride (88 mg, 0.42 mmol) were added. The mixture was stirred for 12 hours at room temperature. After the reaction was completed, the mixture was neutralized with saturated sodium bicarbonate solution, and extracted with a mixture of dichloromethane and methanol (V:V=5:1). The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound methyl 2-((4,4-difluoropiperidin-1-yl)methyl)-5-ethyl-6-(ethyl(tetrahydro-2H-pyran-4-yl)amino)benzofuran-4-carboxylate 7a (25 mg, yield 45%) as a colorless oil.

MS m/z (ESI): 465.1[M+1]

Step 2

2-((4,4-Difluoropiperidin-1-yl)methyl)-5-ethyl-6-(ethyl(tetrahydro-2H-pyran-4-yl)amino)benzofuran-4-carboxylic acid Methyl 2-((4,4-difluoropiperidin-1-yl)methyl)-5-ethyl-6-(ethyl(tetrahydro-2H-pyran-4-yl)amino)benzofuran-4-carboxylate 7a (20 mg, 0.043 mmol) was dissolved in 1 mL of tetrahydrofuran and 3 mL of methanol, then 3 mL of 4M sodium hydroxide solution was added. The mixture was stirred for 12 hours at 60° C. After the reaction was completed, the reaction solution was neutralized with concentrated hydrochloric acid, then concentrated under reduced pressure. The residue was dissolved in a mixture of dichloromethane and methanol (V:V=5:1) and filtered. The filter cake was washed with a mixture of dichoromethane and methanol (V:V=5:1). The filtrate was combined, and concentrated under reduced pressure to obtain the crude title compound 2-((4,4-difluoropiperidin-1-yl)methyl)-5-ethyl-6-(ethyl(tetrahydro-2H-pyran-4-yl)amino)benzofuran-4-carboxylic acid 7b (20 mg) as a white solid, which was directly used in the next step without further purification.

Step 3

2-((4,4-Difluoropiperidin-1-yl)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide The crude 2-((4,4-difluoropiperidin-1-yl)methyl)-5-ethyl-6-(ethyl(tetrahydro-2H-pyran-4-yl)amino)benzofuran-4-carboxylic acid 7b (20 mg, 0.044 mmol) was dissolved in 5 mL of N,N-dimethylformamide, then 1-ethyl-3-(3-dimethylaminopropyl)carbodiimide (13 mg, 0.066), 1-hydroxybenzotriazole (9 mg, 0.066 mmol) and N,N-diisopropylethylamine (29 mg, 0.22 mmol) were added. The mixture was stirred 1 hour, then 3-(aminomethyl)-4-methoxy-6-methylpyridin-2(1H)-one hydrochloride 1o (12 mg, 0.058 mmol) was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 2-((4,4-difluoropiperidin-1-yl)methyl)-5-ethyl-6-(ethyl(tetrahydro-2H-pyran-4-yl)amino)-

N-((4-methoxy-6-methyl-2-oxo-1,2-dihydropyridin-3-yl)methyl)benzofuran-4-carboxamide 7 (21 mg, yield 78%) as a white solid.

MS m/z (ESI): 601.5 [M+1]

$^1$H NMR (400 MHz, DMSO-d$_6$) δ 11.43 (s, 1H), 8.00 (t, 1H), 7.39 (s, 1H), 6.55 (s, 1H), 6.10 (s, 1H), 4.28 (d, 2H), 3.84 (brs, 2H), 3.82 (s, 3H), 3.69 (s, 2H), 3.21 (t, 2H), 3.02-3.07 (m, 2H), 2.92-2.98 (m, 1H), 2.78-2.83 (m, 2H), 2.57 (brs, 4H), 2.17 (s, 3H), 1.95-1.98 (m, 4H), 1.64-1.66 (brd, 2H), 1.46-1.55 (m, 2H), 1.05 (t, 3H), 0.82 (t, 3H).

Example 8

5-Ethyl-6-(ethyl(tetrahydro-2H-pyran-4-yl)amino)-N-((4-methoxy-6-methyl-2-oxo-1,2-dihydropyridin-3-yl)methyl)-2-(pyrrolidin-1-ylmethyl)benzofuran-4-carboxamide

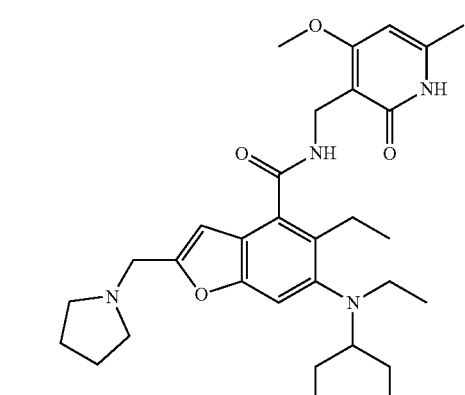

8

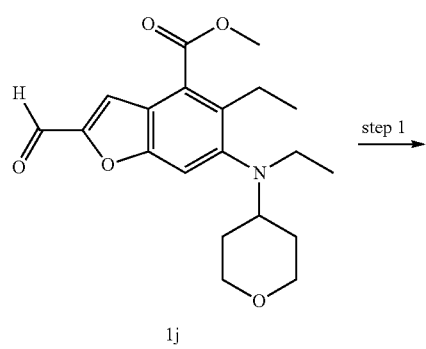

1j

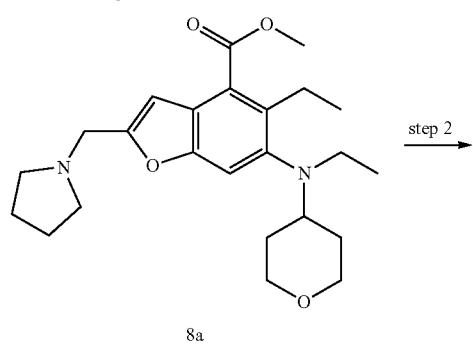

8a

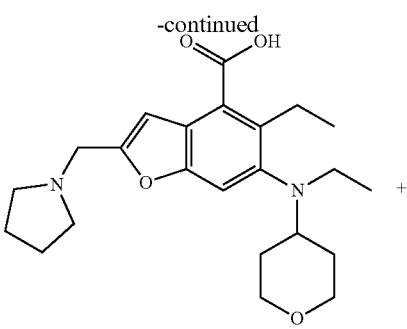

8b

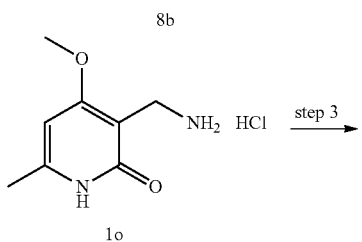

1o

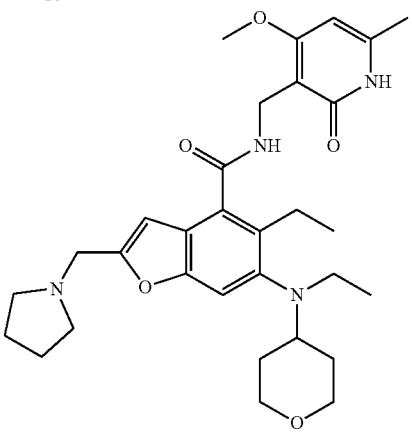

8

Step 1

Methyl 5-ethyl-6-(ethyl(tetrahydro-2H-pyran-4-yl)amino)-2-(pyrrolidin-1-ylmethyl)benzofuran-4-carboxylate Methyl 5-ethyl-6-(ethyl(tetrahydro-2H-pyran-4-yl)amino)-2-formylbenzofuran-4-carboxylate 1j (40 mg, 0.11 mmol), pyrrolidine (15 mg, 0.22 mmol) and acetic acid (30 mg, 0.55 mmol) were dissolved in 5 mL of methanol. The mixture was stirred 1 hour, then sodium triacetoxyborohydride (70 mg, 0.33 mmol) was added. The mixture was stirred for 12 hours at room temperature. After the reaction was completed, the mixture was neutralized with saturated sodium bicarbonate solution, and extracted with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound methyl 5-ethyl-6-(ethyl(tetrahydro-2H-pyran-4-yl)amino)-2-(pyrrolidin-1-ylmethyl)benzofuran-4-carboxylate 8a (44 mg, yield 95%) as a colorless oil.

Step 2

5-Ethyl-6-(ethyl(tetrahydro-2H-pyran-4-yl)amino)-2-(pyrrolidin-1-ylmethyl)benzofuran-4-carboxylic acid Methyl 5-ethyl-6-(ethyl(tetrahydro-2H-pyran-4-yl)amino)-2-(pyrrolidin-1-ylmethyl)benzofuran-4-carboxylate 8a (56 mg, 0.13 mmol) was dissolved in 1 mL of tetrahydrofuran and 5 mL of methanol, then 2 mL of 4M sodium hydroxide solution were added. The mixture was stirred for 12 hours at 60° C. After the reaction was completed, concentrated hydrochloric acid was added to adjust the pH to 4, then the mixture was concentrated under reduced pressure. The residue was dissolved in a mixture of dichloromethane and methanol (V:V=5:1) and filtered. The filter cake was washed with a mixture of dichoromethane and methanol (V:V=5:1). The filtrate was combined, and concentrated under reduced pressure to obtain the crude title compound 5-ethyl-6-(ethyl(tetrahydro-2H-pyran-4-yl)amino)-2-(pyrrolidin-1-ylmethyl)benzofuran-4-carboxylic acid 8b (50 mg) as a white solid, which was directly used in the next step without further purification.

MS m/z (ESI): 399.0 [M−1]

Step 3

5-Ethyl-6-(ethyl(tetrahydro-2H-pyran-4-yl)amino)-N-((4-methoxy-6-methyl-2-oxo-1,2-dihydropyridin-3-yl)methyl)-2-(pyrrolidin-1-ylmethyl)benzofuran-4-carboxamide The crude 5-ethyl-6-(ethyl(tetrahydro-2H-pyran-4-yl)amino)-2-(pyrrolidin-1-ylmethyl)benzofuran-4-carboxylic acid 8b (25 mg, 0.60 mmol) was dissolved in 3 mL of N,N-dimethylformamide, then 1-ethyl-3-(3-dimethylaminopropyl)carbodiimide (15 mg, 0.09 mmol), 1-hydroxybenzotriazole (12 mg, 0.09 mmol) and N,N-diisopropylethylamine (387 mg, 3.0 mmol) were added. The mixture was stirred 1 hour, then 3-(aminomethyl)-4-methoxy-6-methylpyridin-2(1H)-one hydrochloride 1o (16 mg, 0.078 mmol) was added. The mixture was stirred for 12 hours at room temperature. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl(tetrahydro-2H-pyran-4-yl)amino)-N-((4-methoxy-6-methyl-2-oxo-1,2-dihydropyridin-3-yl)methyl)-2-(pyrrolidin-1-ylmethyl)benzofuran-4-carboxamide 8 (12 mg, yield 36%) as a white solid.

MS m/z (ESI): 551.6 [M+1]

$^1$H NMR (400 MHz, DMSO-d$_6$) δ 11.43 (s, 1H), 7.99 (t, 1H), 7.37 (s, 1H), 6.50 (s, 1H), 6.10 (s, 1H), 4.28 (d, 2H), 3.84 (brs, 2H), 3.82 (s, 3H), 3.71 (brs, 2H), 3.18-3.26 (m, 4H), 3.03-3.07 (m, 2H), 2.92-2.97 (m, 1H), 2.78-2.81 (m, 2H), 2.17 (s, 3H), 1.70 (brs, 4H), 1.64 (brs, 2H), 1.46-1.54 (m, 2H), 1.23 (brs, 2H), 1.05 (t, 3H), 0.82 (t, 3H).

Example 9

N-((4,6-Dimethyl-2-oxo-1,2-dihydropyridin-3-yl)methyl)-5-ethyl-6-(ethyl(tetrahydro-2H-pyran-4-yl)amino)-2-(1-isopropylpiperidin-4-yl)benzofuran-4-carboxamide

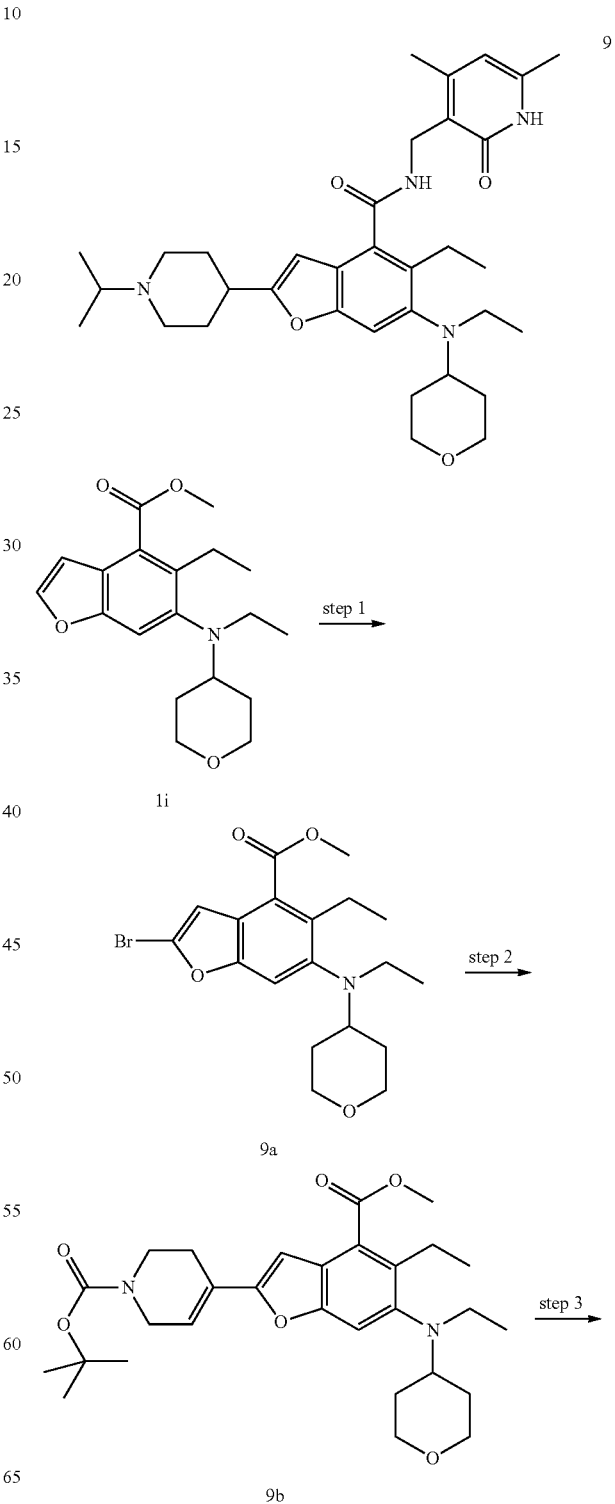

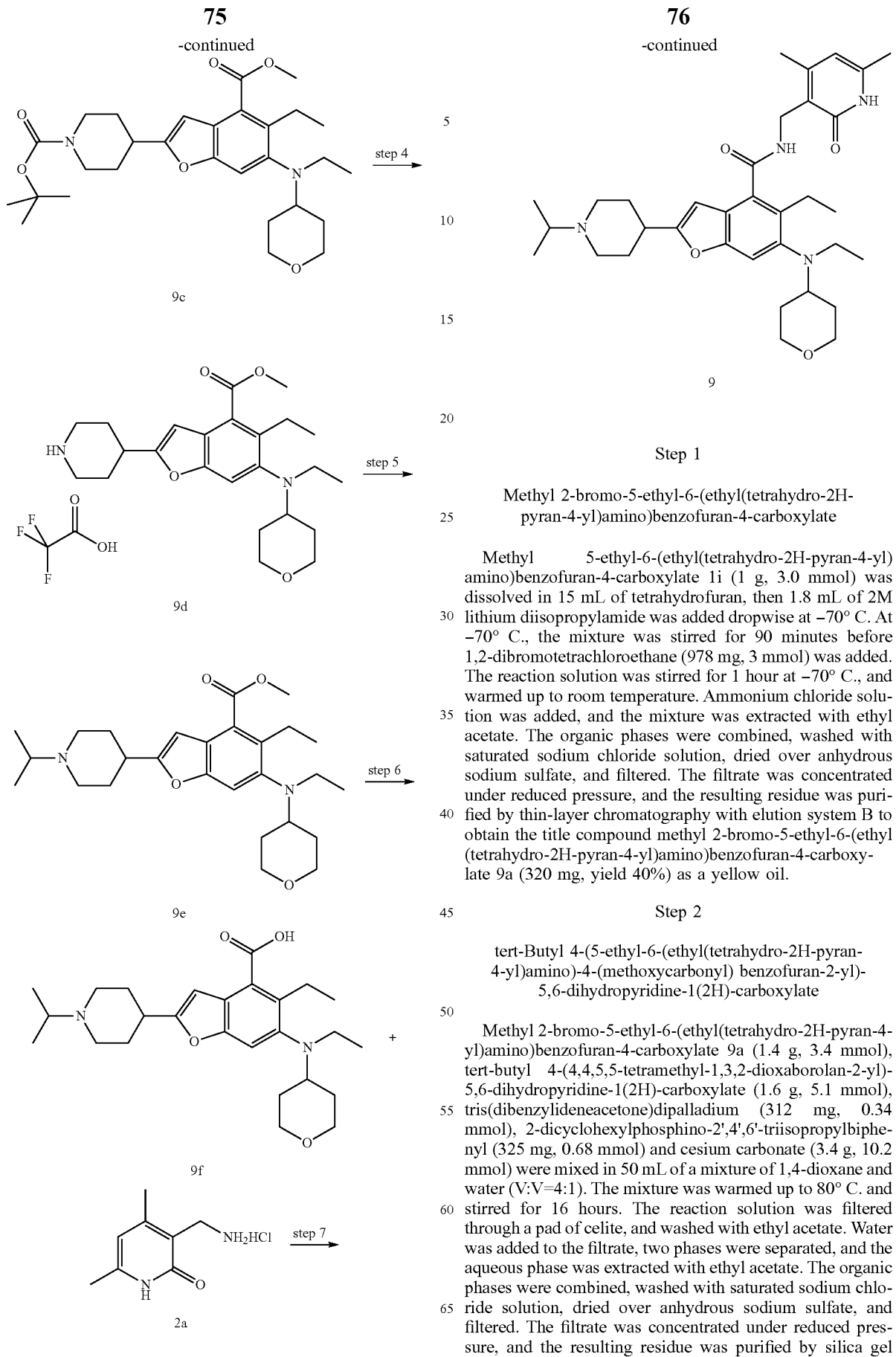

Step 1

Methyl 2-bromo-5-ethyl-6-(ethyl(tetrahydro-2H-pyran-4-yl)amino)benzofuran-4-carboxylate Methyl 5-ethyl-6-(ethyl(tetrahydro-2H-pyran-4-yl)amino)benzofuran-4-carboxylate 1i (1 g, 3.0 mmol) was dissolved in 15 mL of tetrahydrofuran, then 1.8 mL of 2M lithium diisopropylamide was added dropwise at −70° C. At −70° C., the mixture was stirred for 90 minutes before 1,2-dibromotetrachloroethane (978 mg, 3 mmol) was added. The reaction solution was stirred for 1 hour at −70° C., and warmed up to room temperature. Ammonium chloride solution was added, and the mixture was extracted with ethyl acetate. The organic phases were combined, washed with saturated sodium chloride solution, dried over anhydrous sodium sulfate, and filtered. The filtrate was concentrated under reduced pressure, and the resulting residue was purified by thin-layer chromatography with elution system B to obtain the title compound methyl 2-bromo-5-ethyl-6-(ethyl(tetrahydro-2H-pyran-4-yl)amino)benzofuran-4-carboxylate 9a (320 mg, yield 40%) as a yellow oil.

Step 2 tert-Butyl 4-(5-ethyl-6-(ethyl(tetrahydro-2H-pyran-4-yl)amino)-4-(methoxycarbonyl) benzofuran-2-yl)-5,6-dihydropyridine-1(2H)-carboxylate Methyl 2-bromo-5-ethyl-6-(ethyl(tetrahydro-2H-pyran-4-yl)amino)benzofuran-4-carboxylate 9a (1.4 g, 3.4 mmol), tert-butyl 4-(4,4,5,5-tetramethyl-1,3,2-dioxaborolan-2-yl)-5,6-dihydropyridine-1(2H)-carboxylate (1.6 g, 5.1 mmol), tris(dibenzylideneacetone)dipalladium (312 mg, 0.34 mmol), 2-dicyclohexylphosphino-2',4',6'-triisopropylbiphenyl (325 mg, 0.68 mmol) and cesium carbonate (3.4 g, 10.2 mmol) were mixed in 50 mL of a mixture of 1,4-dioxane and water (V:V=4:1). The mixture was warmed up to 80° C. and stirred for 16 hours. The reaction solution was filtered through a pad of celite, and washed with ethyl acetate. Water was added to the filtrate, two phases were separated, and the aqueous phase was extracted with ethyl acetate. The organic phases were combined, washed with saturated sodium chloride solution, dried over anhydrous sodium sulfate, and filtered. The filtrate was concentrated under reduced pressure, and the resulting residue was purified by silica gel column chromatography with elution system B to obtain the title compound tert-butyl 4-(5-ethyl-6-(ethyl(tetrahydro-2H-pyran-4-yl)amino)-4-(methoxycarbonyl) benzofuran-2-yl)-5,6-dihydropyridine-1(2H)-carboxylate 9b (1.67 g, yield 95%) as a purple oil.

Step 3 tert-Butyl 4-(5-ethyl-6-(ethyl(tetrahydro-2H-pyran-4-yl)amino)-4-(methoxycarbonyl)benzofuran-2-yl) piperidine-1-carboxylate tert-Butyl 4-(5-ethyl-6-(ethyl(tetrahydro-2H-pyran-4-yl)amino)-4-(methoxycarbonyl)benzofuran-2-yl)-5,6-dihydropyridine-1(2H)-carboxylate 9b (1.7 g, 3.3 mmol) was dissolved in 23 mL of a mixture of methanol and tetrahydrofuran (V:V=20:3), then Pd/C (200 mg, 10%) was added. The reaction system was purged three times with hydrogen and stirred for 1 hour. The reaction solution was filtered through a pad of celite. The filtrate was concentrated under reduced pressure, and the resulting residue was purified by silica gel column chromatography with elution system B to obtain the title compound tert-butyl 4-(5-ethyl-6-(ethyl(tetrahydro-2H-pyran-4-yl)amino)-4-(methoxycarbonyl)benzofuran-2-yl)piperidine-1-carboxylate 9c (1.6 g, yield 94%) as a light yellow oil. MS m/z (ESI): 515.0 [M+1]

Step 4

Methyl 5-ethyl-6-(ethyl(tetrahydro-2H-pyran-4-yl)amino)-2-(piperidin-4-yl)benzofuran-4-carboxylate 2,2,2-trifluoroacetate tert-Butyl 4-(5-ethyl-6-(ethyl(tetrahydro-2H-pyran-4-yl)amino)-4-(methoxycarbonyl)benzofuran-2-yl)piperidine-1-carboxylate 9c (1.6 g, 3.3 mmol) was dissolved in 20 mL of dichloromethane, then 4 mL of trifluoroacetic acid was added. The mixture was stirred for 2 hours, then concentrated under reduced pressure to obtain the crude title compound methyl 5-ethyl-6-(ethyl(tetrahydro-2H-pyran-4-yl)amino)-2-(piperidin-4-yl)benzofuran-4-carboxylate 2,2,2-trifluoroacetate 9d (1.3 g) as a light yellow oil, which was directly used in the next step without further purification.
MS m/z (ESI): 415.3 [M+1]

Step 5

Methyl 5-ethyl-6-(ethyl(tetrahydro-2H-pyran-4-yl)amino)-2-(1-isopropylpiperidin-4-yl)benzofuran-4-carboxylate The crude methyl 5-ethyl-6-(ethyl(tetrahydro-2H-pyran-4-yl)amino)-2-(piperidin-4-yl)benzofuran-4-carboxylate 2,2,2-trifluoroacetate 9d (1.3 g, 3.1 mmol) was dissolved in 30 mL of N,N-dimethylformamide, then potassium carbonate (1.3 g, 8.4 mmol) was added. The mixture was stirred for 10 minutes, then 2-bromopropane (575 mg, 4.7 mmol) and potassium iodide (261 mg, 1.5 mmol) were added. The mixture was stirred for 2 hours at 70° C., then water was added, and the reaction solution was extracted with a mixture of dichloromethane and methanol (V:V=5:1). The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound methyl 5-ethyl-6-(ethyl(tetrahydro-2H-pyran-4-yl)amino)-2-(1-isopropylpiperidin-4-yl)benzofuran-4-carboxylate 9e (1.4 g, yield 90%) as a colorless oil.
MS m/z (ESI): 457.0 [M+1]

Step 6

5-Ethyl-6-(ethyl(tetrahydro-2H-pyran-4-yl)amino)-2-(1-isopropylpiperidin-4-yl)benzofuran-4-carboxylic acid Methyl 5-ethyl-6-(ethyl(tetrahydro-2H-pyran-4-yl)amino)-2-(1-isopropylpiperidin-4-yl)benzofuran-4-carboxylate 9e (1.1 g, 2.4 mmol) was dissolved in 30 mL of methanol, then 5 mL of 4M sodium hydroxide solution was added. The mixture was stirred for 16 hours at 60° C., then concentrated hydrochloric acid was added to adjust the pH of the reaction solution to 4. The mixture was concentrated under reduced pressure, and the residue was dissolved in a mixture of dichloromethane and methanol (V:V=5:1) and filtered. The filter cake was washed with a mixture of dichloromethane and methanol (V:V=5:1). The filtrate was combined, and concentrated under reduced pressure to obtain the crude title compound 5-ethyl-6-(ethyl(tetrahydro-2H-pyran-4-yl)amino)-2-(1-isopropylpiperidin-4-yl)benzofuran-4-carboxylic acid 9f (1.4 g) as a white solid, which was used directly in the next step without further purification.
MS m/z (ESI): 443.3 [M+1]

Step 7

N-((4,6-Dimethyl-2-oxo-1,2-dihydropyridin-3-yl)methyl)-5-ethyl-6-(ethyl(tetrahydro-2H-pyran-4-yl)amino)-2-(1-isopropylpiperidin-4-yl)benzofuran-4-carboxamide The crude 5-ethyl-6-(ethyl(tetrahydro-2H-pyran-4-yl)amino)-2-(1-isopropylpiperidin-4-yl)benzofuran-4-carboxylic acid 9f (1.1 g, 2.5 mmol) was dissolved in 20 mL of N,N-dimethylformamide, then 1-ethyl-3-(3-dimethylaminopropyl)carbodiimide (715 mg, 3.7 mmol), 1-hydroxybenzotriazole (510 mg, 3.7 mmol) and N,N-diisopropylethylamine (1.6 g, 12.5 mmol) were added. The mixture was stirred for 1 hour, then 3-(aminomethyl)-4,6-dimethylpyridin-2(1H)-one hydrochloride 2a (470 mg, 2.5 mmol) was added. The mixture was stirred for 16 hours. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound N-((4,6-dimethyl-2-oxo-1,2-dihydropyridin-3-yl)methyl)-5-ethyl-6-(ethyl(tetrahydro-2H-pyran-4-yl)amino)-2-(1-isopropylpiperidin-4-yl)benzofuran-4-carboxamide 9 (850 mg, yield 59%) as a white solid.
MS m/z (ESI): 577.7 [M+1]
$^1$H NMR (400 MHz, DMSO-d$_6$) δ 11.50 (s, 1H), 8.16 (t, 1H), 7.38 (s, 1H), 6.37 (brs, 1H), 5.87 (s, 1H), 4.31 (d, 2H), 3.82 (d, 2H), 3.21 (t, 2H), 3.01-3.07 (m, 4H), 2.91-2.96 (m, 1H), 2.79-2.81 (m, 2H), 2.24 (s, 3H), 2.17 (brs, 2H), 2.12 (s, 3H), 2.02 (brs, 2H), 1.63-1.66 (brd, 2H), 1.45-1.54 (m, 2H), 1.25 (brs, 6H), 1.01 (t, 3H), 0.81 (t, 3H).

Example 10

5-Ethyl-6-(ethyl(tetrahydro-2H-pyran-4-yl)amino)-2-(1-isopropylpiperidin-4-yl)-N-((4-methoxy-6-methyl-2-oxo-1,2-dihydropyridin-3-yl)methyl)benzofuran-4-carboxamide

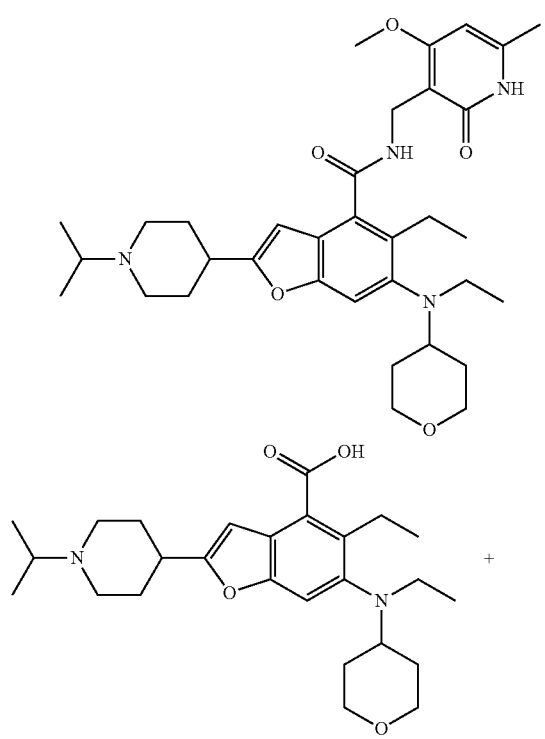

The crude 5-ethyl-6-(ethyl(tetrahydro-2H-pyran-4-yl)amino)-2-(1-isopropylpiperidin-4-yl)benzofuran-4-carboxylic acid 9f (30 mg, 0.07 mmol) was dissolved in 5 mL of N,N-dimethylformamide, then 1-ethyl-3-(3-dimethylaminopropyl)carbodiimide (20 mg, 0.1 mmol), 1-hydroxybenzotriazole (15 mg, 0.1 mmol) and N,N-diisopropylethylamine (45 mg, 0.34 mmol) were added. The mixture was stirred for 1 hour, then 3-(aminomethyl)-4-methoxy-6-methylpyridin-2(1H)-one hydrochloride 1o (21 mg, 0.1 mmol) was added. The mixture was stirred for 16 hours. After the reaction was completed, excess water was added, and the reaction solution was extracted with a mixture of dichloromethane and methanol (V:V=8:1). The organic phases were combined, washed with water and saturated sodium chloride solution, dried over anhydrous sodium sulfate, and filtered. The filtrate was concentrated under reduced pressure, and the resulting residue was purified by thin-layer chromatography with elution system A to obtain the title compound 5-ethyl-6-(ethyl(tetrahydro-2H-pyran-4-yl)amino)-2-(1-isopropylpiperidin-4-yl)-N-((4-methoxy-6-methyl-2-oxo-1,2-dihydropyridin-3-yl)methyl)benzofuran-4-carboxamide 10 (31 mg, yield 77%) as a white solid.

MS m/z (ESI): 593.3 [M+1]

$^1$H NMR (400 MHz, DMSO-$d_6$) δ 11.44 (s, 1H), 7.95 (brs, 1H), 7.36 (s, 1H), 6.37 (brs, 1H), 6.11 (s, 1H), 4.28 (d, 2H), 3.84 (brs, 2H), 3.82 (s, 3H), 3.21 (t, 3H), 3.01-3.06 (m, 3H), 2.90-2.96 (m, 2H), 2.77-2.83 (m, 3H), 2.19 (s, 3H), 2.01 (brs, 4H), 1.63-1.67 (brd, 2H), 1.45-1.53 (m, 2H), 1.22 (brs, 6H), 1.04 (t, 3H), 0.81 (t, 3H).

Example 11

N-((4,6-Dimethyl-2-oxo-1,2-dihydropyridin-3-yl)methyl)-5-ethyl-6-(ethyl(tetrahydro-2H-pyran-4-yl)amino)-2-((4-(2-hydroxy-2-methylpropyl)piperazin-1-yl)methyl)benzofuran-4-carboxamide 11

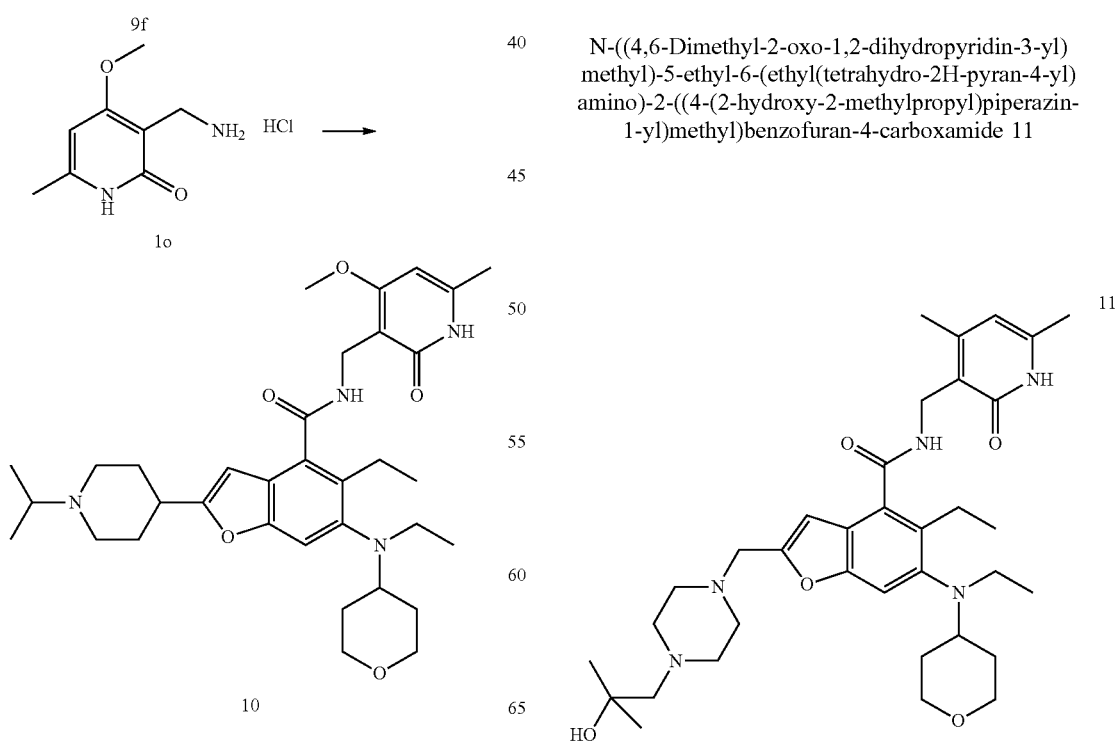

-continued

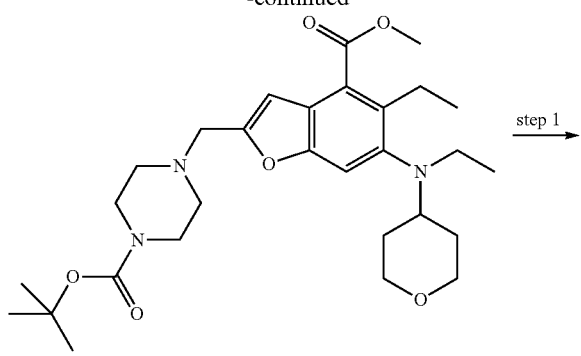

5a

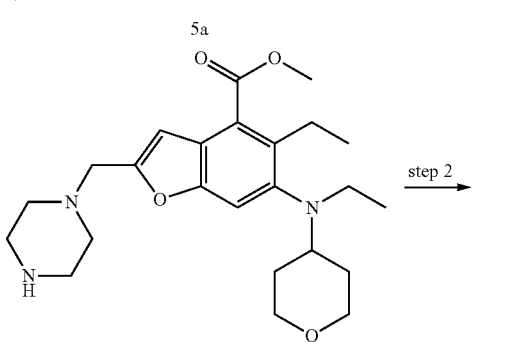

11a

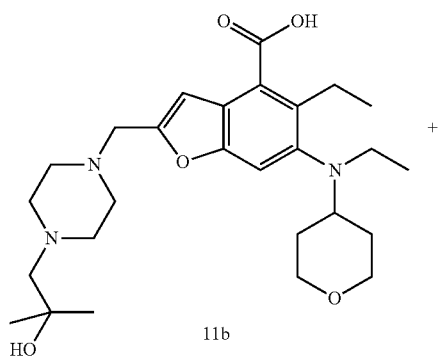

11b

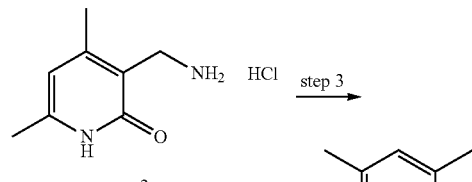

2a

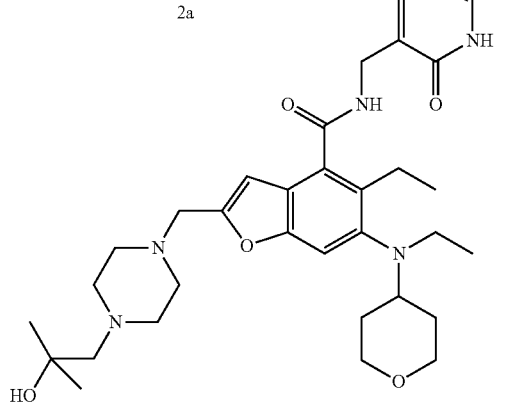

11

Step 1

Methyl 5-Ethyl-6-(ethyl(tetrahydro-2H-pyran-4-yl) amino)-2-(piperazin-1-ylmethyl)benzofuran-4-carboxylate 1a Compound 5a (60 mg, 0.12 mmol) was dissolved in 5 mL of dichloromethane, then 0.5 mL of trifluoroacetic acid was added. After stirring for 2 hours, the mixture was concentrated under reduced pressure, neutralized with saturated sodium carbonate solution, and extracted with a mixture of dichloromethane and methanol. The organic phases were combined, washed with saturated sodium chloride solution, dried over anhydrous sodium sulfate, and filtered. The filtrate was concentrated under reduced pressure to obtain the crude title compound 11a (45 mg) as a yellow solid, which was directly used in the next step without further purification.

Step 2

5-Ethyl-6-(ethyl(tetrahydro-2H-pyran-4-yl)amino)-2-((4-(2-hydroxy-2-methylpropyl)piperazin-1-yl) methyl)benzofuran-4-carboxylic acid 11b The crude 11a (25 mg, 0.06 mmol) was dissolved in 5 mL of ethanol, then 2,2-dimethyloxirane (6.5 mg, 0.09 mmol) and potassium carbonate (17 mg, 0.12 mmol) were added. The mixture was stirred at 60° C. for 12 hours. After the reaction was completed, the mixture was filtered, and 12M hydrochloric acid was added to adjust the pH to 4. The mixture was concentrated under reduced pressure, and the resulting residue was purified by high performance liquid chromatography to obtain the title compound 11b (15 mg, yield 52%) as a white solid.

Step 3

N-((4,6-Dimethyl-2-oxo-1,2-dihydropyridin-3-yl) methyl)-5-ethyl-6-(ethyl(tetrahydro-2H-pyran-4-yl) amino)-2-((4-(2-hydroxy-2-methylpropyl)piperazin-1-yl)methyl)benzofuran-4-carboxamide 11

Compound 11b (15 mg, 0.031 mmol) was dissolved in 4 mL of N,N-dimethylformamide, then 1-ethyl-3-(3-dimethylaminopropyl)carbodiimide (9 mg, 0.046 mmol), 1-hydroxybenzotriazole (7 mg, 0.046 mmol) and N,N-diisopropylethylamine (20 mg, 0.155 mmol) were added to the above reaction solution. The mixture was stirred for 1 hour, then compound 2a (9 mg, 0.046 mmol) was added to the above reaction solution. The mixture was stirred for 12 hours. After the reaction was completed, excess water was added, and the reaction solution was extracted with a mixture of dichloromethane and methanol (V:V=10:1) (10 mL). The organic phases were combined, washed with water (20 mL) and saturated sodium chloride solution (20 mL), dried over anhydrous sodium sulfate, and filtered. The filtrate was concentrated under reduced pressure, and the resulting residue was purified by thin-layer chromatography with elution system A to obtain the title compound 11 (13 mg, yield 70%) as a white solid.

MS m/z (ESI): 622.7 [M+1]

$^1$H NMR (400 MHz, DMSO-$d_6$) δ 11.48 (brs, 1H), 8.17 (t, 1H), 7.39 (s, 1H), 6.48 (s, 1H), 5.86 (s, 1H), 4.32 (d, 2H), 4.04 (brs, 1H), 3.83 (brd, 2H), 3.58 (s, 2H), 3.21 (t, 2H), 3.04 (q, 2H), 2.91-2.97 (m, 1H), 2.79 (q, 2H), 2.56 (brs, 4H), 2.45

(brs, 4H), 2.23 (s, 3H), 2.16 (brs, 2H), 2.11 (s, 3H), 1.63-1.66 (m, 2H), 1.48-1.52 (m, 2H), 1.00-1.06 (m, 9H), 0.82 (t, 3H).

Example 12

5-Ethyl-6-(ethyl(tetrahydro-2H-pyran-4-yl)amino)-N-((4-methoxy-6-methyl-2-oxo-1,2-dihydropyridin-3-yl)methyl)-2-((4-methylpiperazin-1-yl)methyl)benzofuran-4-carboxamide 12

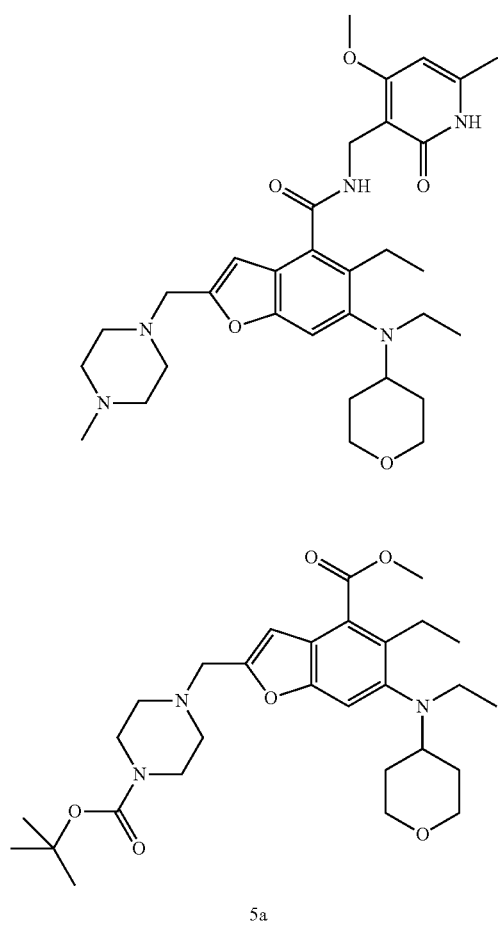

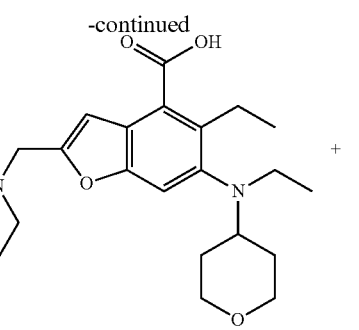

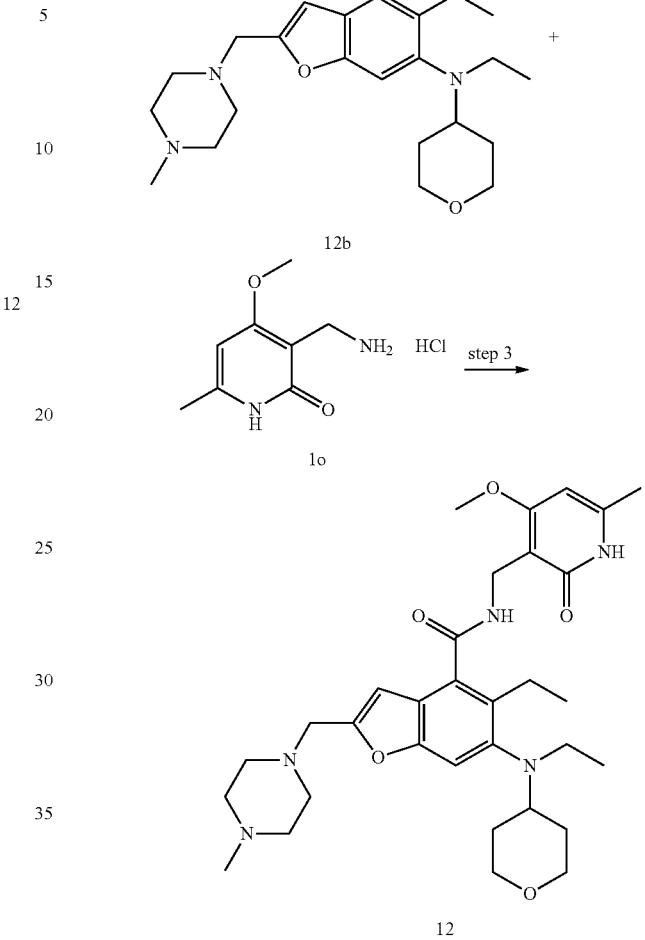

Step 1

Methyl 5-ethyl-6-(ethyl(tetrahydro-2H-pyran-4-yl)amino)-2-((4-methylpiperazin-1-yl)methyl)benzofuran-4-carboxylate 12a Compound 5a (74 mg, 0.14 mmol) was dissolved in 10 mL of 1,2-dichloroethane, then 1.0 mL of trifluoroacetic acid was added. After stirring for 1 hour, the mixture was concentrated under reduced pressure. Then, 5 mL of methanol, formaldehyde (61 mg, 1.4 mmol) and sodium triacetoxyborohydride (88 mg, 0.42 mmol) were added to the residue, successively. The mixture was stirred for 3 hours. After the reaction was completed, the mixture was concentrated under reduced pressure, neutralized with 20 mL of saturated sodium bicarbonate solution, and extracted with a mixture of dichloromethane and methanol (V:V=8:1) (10 mL). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system A to obtain the title compound 12a (60 mg, yield 97%) as a yellow oil.

Step 2

5-Ethyl-6-(ethyl(tetrahydro-2H-pyran-4-yl)amino)-2-((4-methylpiperazin-1-yl)methyl)benzofuran-4-carboxylic acid 12b Compound 12a (60 mg, 0.13 mmol) was dissolved in 4 mL of methanol, then 4 mL of 20% sodium hydroxide solution were added. The mixture was stirred for 12 hours at 60° C. After the reaction was completed, 12 M hydrochloric acid was added to adjust the pH to 4. The mixture was concentrated under reduced pressure, then the residue was dissolved in 10 mL of methanol and filtered. The filtrate was concentrated under reduced pressure to obtain the crude title compound 12b (55 mg) as a yellow solid, which was used directly in the next step without further purification.

Step 3

5-Ethyl-6-(ethyl(tetrahydro-2H-pyran-4-yl)amino)-N-((4-methoxy-6-methyl-2-oxo-1,2-dihydropyridin-3-yl)methyl)-2-((4-methylpiperazin-1-yl)methyl)benzofuran-4-carboxamide 12

The crude 12b (25 mg, 0.058 mmol) was dissolved in 3 mL of N,N-dimethylformamide, then 1-ethyl-3-(3-dimethylaminopropyl)carbodiimide (17 mg, 0.087 mmol), 1-hydroxybenzotriazole (12 mg, 0.087 mmol) and N,N-diisopropylethylamine (38 mg, 0.29 mmol) were added. The mixture was stirred 2 hours, then compound 1o (18 mg, 0.087 mmol) was added to the reaction solution. The mixture was stirred for 12 hours. After the reaction was completed, 20 mL of water was added, the reaction solution was extracted with a mixture of dichloromethane and methanol (V:V=8:1) (10 mL×3). The organic phases were combined, washed with water (10 mL) and saturated sodium chloride solution (10 mL), dried over anhydrous sodium sulfate, and filtered. The filtrate was concentrated under reduced pressure, and the resulting residue was purified by thin-layer chromatography with elution system A to obtain the title compound 12 (22 mg, yield 65%) as a white solid.

MS m/z (ESI): 580.3 [M+1]

$^1$H NMR (400 MHz, DMSO-d$_6$) δ 11.43 (brs, 1H), 7.99 (s, 1H), 7.38 (s, 1H), 6.56 (s, 1H), 6.10 (s, 1H), 4.28 (d, 2H), 3.85 (brs, 2H), 3.82 (s, 3H), 3.63 (s, 2H), 3.21 (t, 2H), 3.02-3.07 (m, 2H), 2.92-2.97 (m, 1H), 2.79-2.81 (m, 2H), 2.58 (brs, 4H), 2.40 (brs, 4H), 2.18 (s, 3H), 1.64-1.66 (m, 2H), 1.46-1.55 (m, 2H), 1.05 (t, 3H), 0.82 (t, 3H).

Example 13

2-((Dimethylamino)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide 13

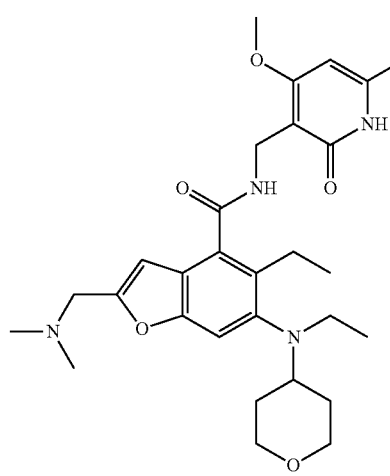

13

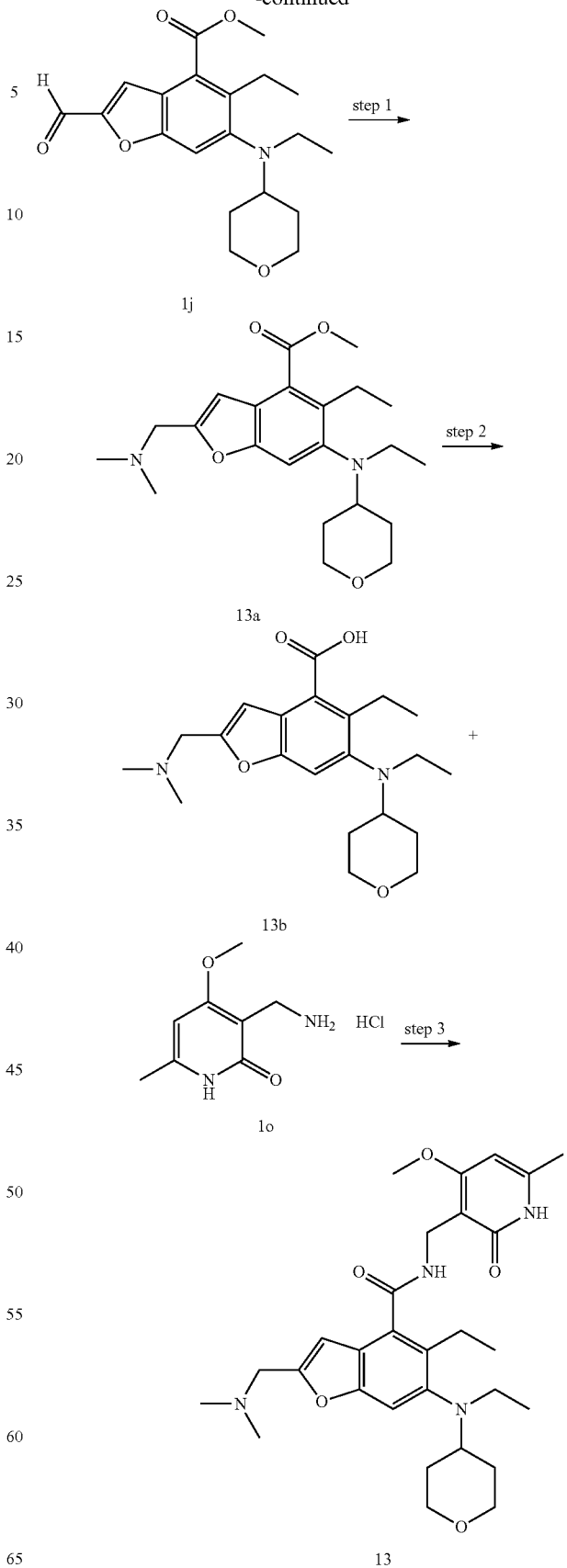

Step 1

Methyl 2-((dimethylamino)methyl)-5-ethyl-6-(ethyl (tetrahydro-2H-pyran-4-yl)amino)benzofuran-4-carboxylate 13a Compound 1j (30 mg, 0.084 mmol) was dissolved in 5 mL of methanol, then dimethylamine hydrochloride (14 mg, 0.17 mmol) was added. The mixture was stirred for 1 hour, then sodium triacetoxyborohydride (53 mg, 0.25 mmol) was added. The mixture was stirred for 12 hours. After the reaction was completed, the reaction solution was concentrated under reduced pressure, neutralized with saturated sodium bicarbonate solution, and extracted with a mixture of dichloromethane and methanol. The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound 13a (30 mg, yield 90%) as a yellow oil.

Step 2

2-((Dimethylamino)methyl)-5-ethyl-6-(ethyl(tetrahydro-2H-pyran-4-yl)amino)benzofuran-4-carboxylic acid 13b Compound 13a (30 mg, 0.077 mmol) was dissolved in 3 mL of ethanol and 1 mL of tetrahydrofuran, then 5 mL of 2N sodium hydroxide solution were added. The mixture was stirred for 12 hours at 60° C. After the reaction was completed, the reaction solution was adjusted to weak acidity with concentrated hydrochloric acid. The mixture was concentrated under reduced pressure, and the residue was dissolved in a mixture of dichloromethane and methanol (V:V=1:1) and filtered to remove inorganic salts. The filtrate was concentrated under reduced pressure to obtain the crude title compound 13b (25 mg) as a yellow oil, which was directly used in the next step without further purification.

Step 3

2-((Dimethylamino)methyl)-5-ethyl-6-(ethyl(tetrahydro-2H-pyran-4-yl)amino)-N-((4-methoxy-6-methyl-2-oxo-1,2-dihydropyridin-3-yl)methyl)benzofuran-4-carboxamide 13

The crude 13b (15 mg, 0.040 mmol) was dissolved in 3 mL of N,N-dimethylformamide, then 1-ethyl-3-(3-dimethylaminopropyl)carbodiimide (7.7 mg, 0.04 mmol), 1-hydroxybenzotriazole (8 mg, 0.060 mmol) and N,N-diisopropylethylamine (26 mg, 0.20 mmol) were added. The mixture was stirred for 0.5 hour, then compound 1o (11 mg, 0.052 mmol) was added. The mixture was stirred for 12 hours. After the reaction was completed, excess water was added, and the reaction solution was extracted with a mixture of dichloromethane and methanol (V:V=8:1) (10 mL). The organic phases were combined, washed with water (10 mL) and saturated sodium chloride solution (10 mL), dried over anhydrous sodium sulfate, and filtered. The filtrate was concentrated under reduced pressure, and the resulting residue was purified by thin-layer chromatography with elution system A to obtain the title compound 13 (7 mg, yield 30%) as a white solid.

MS m/z (ESI): 525.5 [M+1]

$^1$H NMR (400 MHz, DMSO-d$_6$) δ 11.44 (brs, 1H), 8.00 (brs, 1H), 7.37 (s, 1H), 6.51 (s, 1H), 6.10 (s, 1H), 4.28 (d, 2H), 3.85 (brs, 2H), 3.82 (s, 3H), 3.52 (s, 2H), 3.21 (t, 2H), 3.02-3.06 (m, 2H), 2.92-2.96 (m, 1H), 2.77-2.83 (m, 2H), 2.19 (s, 6H), 2.17 (s, 3H), 1.63-1.67 (m, 2H), 1.46-1.53 (m, 2H), 1.06 (t, 3H), 0.82 (t, 3H).

Example 14

2-Cyclopentyl-N-((4,6-dimethyl-2-oxo-1,2-dihydropyridin-3-yl)methyl)-5-ethyl-6-(ethyl(tetrahydro-2H-pyran-4-yl)amino)benzofuran-4-carboxamide 14

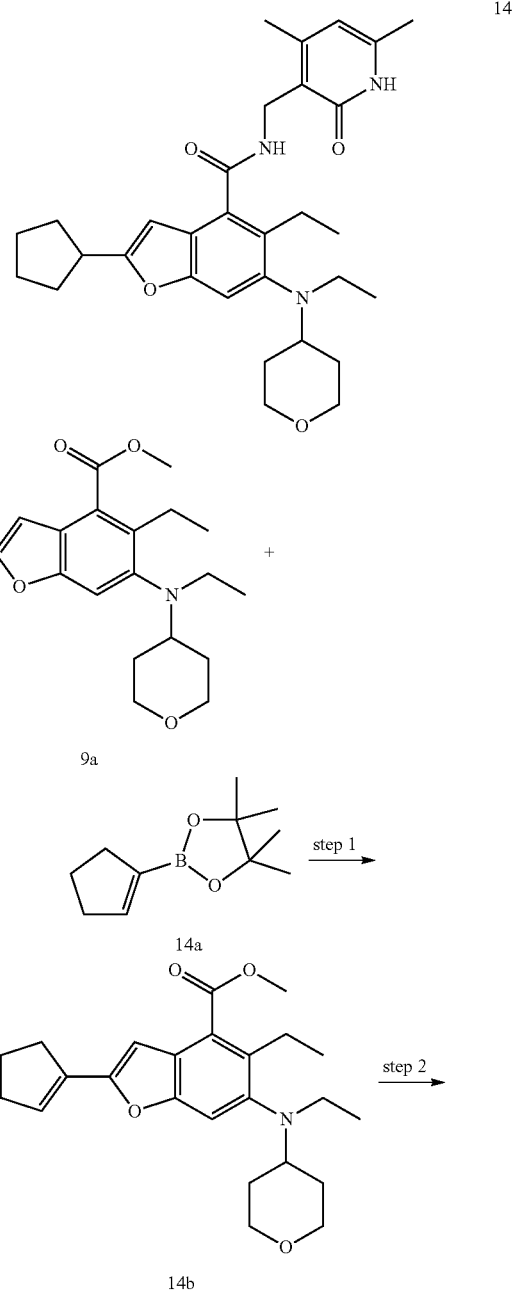

-continued

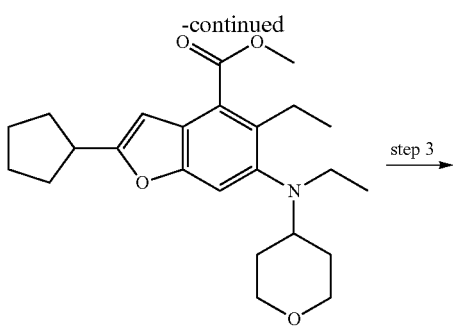

14c

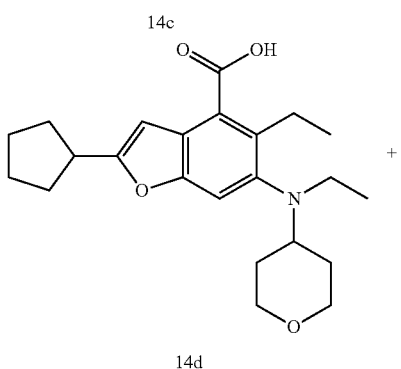

14d

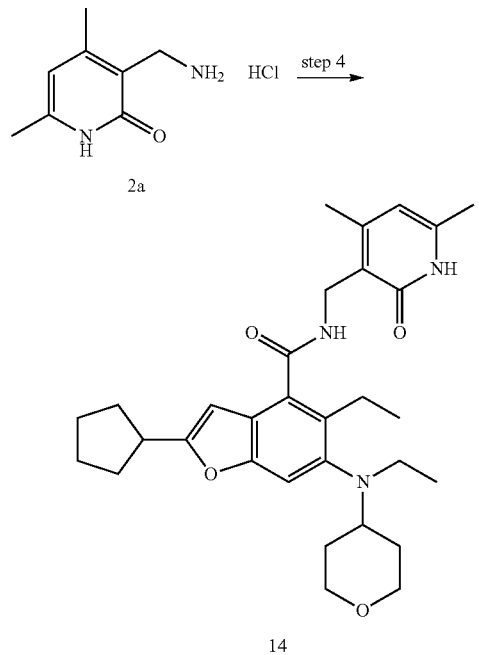

14

Step 1

Methyl 2-(cyclopent-1-en-1-yl)-5-ethyl-6-(ethyl(tetrahydro-2H-pyran-4-yl)amino)benzofuran-4-carboxylate 14b Compound 9a (70 mg, 0.17 mmol), 2-(cyclopent-1-en-1-yl)-4,4,5,5-tetramethyl-1,3,2-dioxaborolane 14a (40 mg, 0.20 mmol), tris(dibenzylideneacetone)dipalladium (16 mg, 0.017 mmol), 2-dicyclohexylphosphino-2',4',6'-triisopropylbiphenyl (16 mg, 0.034 mmol) and sodium carbonate (52 mg, 0.51 mmol) were dissolved in 5 m of toluene. The mixture was stirred for 12 hours at 100° C. under an argon atmosphere. After the reaction was completed, the mixture was filtered through celite. The filtrate was concentrated under reduced pressure, and the resulting residue was purified by thin-layer chromatography with elution system A to obtain the title compound 14b (50 mg, yield 75%) as a yellow oil.

Step 2

Methyl 2-cyclopentyl-5-ethyl-6-(ethyl(tetrahydro-2H-pyran-4-yl)amino)benzofuran-4-carboxylate 14c Compound 14b (75 mg, 0.19 mmol) was dissolved in 5 mL of methanol, then 20 mg of 10% Pd/C was added. The reaction system was purged three times with hydrogen and stirred for 1 hour. After the reaction was completed, the mixture was filtered through celite. The filtrate was concentrated under reduced pressure, and the resulting residue was purified by thin-layer chromatography with elution system A to obtain the title compound 14c (55 mg, yield 73%) as a colorless oil.

Step 3

2-Cyclopentyl-5-ethyl-6-(ethyl(tetrahydro-2H-pyran-4-yl)amino)benzofuran-4-carboxylic acid 14d Compound 14c (55 mg, 0.14 mmol) was dissolved in 5 mL of a mixture of methanol and tetrahydrofuran (V:V=3:2), then 2 mL of 2N sodium hydroxide solution was added. The mixture was stirred for 12 hours at 60° C. After the reaction was completed, the mixture was concentrated under reduced pressure to remove organic solvents, neutralized with 12M hydrochloric acid to adjust the pH to 3, and extracted with ethyl acetate (10 mL×3). The organic phases were combined, washed with saturated sodium chloride solution (10 mL), dried over anhydrous sodium sulfate, and filtered. The filtrate was concentrated under reduced pressure to obtain the crude title compound 14d (45 mg, yield 85%)) as a colorless oil.

Step 4

2-Cyclopentyl-N-((4,6-dimethyl-2-oxo-1,2-dihydropyridin-3-yl)methyl)-5-ethyl-6-(ethyl(tetrahydro-2H-pyran-4-yl)amino)benzofuran-4-carboxamide 14

Compound 14d (15 mg, 0.065 mmol) was dissolved in 4 mL of N,N-dimethylformamide, then 1-ethyl-3-(3-dimethylaminopropyl)carbodiimide (20 mg, 0.097 mmol), 1-hydroxybenzotriazole (15 mg, 0.097 mmol) and N,N-diisopropylethylamine (50 mg, 0.33 mmol) were added to the reaction solution. The mixture was stirred 1 hour, then compound 2a (18 mg, 0.097 mmol) was added. The mixture was stirred for 12 hours. After the reaction was completed, 20 mL of water was added, and the reaction solution was extracted with a mixture of dichloromethane and methanol (V:V=8:1) (10 mL×3). The organic phases were combined, washed successively with water and saturated sodium chloride solution, dried over anhydrous sodium sulfate, and filtered. The filtrate was concentrated under reduced pressure, and the resulting residue was purified by thin-layer chromatography with elution system A to obtain the title compound 14 (18 mg, yield 53%) as a white solid.

MS m/z (ESI): 520.5 [M+1]

$^1$H NMR (400 MHz, DMSO-$d_6$) δ 11.49 (brs, 1H), 8.09 (s, 1H), 7.35 (s, 1H), 6.30 (s, 1H), 5.87 (s, 1H), 4.31 (d, 2H), 3.82 (brd, 2H), 3.16-3.23 (m, 3H), 3.03 (q, 2H), 2.90-2.96 (m, 1H), 2.79 (q, 2H), 2.24 (s, 3H), 2.11 (s, 3H), 2.00 (brd, 2H), 1.67 (brs, 8H), 1.43-1.53 (m, 2H), 1.01 (t, 3H), 0.81 (t, 3H).
Example 15
N-((4,6-Dimethyl-2-oxo-1,2-dihydropyridin-3-yl)methyl)-6-(ethyl(tetrahydro-2H-pyran-4-yl)amino)-5-methyl-2-(1-methylpiperidin-4-yl)benzofuran-4-carboxamide
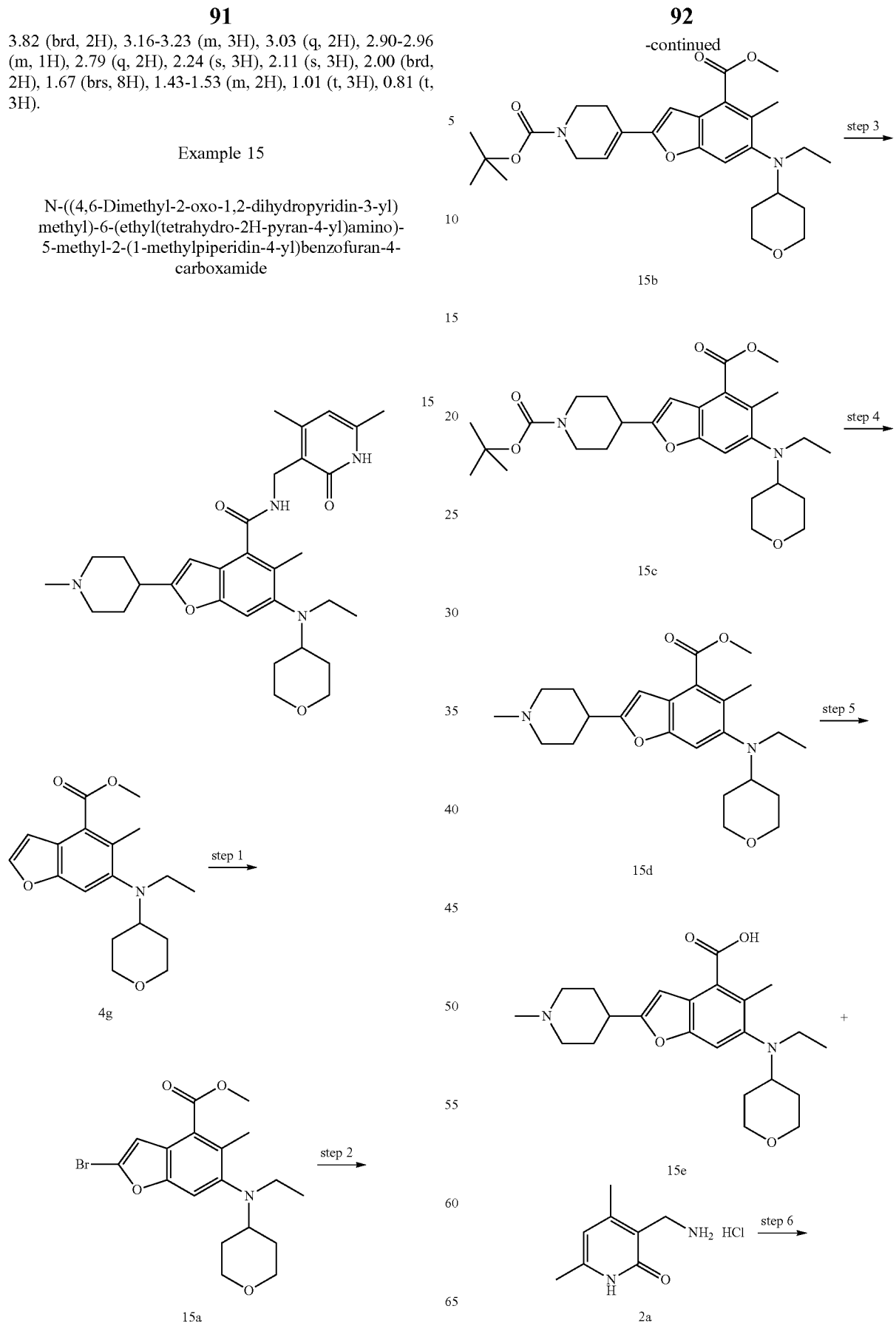

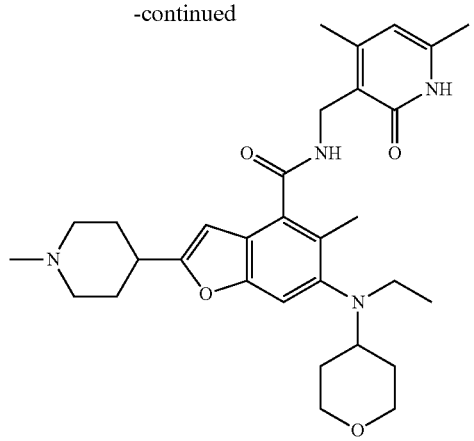

15

Step 1

Methyl 2-bromo-6-(ethyl(tetrahydro-2H-pyran-4-yl) amino)-5-methylbenzofuran-4-carboxylate 15a Compound 4g (330 mg, 1.04 mmol) was dissolved in 6 mL of tetrahydrofuran, then 0.63 mL of 2M lithium diisopropylamide was added dropwise at −70° C. under an argon atmosphere. At −70° C., the mixture was stirred for 1 hour, then 20 mL of a pre-prepared solution of 1,2-dibromotetrachloroethane (170 mg, 0.53 mmol) in tetrahydrofuran was added. The mixture was slowly warmed up and stirred for 1 hour. After the reaction was completed, 5 mL of saturated ammonium chloride solution was added to quench the reaction, and the mixture was extracted with ethyl acetate (10 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system B to obtain the title compound 15a (145 mg, yield 35%) as a yellow oil.

Step 2 tert-Butyl 4-(6-(ethyl(tetrahydro-2H-pyran-4-yl) amino)-4-(methoxycarbonyl)-5-methylbenzofuran-2-yl)-5,6-dihydropyridine-1 (2H)-carboxylate 15b Compound 15a (90 mg, 0.23 mmol), tert-butyl 4-(4,4,5,5-tetramethyl-1,3,2-dioxaborolan-2-yl)-5,6-dihydropyridine-1(2H)-carboxylate (105 mg, 0.34 mmol), tris(dibenzylideneacetone)dipalladium (21 mg, 0.023 mmol), 2-dicyclohexylphosphino-2',4',6'-triisopropylbiphenyl (22 mg, 0.045 mmol) and sodium carbonate (72 mg, 0.68 mmol) were dissolved in 5 mL of a mixture of 1,4-dioxane and water (V:V=4:1). The mixture was stirred for 12 hours at 90° C. under an argon atmosphere. After the reaction was completed, the mixture was filtered through a pad of celite, and two phases were separated. The organic phase was washed successively with water and saturated sodium chloride solution, dried over anhydrous sodium sulfate, and filtered. The filtrate was concentrated under reduced pressure, and the resulting residue was purified by thin-layer chromatography with elution system B to obtain the title compound 15b (100 mg, yield 88%) as a yellow solid.

Step 3 tert-Butyl 4-(6-(ethyl(tetrahydro-2H-pyran-4-yl) amino)-4-(methoxycarbonyl)-5-methylbenzofuran-2-yl)piperidine-1-carboxylate 15c Compound 15b (100 mg, 0.2 mmol) was dissolved in 6 mL of ethanol, and 30 mg of 10% Pd/C was added. The reaction system was purged three times with hydrogen and stirred for 0.5 hour. The reaction solution was filtered, the filtrate was concentrated under reduced pressure, and the resulting residue was purified by thin-layer chromatography with elution system B to obtain the title compound 15c (80 mg, yield 80%) as a yellow oil.

Step 4

Methyl 6-(ethyl(tetrahydro-2H-pyran-4-yl)amino)-5-methyl-2-(1-methylpiperidin-4-yl)benzofuran-4-carboxylate 15d Compound 15c (80 mg, 0.16 mmol) was dissolved in 10 mL of dichloromethane, then 1 mL of trifluoroacetic acid was added. After stirring for 1 hour, the mixture was concentrated under reduced pressure. Then, 5 mL of methanol and 5 mL of formaldehyde were added, and the mixture was stirred for 1 hour, then sodium triacetoxyborohydride (100 mg, 0.48 mmol) were added. After stirring for 3 hours, the reaction solution was concentrated under reduced pressure, neutralized with saturated sodium bicarbonate solution, and extracted with a mixture of dichloromethane and methanol (V:V=8:1). The organic phases were combined, washed with saturated sodium chloride solution, and dried over anhydrous sodium sulfate. The resulting residue was purified by thin-layer chromatography with elution system A to obtain the title compound 15d (60 mg, yield 90%) as a yellow oil.

Step 5

6-(Ethyl(tetrahydro-2H-pyran-4-yl)amino)-5-methyl-2-(1-methylpiperidin-4-yl)benzofuran-4-carboxylic acid Compound 15d (30 mg, 0.072 mmol) was dissolved in 5 mL of methanol and 2 mL of tetrahydrofuran, then 2 mL of 4M sodium hydroxide solution were added. The mixture was stirred for 12 hours at 60° C. 12 M hydrochloric acid was added to adjust the pH of the reaction solution to 4, and the mixture was concentrated under reduced pressure. The residue was dissolved in 10 mL of methanol, and filtered. The filtrate was concentrated under reduced pressure to obtain the crude title compound 15e (30 mg) as a white solid, which was directly used in the next step without further purification.

Step 6

N-((4,6-Dimethyl-2-oxo-1,2-dihydropyridin-3-yl) methyl)-6-(ethyl(tetrahydro-2H-pyran-4-yl)amino)-5-methyl-2-(1-methylpiperidin-4-yl)benzofuran-4-carboxamide 15

The crude 15e (25 mg, 0.06 mmol) was dissolved in 3 mL of N,N-dimethylformamide, then 1-ethyl-3-(3-dimethylaminopropyl)carbodiimide (18 mg, 0.094 mmol), 1-hydroxybenzotriazole (15 mg, 0.094 mmol) and N,N-diisopropylethylamine (40 mg, 0.31 mmol) were added. The mixture was stirred 1 hour, then compound 2a (18 mg, 0.094 mmol) was added. The mixture was stirred for 12 hours. After the reaction was completed, 20 mL of water were added, and the reaction solution was extracted with a mixture of dichloromethane and methanol. The organic phases were combined, washed successively with water and saturated sodium chloride solution, dried over anhydrous sodium sulfate, and filtered. The filtrate was concentrated under reduced pressure, and the resulting residue was purified by thin-layer chromatography with elution system A to obtain the title compound 15 (24 mg, yield 73%) as a white solid.

MS m/z (ESI): 535.5 [M+1]

$^1$H NMR (400 MHz, DMSO-d$_6$) δ 11.50 (brs, 1H), 8.10 (s, 1H), 7.34 (s, 1H), 6.29 (s, 1H), 5.87 (s, 1H), 4.31 (d, 2H), 3.81 (brd, 2H), 3.22 (t, 2H), 3.03 (q, 2H), 2.91-2.94 (m, 1H), 2.80 (brd, 2H), 2.67 (brs, 1H), 2.23 (s, 3H), 2.22 (s, 3H), 2.18 (s, 3H), 2.11 (s, 3H), 1.92-2.02 (m, 4H), 1.61-1.64 (m, 4H), 1.45-1.48 (m, 2H), 0.78 (t, 3H).

Example 16

N-((4,6-Dimethyl-2-oxo-1,2-dihydropyridin-3-yl)methyl)-6-(ethyl(tetrahydro-2H-pyran-4-yl)amino)-5-methyl-2-(1-methyl-1,2,3,6-tetrahydropyridin-4-yl)benzofuran-4-carboxamide 16

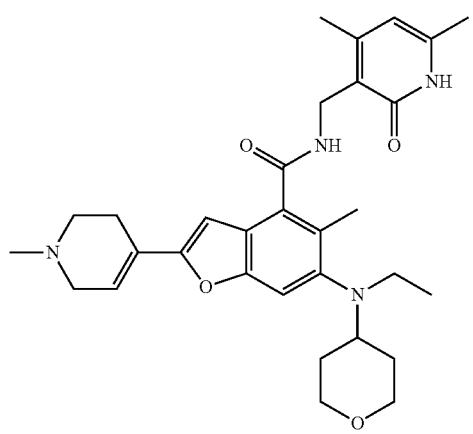

In accordance with the synthetic route of Example 12, the starting material 5a was replaced with compound 15b, and compound 1o was replaced with compound 2a, accordingly, the title compound 16 (18 mg, yield 62%) as a white solid was prepared.

MS m/z (ESI): 533.5 [M+1]

$^1$H NMR (400 MHz, DMSO-d$_6$) δ 11.51 (brs, 1H), 8.17 (t, 1H), 7.35 (s, 1H), 6.58 (s, 1H), 6.35 (s, 1H), 5.87 (s, 1H), 4.31 (d, 2H), 3.81 (brd, 2H), 3.19-3.25 (m, 3H), 3.02-3.07 (m, 3H), 2.90-2.97 (m, 1H), 2.43 (brs, 2H), 2.23 (s, 3H), 2.22 (s, 3H), 2.11 (s, 3H), 1.62-1.64 (m, 2H), 1.44-1.51 (m, 2H), 1.17 (t, 2H), 0.79 (t, 3H).

Example 17

5-Ethyl-6-(ethyl(tetrahydro-2H-pyran-4-yl)amino)-N-((4-methoxy-6-methyl-2-oxo-1,2-dihydropyridin-3-yl)methyl)-2-(1-methylpiperidin-4-yl)benzofuran-4-carboxamide 17

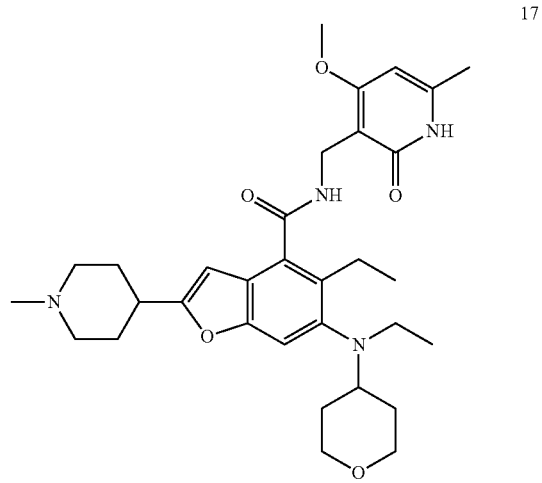

In accordance with the synthetic route of Example 12, the starting material 5a was replaced with compound 9c, accordingly, the title compound 17 (17 mg, yield 50%) as a white solid was prepared.

MS m/z (ESI): 565.2 [M+1]

$^1$H NMR (400 MHz, DMSO-d$_6$) δ 11.43 (brs, 1H), 7.94 (brs, 1H), 7.35 (s, 1H), 6.39 (brs, 1H), 6.10 (s, 1H), 4.27 (d, 2H), 3.83 (brs, 2H), 3.81 (s, 3H), 3.20 (t, 2H), 3.02 (q, 2H), 2.90-2.95 (m, 2H), 2.79 (q, 2H), 2.44 (brs, 4H), 2.18 (s, 3H), 2.07 (brs, 2H), 1.81 (brs, 2H), 1.62-1.64 (m, 2H), 1.43-1.52 (m, 2H), 1.03 (t, 3H), 0.80 (t, 3H).

Example 18

6-(Ethyl(tetrahydro-2H-pyran-4-yl)amino)-N-((4-methoxy-6-methyl-2-oxo-1,2-dihydro pyridin-3-yl)methyl)-5-methylbenzofuran-4-carboxamide 18

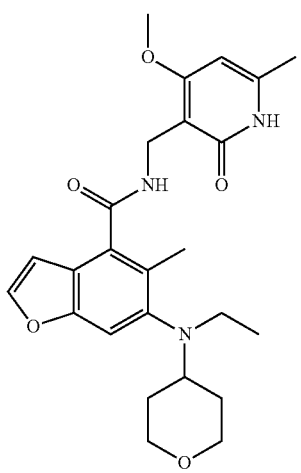

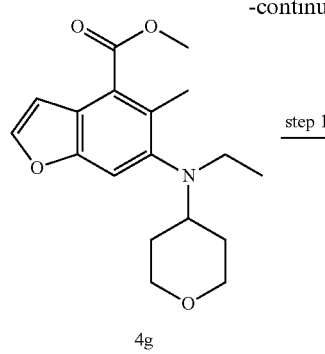

4g

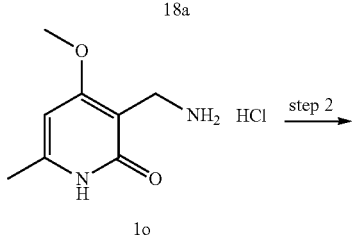

18a

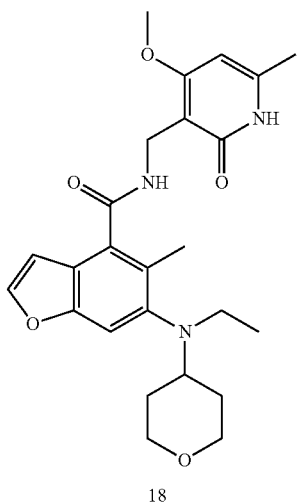 [SMILES: CCN(c1cc2occc2c(C(=O)NCc2c(OC)cc(C)[nH]c2=O)c1C)C1CCOCC1]

1o chloric acid was added to adjust the pH to 3, and the mixture was extracted with ethyl acetate (10 mL×3). The organic phases were combined, washed with saturated sodium chloride solution (20 mL×1), and dried over anhydrous sodium sulfate. The filtrate was concentrated under reduced pressure, and the resulting residue was purified by thin-layer chromatography with elution system B to obtain the title compound 18a (40 mg, yield 93%) as a white solid.

Step 2

6-(Ethyl(tetrahydro-2H-pyran-4-yl)amino)-N-((4-methoxy-6-methyl-2-oxo-1,2-dihydro pyridin-3-yl)methyl)-5-methylbenzofuran-4-carboxamide 18

Compound 18a (15 mg, 0.049 mmol) was dissolved in 3 mL of N,N-dimethylformamide, then N,N-diisopropylethylamine (18.9 mg, 0.147 mmol) and 2-(7-azabenzotriazol-1-yl)-N,N,N',N'-tetramethyluronium hexafluorophosphate (27.9 mg, 0.0735 mmol) were added. The reaction system was stirred for 1 hour at 0° C. Compound 1o (12 mg, 0.0558 mmol) was added under a nitrogen atmosphere. The mixture was stirred for 12 hours at room temperature. After the reaction was completed, 30 mL of water was added, the mixture was extracted with ethyl acetate (10 mL×3). The organic phases were combined, washed with saturated sodium chloride solution (20 mL×1), dried over anhydrous sodium sulfate, and filtered. The filtrate was concentrated under reduced pressure, and the resulting residue was purified by thin-layer chromatography with elution system A to obtain the title compound 18 (4.4 mg, yield 20%) as a white solid.

MS m/z (ESI): 454.2 [M+1]

$^1$H NMR (400 MHz, CDCl$_3$) δ 10.90 (s, 1H), 7.43 (s, 1H), 7.27 (s, 1H), 6.76 (s, 1H), 6.61 (s, 1H), 5.85 (s, 1H), 4.52 (brs, 2H), 3.90-3.93 (brd, 2H), 3.82 (s, 3H), 3.28 (t, 2H), 3.02-3.07 (m, 2H), 2.91-2.95 (m, 1H), 2.29 (s, 3H), 1.83 (s, 3H), 1.56-1.68 (m, 4H), 0.83 (t, 3H).

Example 19

6-(Ethyl(tetrahydro-2H-pyran-4-yl)amino)-N-((4-methoxy-6-methyl-2-oxo-1,2-dihydro pyridin-3-yl)methyl)-2,5-dimethylbenzofuran-4-carboxamide 19

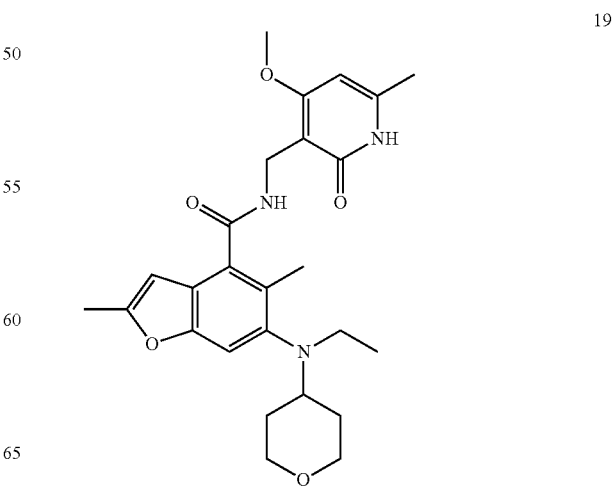

19

Step 1

6-(Ethyl(tetrahydro-2H-pyran-4-yl)amino)-5-methyl-benzofuran-4-carboxylic acid 18a Compound 4g (45 mg, 0.142 mmol) was dissolved in 4 m/of a mixture of methanol and water (V:V=1:1), then sodium hydroxide (60 mg, 1.58 mmol) was added. The mixture was stirred for 12 hours at 70° C. After the reaction was completed, the reaction solution was concentrated under reduced pressure to remove methanol. Then, 10% hydro-

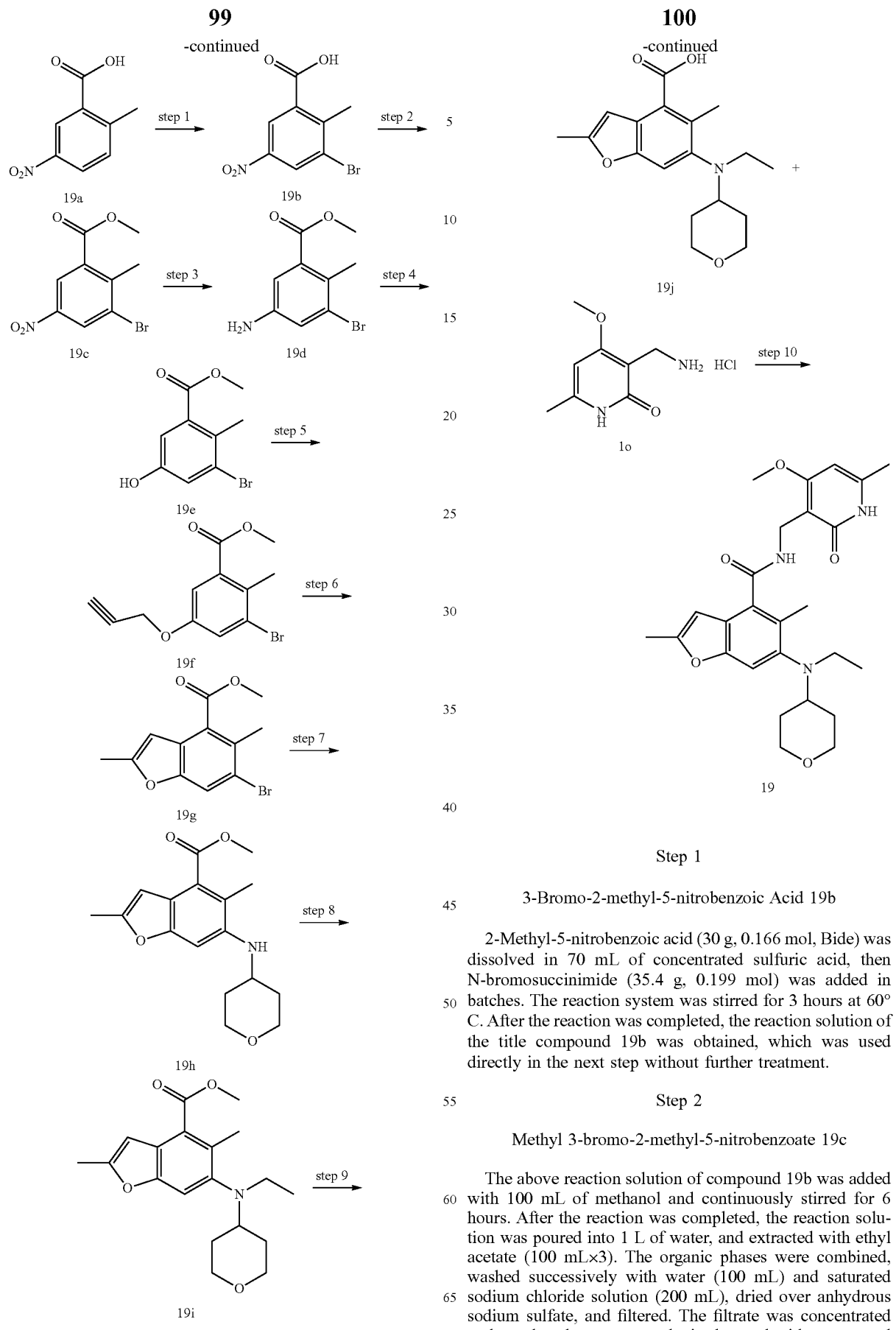

Step 1

3-Bromo-2-methyl-5-nitrobenzoic Acid 19b

2-Methyl-5-nitrobenzoic acid (30 g, 0.166 mol, Bide) was dissolved in 70 mL of concentrated sulfuric acid, then N-bromosuccinimide (35.4 g, 0.199 mol) was added in batches. The reaction system was stirred for 3 hours at 60° C. After the reaction was completed, the reaction solution of the title compound 19b was obtained, which was used directly in the next step without further treatment.

Step 2

Methyl 3-bromo-2-methyl-5-nitrobenzoate 19c

The above reaction solution of compound 19b was added with 100 mL of methanol and continuously stirred for 6 hours. After the reaction was completed, the reaction solution was poured into 1 L of water, and extracted with ethyl acetate (100 mL×3). The organic phases were combined, washed successively with water (100 mL) and saturated sodium chloride solution (200 mL), dried over anhydrous sodium sulfate, and filtered. The filtrate was concentrated under reduced pressure to obtain the crude title compound 19c (53 g) as a white solid, which was directly used in the next step without further purification.

Step 3

Methyl 5-amino-3-bromo-2-methylbenzoate 19d

The crude 19c (52 g, 0.189 mol) was dissolved in 200 mL of ethanol, then iron powder (31.7 g, 0.569 mol) was added, and 16 mL of 4 N hydrochloric acid were slowly added dropwise. The mixture was heated to 75° C. and stirred for 4 hours. After the reaction was completed, 200 mL of water were added, and the mixture was extracted with ethyl acetate (100 mL×3). The organic phases were combined, washed with saturated sodium chloride solution (200 mL), dried over anhydrous sodium sulfate, and filtered. The filtrate was concentrated under reduced pressure, and the resulting residue was purified by silica gel column chromatography with elution system B to obtain the title compound 19d (27 g, yield 59%) as a yellow solid.

Step 4

Methyl 3-bromo-5-hydroxy-2-methylbenzoate 19e

Compound 19d (5 g, 0.02 mol) was dissolved in 50 mL of 10% sulfuric acid, then 10 mL of a pre-prepared solution of sodium nitrite (1.55 g, 0.023 mol) were added at 0° C. The mixture was stirred for 1 hour, then 50 mL of 50% sulfuric acid were added. The mixture was heated to 100° C. and stirred for 1 hour. After the reaction was completed, the reaction solution was extracted with ethyl acetate (50 mL×3). The organic phases were combined, washed with saturated sodium chloride solution (100 mL), dried over anhydrous sodium sulfate, and filtered. The filtrate was concentrated under reduced pressure, and the resulting residue was purified by silica gel column chromatography with elution system B to obtain the title compound 19e (1.4 g, yield 29%) as a yellow solid.

Step 5

Methyl 3-bromo-2-methyl-5-(prop-2-yn-1-yloxy)benzoate 19f

Compound 19e (0.5 g, 2.04 mmol) was dissolved in 20 mL of acetone, then 3-bromopropyne (0.73 g, 6.12 mmol) and potassium carbonate (0.85 g, 6.12 mmol) were added. The reaction system was stirred at 80° C. for 12 hours. After the reaction was completed, the reaction solution was concentrated under reduced pressure, then 20 mL of water were added, and the mixture was extracted with ethyl acetate (10 mL×3). The organic phases were combined, washed with saturated sodium chloride solution (20 mL), dried over anhydrous sodium sulfate, and filtered. The filtrate was concentrated under reduced pressure, and the resulting residue was purified by silica gel column chromatography with elution system B to obtain the title compound 19f (0.5 g, yield 86.7%) as a yellow liquid.

Step 6

Methyl 6-bromo-2,5-dimethylbenzofuran-4-carboxylate 19g

Compound 19f (0.5 g, 1.76 mmol) and cesium fluoride (0.79 g, 5.28 mmol) were added to 5 mL of N,N-diethylaniline. The mixture was stirred for 2 hours at 200° C. in a microwave. After the reaction was completed, 20 mL of water was added, and the mixture was extracted with ethyl acetate (20 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system B to obtain the title compound 19g (0.2 g, yield 40%) as a yellow liquid.

Step 7

Methyl 2,5-dimethyl-6-((tetrahydro-2H-pyran-4-yl)amino)benzofuran-4-carboxylate 19h Compound 19h (0.2 g, 0.70 mmol), tetrahydro-2H-pyran-4-amine (14 mg, 0.14 mmol), tris(dibenzylideneacetone)dipalladium (64 mg, 0.07 mmol), (±)-2,2'-bis(diphenylphosphino)-1,1'-binaphthalene (87.15 mg, 0.14 mmol) and cesium carbonate (455 mg, 1.4 mmol) were dissolved in 5 mL of toluene. The mixture was stirred for 12 hours at 110° C. under a nitrogen atmosphere. After the reaction was completed, 10 mL of water were added, and the mixture was extracted with ethyl acetate (10 mL×3). The organic phases were combined, dried over anhydrous sodium sulfate, and filtered. The filtrate was concentrated under reduced pressure, and the resulting residue was purified by thin-layer chromatography with elution system B to obtain the title compound 19h (140 g, yield 67%) as a yellow solid.

Step 8

Methyl 6-(ethyl(tetrahydro-2H-pyran-4-yl)amino)-2,5-dimethylbenzofuran-4-carboxylate 19i Compound 19h (90.0 g, 0.297 mmol), acetaldehyde (39.2 mg, 0.89 mmol) and acetic acid (89.1 mg, 1.48 mmol) were dissolved in 8 mL of methanol. The mixture was stirred for 1 hour at 0° C. and another 4 hours at room temperature under a nitrogen atmosphere, then sodium cyanoborohydride (55.9 mg, 0.891 mmol) was added. The mixture was stirred for 12 hours. After the reaction was completed, the reaction solution was concentrated under reduced pressure, 20 mL of water were added, and the mixture was extracted with ethyl acetate (10 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system B to obtain the title compound 19i (60 mg, yield 61%) as a colorless liquid.

Step 9

6-(Ethyl(tetrahydro-2H-pyran-4-yl)amino)-2,5-dimethylbenzofuran-4-carboxylic acid 19j Compound 19i (60 mg, 0.18 mmol) and potassium hydroxide (50.6 mg, 0.90 mmol) were added to 4 mL of a mixture of methanol and water (V:V=1:1). The mixture was stirred for 16 hours at 75° C. After the reaction was completed, the mixture was cooled, and 2N hydrochloric acid was added to adjust the pH of the reaction solution to 3-4. The mixture was extracted with a mixture of dichloromethane and methanol (V:V=10:1) (10 mL×3). The organic phases were combined, washed with saturated sodium chloride solution (20 mL), dried over anhydrous sodium sulfate, and filtered. The filtrate was concentrated under reduced pressure to obtain the crude title compound 19j (30 mg) as a yellow solid, which was used directly in the next step without further purification.

Step 10

6-(Ethyl(tetrahydro-2H-pyran-4-yl)amino)-N-((4-methoxy-6-methyl-2-oxo-1,2-dihydro pyridin-3-yl)methyl)-2,5-dimethylbenzofuran-4-carboxamide 19

The crude 19j (15 mg, 0.047 mmol) was dissolved in 2 mL of N,N-dimethylformamide, then N,N-diisopropylethylamine (18.3 mg, 0.14 mmol) and 2-(7-azabenzotriazol-1-yl)-N,N,N',N'-tetramethyluronium hexafluorophosphate (47.7 mg, 0.125 mmol) were added. The mixture was stirred 1 hour at 0° C., then compound 1o (11.58 mg, 0.057 mmol) was added. The mixture was stirred for 12 hours at room temperature. After the reaction was completed, 50 mL of water were added, then the mixture was extracted with a mixture of dichloromethane and methanol (V:V=10:1) (10 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system A to obtain the title compound 19 (20 mg, yield 91%) as a white solid.

MS m/z (ESI): 468.2 [M+1]

$^1$H NMR (400 MHz, CDCl$_3$) δ 11.57 (s, 1H), 7.19 (s, 1H), 6.38 (s, 1H), 5.93 (s, 1H), 5.36 (s, 1H), 4.64 (d, 2H), 3.95 (brs, 2H), 3.91 (s, 3H), 3.28-3.33 (m, 2H), 3.03-3.05 (m, 2H), 2.92-2.96 (m, 1H), 2.37 (s, 3H), 2.34 (s, 3H), 2.19 (s, 3H), 1.69 (brs, 2H), 1.25 (brs, 2H), 0.85 (t, 3H).

Example 20

6-(Ethyl(tetrahydro-2H-pyran-4-yl)amino)-N-((4-methoxy-6-methyl-2-oxo-1,2-dihydro pyridin-3-yl)methyl)-3,5-dimethylbenzofuran-4-carboxamide 20

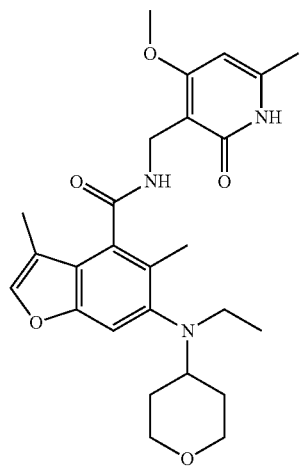

In accordance with the synthetic route of Example 19, the starting material 3-bromopropyne used in step 5 was replaced with 1-bromopropan-2-one, accordingly, the title compound 20 (17 mg, yield 11%) as a white solid was prepared.

MS m/z (ESI): 468.3 [M+1]

$^1$H NMR (400 MHz, CDCl$_3$) δ 11.22 (s, 1H), 7.27 (s, 1H), 7.21 (s, 1H), 6.94 (s, 1H), 5.94 (s, 1H), 4.61-4.62 (brd, 2H), 3.92-3.95 (brd, 2H), 3.89 (s, 3H), 3.29 (dt, 2H), 3.16-3.20 (m, 3H), 2.29 (s, 3H), 2.22 (s, 3H), 2.11 (s, 3H), 1.65 (brs, 2H), 1.31 (brs, 2H), 0.86 (t, 3H).

Example 21

6-(Ethyl(tetrahydro-2H-pyran-4-yl)amino)-N-((4-methoxy-6-methyl-2-oxo-1,2-dihydro pyridin-3-yl)methyl)-5-(trifluoromethyl)benzofuran-4-carboxamide

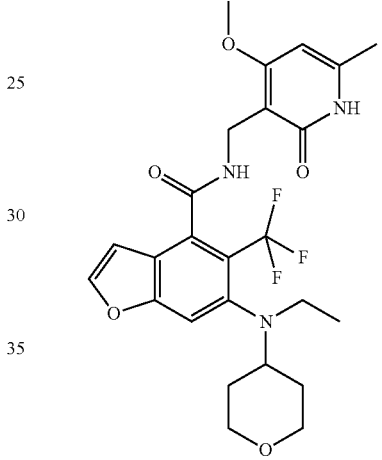

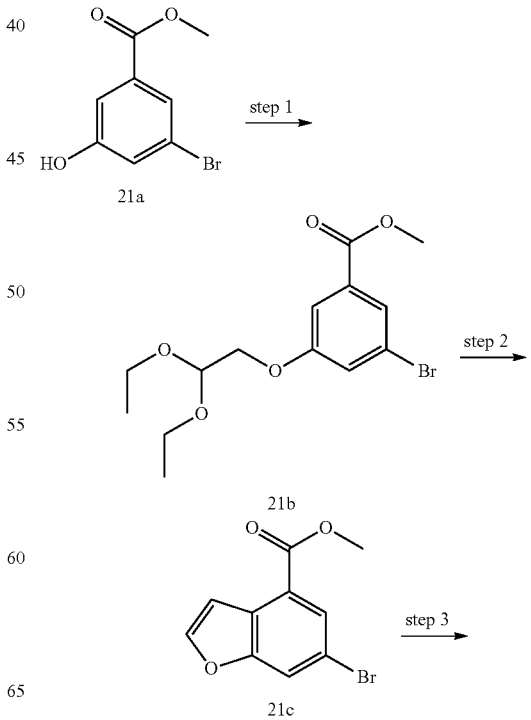

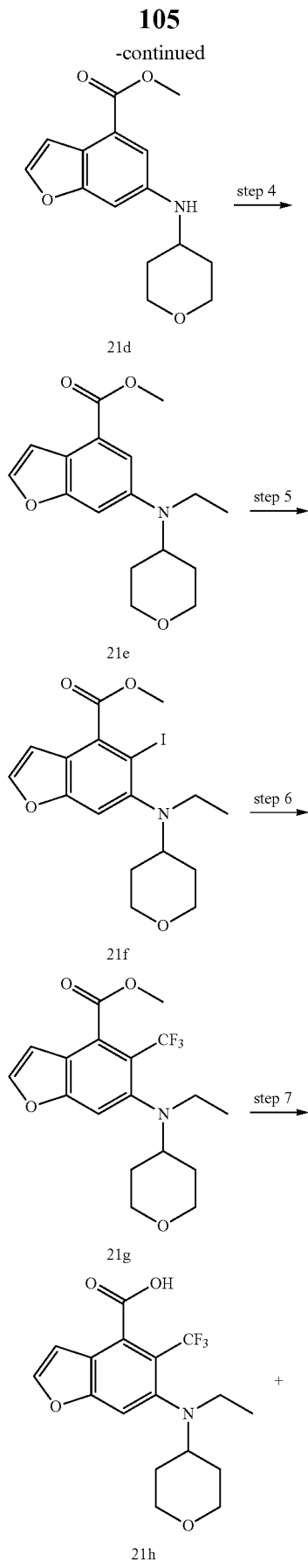

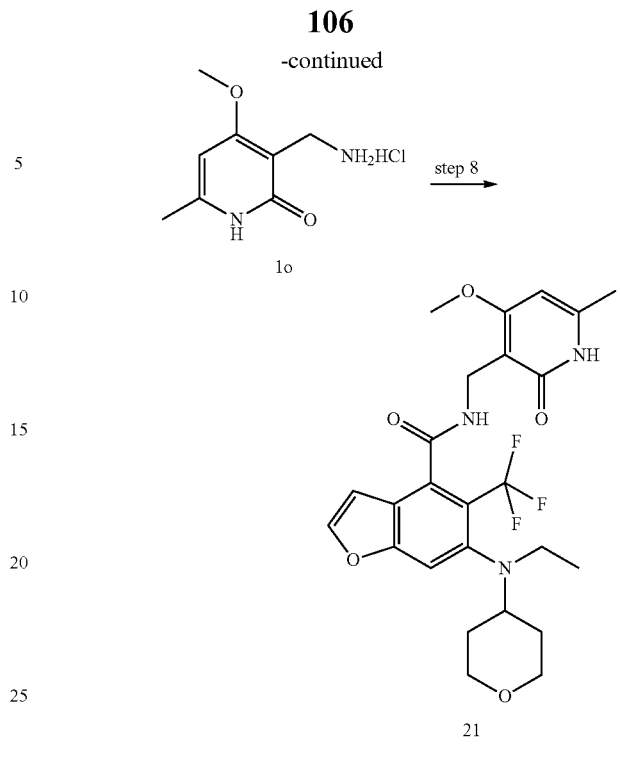

Step 1

Methyl 3-bromo-5-(2,2-diethoxyethoxy)benzoate 21b

Methyl 3-bromo-5-hydroxybenzoate 21a (1.9 g, 8.23 mmol, prepared by a method disclosed in "*Journal of Medicinal Chemistry*, 2013, 56(8), 3217-3227") was dissolved in 60 mL of N,N-dimethylformamide, then 2-bromo-1,1-diethoxyethane (3.23 g, 16.4 mmol) and cesium carbonate (5.35 g, 16.4 mmol) were added. The reaction system was stirred for 4 hours at 95° C. After the reaction was completed, the reaction solution was poured into ice water, extracted with ethyl acetate (50 mL×3), dried over anhydrous sodium sulfate, and filtered. The filtrate was concentrated under reduced pressure to obtain the crude title compound 21b (3.5 g) as a yellow oil, which was used directly in the next step without further purification.

Step 2

Methyl 6-bromobenzofuran-4-carboxylate 21c

Polyphosphoric acid (5.46 g, 16.4 mmol) was added to 20 mL of toluene. The mixture was heated to 115° C., then 40 mL of a pre-prepared solution of 21b (3.5 g, 10 mmol) in toluene were added with stirring. The mixture was stirred for 5 hours. After the reaction was completed, the mixture was poured into ice water, neutralized with saturated sodium bicarbonate solution, extracted with ethyl acetate (20 mL×3), dried over anhydrous sodium sulfate, and filtered. The filtrate was concentrated under reduced pressure, and the resulting residue was purified by silica gel column chromatography with elution system B to obtain the title compound 21c (1.08 g, yield 52%) as a yellow solid.

Step 3

Methyl 6-((tetrahydro-2H-pyran-4-yl)amino)benzofuran-4-carboxylate 21d

Compound 21c (1.08 g, 4.25 mmol), tetrahydro-2H-pyran-4-amine (0.644 g, 6.38 mmol), tris(dibenzylideneacetone)dipalladium (393 mg, 0.43 mmol), (±)-2, 2'-bis-bis(diphenylphosphino)-1,1'-binaphthalene (267 mg, 0.43 mmol) and cesium carbonate (2.6 g, 8.5 mmol) were dissolved in 60 mL of toluene. The mixture was stirred for 36 hours under a nitrogen atmosphere. After the reaction was completed, the reaction solution was poured into ice water, extracted with ethyl acetate (30 mL×3), dried over anhydrous sodium sulfate, and filtered. The filtrate was concentrated under reduced pressure, and the resulting residue was purified by silica gel column chromatography with elution system B to obtain the title compound 21d (200 mg, yield 17%) as a yellow solid.

Step 4

Methyl 6-(ethyl(tetrahydro-2H-pyran-4-yl)amino)benzofuran-4-carboxylate 21e

Compound 21d (200 mg, 0.727 mmol), acetaldehyde (160 mg, 3.64 mmol) and 0.2 mL of acetic acid were dissolved in 4 mL of methanol. After stirring for 24 hours, the mixture was cooled down to below 0° C. Sodium cyanoborohydride (227 mg, 3.6 mmol) was added, and the mixture was naturally warmed up to room temperature. The reaction was monitored by TLC until most of the starting materials disappeared. After the reaction was completed, the reaction solution was cooled down to 0° C., and 20 mL of saturated sodium bicarbonate solution were added to quench the reaction. The mixture was extracted with ethyl acetate (10 mL×3), dried over anhydrous sodium sulfate, and filtered. The filtrate was concentrated under reduced pressure, and the resulting residue was purified by silica gel column chromatography with elution system B to obtain the title compound 21e (140 mg, yield 64%) as a yellow-green solid.

Step 5

Methyl 6-(ethyl(tetrahydro-2H-pyran-4-yl)amino)-5-iodobenzofuran-4-carboxylate 21f

Compound 21e (13 mg, 0.043 mmol) was dissolved in 2 mL of N,N-dimethylformamide, then 5 drops of trifluoroacetic acid were added, and N-iodosuccinimide (12 mg, 0.052 mL) was added at 0° C. The mixture was naturally warmed up to room temperature. The reaction was monitored by TLC until most of the starting materials disappeared. After the reaction was completed, the reaction solution was cooled down to 0° C., neutralized by saturated sodium carbonate solution, and extracted with ethyl acetate. The organic phases were combined, dried over anhydrous sodium sulfate, and filtered. The filtrate was concentrated under reduced pressure, and the resulting residue was purified by thin-layer chromatography with elution system B to obtain the title compound 21f (16 mg, yield 86%) as a yellow oil.

Step 6

Methyl 6-(ethyl(tetrahydro-2H-pyran-4-yl)amino)-5-(trifluoromethyl)benzofuran-4-carboxylate 21g

Compound 21f (16 mg, 0.0373 mmol), cuprous iodide (36 mg, 0.187 mmol) and methyl fluorosulfonyl difluoroacetate (140 mg, 0.75 mmol) were dissolved in 2 mL of N,N-dimethylformamide. The mixture was stirred for 12 hours at 80° C. under a nitrogen atmosphere. After the reaction was completed, the mixture was concentrated under reduced pressure. The resulting residue was purified by thin-layer chromatography with elution system B to obtain the title compound 21g (10 mg, yield 72%) as a yellow-green solid.

Step 7

6-(Ethyl(tetrahydro-2H-pyran-4-yl)amino)-5-(trifluoromethyl)benzofuran-4-carboxylic acid 21h

Compound 21g (10 mg, 0.027 mmol) was dissolved in 4 mL of a mixture of methanol and tetrahydrofuran (V:V=1:1), then 0.27 mL of 2N sodium hydroxide solution was added. The mixture was stirred for 4 hours at 60° C. After the reaction was completed, the mixture was concentration under reduced pressure to remove most of the solvent. Then, 2 mL of tetrahydrofuran were added to the residue at 0° C., and 1N hydrochloric acid was added to adjust the pH to 3-4. The mixture was concentrated under reduced pressure to obtain the crude title compound 21h (9 mg) as a yellow solid, which was directly used in the next step without further purification.

Step 8

6-(Ethyl(tetrahydro-2H-pyran-4-yl)amino)-N-((4-methoxy-6-methyl-2-oxo-1,2-dihydro pyridin-3-yl)methyl)-5-(trifluoromethyl)benzofuran-4-carboxamide 21

The crude 21h (9 mg, 0.025 mmol) was dissolved in 3 mL of N,N-dimethylformamide, then 2-(7-azabenzotriazol-1-yl)-N,N,N',N'-tetramethyluronium hexafluorophosphate (14 mg, 0.041 mmol) and N,N-diisopropylethylamine (17 mg, 0.135 mmol) were added. The mixture was stirred for 20 minutes, then compound 1o (8.3 mg, 0.041 mmol) was added to the the reaction solution. The mixture was stirred for 5 hours. After the reaction was completed, 20 mL of saturated sodium chloride solution were added, and the mixture was extracted with ethyl acetate (10 mL×3). The organic phases were combined, dried over anhydrous sodium sulfate, and filtered. The filtrate was concentrated under reduced pressure, and the resulting residue was purified by thin-layer chromatography with elution system A to obtain the title compound 21 (10 mg, yield 78%) as a white solid.

MS (ESI) m/z: 508.3 [M+1]

$^1$H NMR (400 MHz, CDCl$_3$) δ 7.98 (brs, 1H), 7.53 (m, 1H), 7.32 (m, 1H), 6.92 (s, 1H), 5.96 (s, 1H), 4.65 (d, 2H), 4.09-4.05 (m, 2H), 3.92 (s, 3H), 3.89-3.85 (m, 1H), 3.55-3.50 (m, 2H), 3.37 (q, 2H), 2.27 (s, 3H), 1.85-1.79 (m, 4H), 1.20 (t, 3H).

Example 22
5-Chloro-6-(ethyl(tetrahydro-2H-pyran-4-yl)amino)-N-((4-methoxy-6-methyl-2-oxo-1,2-dihydropyridin-3-yl)methyl)benzofuran-4-carboxamide
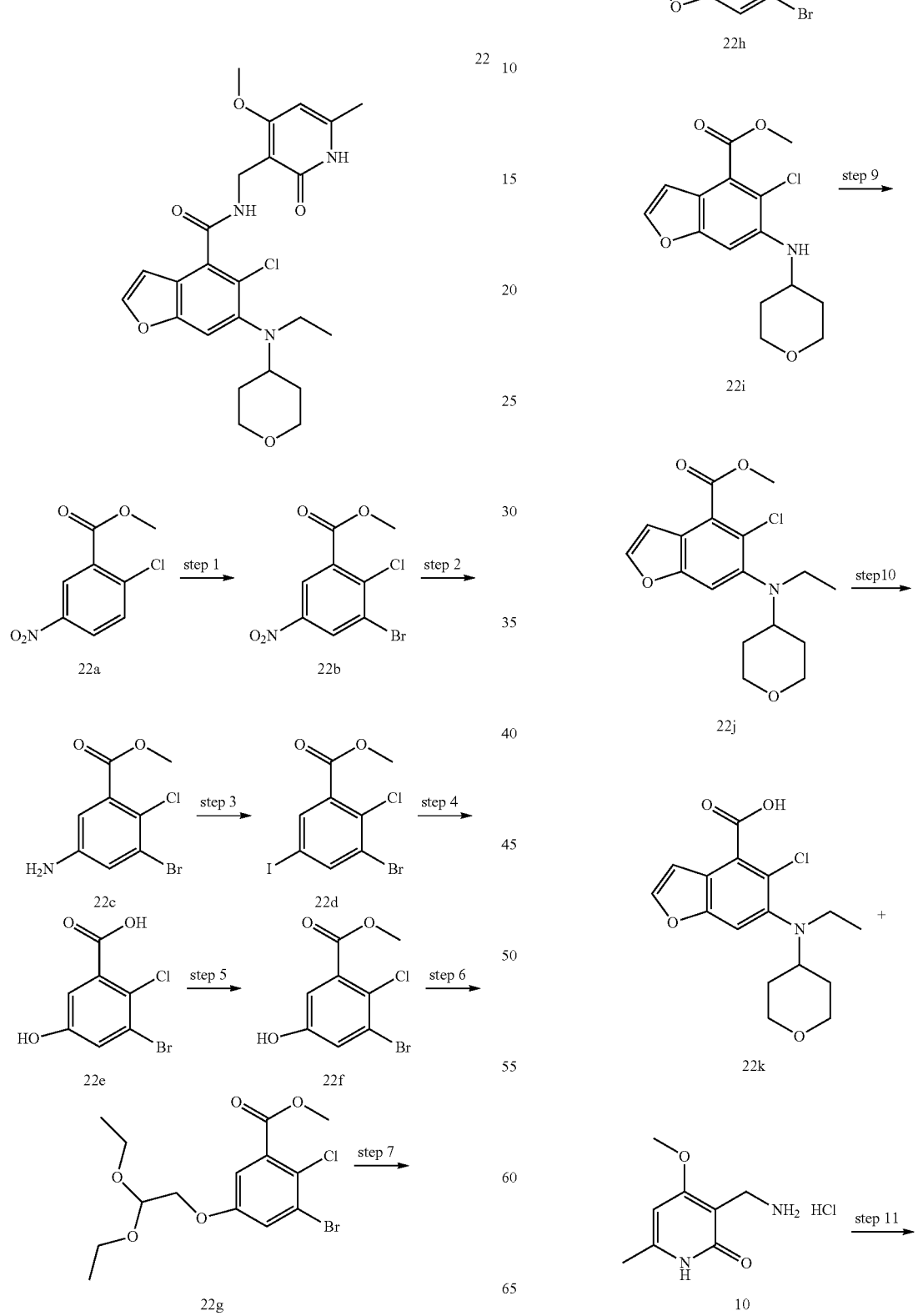

-continued

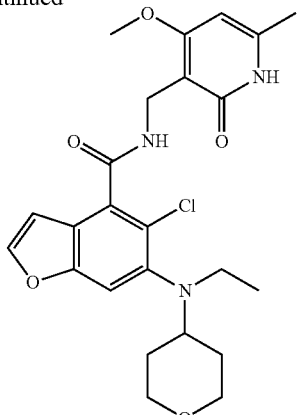

22

Step 1

Methyl 3-bromo-2-chloro-5-nitrobenzoate 22b

Methyl 2-chloro-5-nitrobenzoate (6.0 g, 27.8 mmol) was dissolved in 30 mL of concentrated sulfuric acid, then N-bromosuccinimide (5.2 g, 29.2 mmol) was added to the above reaction solution. The reaction system was stirred for 1 hour at 60° C. After the reaction was completed, the reaction system was poured into 300 mL of ice water and extracted with ethyl acetate (50 mL×3). The organic phases were combined, washed with saturated sodium bicarbonate solution (100 mL) and saturated sodium chloride solution (100 mL), dried over anhydrous sodium sulfate, and filtered. The filtrate was concentrated under reduced pressure to obtain the crude title compound 22b (7.58 g) as a light green solid, which was used directly in the next reaction without purification.

Step 2

Methyl 5-amino-3-bromo-2-chlorobenzoate 22c

The crude 22b (7.5 g, 25 mmol) was dissolved in 55 mL of a mixture of ethanol and water (V:V=8:3), and ammonium chloride (11.2 g, 203 mmol) was added. The reaction system was heated to 70° C., added with iron powder (7.1 g, 127 mmol), and stirred for 2 hours. After the reaction was completed, the mixture was filtered through a pad of celite. The filtrate was concentrated under reduced pressure, neutralized with saturated sodium bicarbonate, and extracted with ethyl acetate (50 mL×3). The organic phases were combined, washed with saturated sodium chloride solution (100 mL), dried over anhydrous sodium sulfate, and filtered. The filtrate was concentrated under reduced pressure to obtain the crude title compound 22c (5.0 g) as a yellow solid, which was used directly in the next step without further purification.

Step 3

Methyl 3-bromo-2-chloro-5-iodobenzoate 22d

The crude 22c (7.0 g, 26.5 mmol) was dissolved in 50 mL of 40% sulfuric acid and 10 mL of N,N-dimethylformamide. The mixture was cooled down to 0° C., and 5 mL of a pre-prepared solution of sodium nitrite (2.0 g, 29.1 mmol) was added dropwise. The mixture was stirred for 1 hour, then 50 mL of a pre-prepared solution of potassium iodide (22 g, 132 mmol) was added to the above reaction solution. The mixture was heated to 70° C. and stirred for 30 minutes. After the reaction was completed, the mixture was extracted with ethyl acetate (50 mL×3). The organic phases were combined, washed with water (100 mL) and saturated sodium chloride solution (100 mL), dried over anhydrous sodium sulfate, and filtered. The filtrate was concentrated under reduced pressure, and the resulting residue was purified by silica gel column chromatography with eluent system B to obtain the title compound 22d (8.0 g, yield 80%) as a light yellow solid.

Step 4

3-Bromo-2-chloro-5-hydroxybenzoic acid 22e

Compound 22d (7.0 g, 18.7 mmol) was dissolved in 10 mL of tetrahydrofuran, then 70 mL of 4N sodium hydroxide solution was added. The mixture was stirred for 2 hours at 60° C., then concentrated under reduced pressure to remove organic solvents, and cuprous oxide (7.7 g, 53.5 mmol) was added. The mixture was stirred for 1 hour at 120° C. in a microwave. After the reaction was completed, the mixture was filtered. The filtrate was neutralized with 12M hydrochloric acid, and extracted with ethyl acetate (100 mL×3). The organic phases were combined, washed with saturated sodium chloride solution (100 mL), dried over anhydrous sodium sulfate, and filtered. The filtrate was concentrated under reduced pressure to obtain the crude title compound 22e (6.0 g) as a brown oil, which was directly used in the next step without further purification.

Step 5

Methyl 3-bromo-2-chloro-5-hydroxybenzoate 22f

The crude 22e (6.0 g, 24 mmol) was dissolved in 30 mL of methanol, then 2 mL of concentrated sulfuric acid were added dropwise to the reaction solution. The reaction system was stirred for 12 hours at 60° C. After the reaction was completed, the mixture was concentrated under reduced pressure, and dissolved in 50 mL of ethyl acetate. Then, 100 mL of water were added, and the mixture was extracted with ethyl acetate (50 mL×3). The organic phases were combined, washed successively with water (100 mL) and saturated sodium chloride solution (100 mL), dried over anhydrous sodium sulfate, and filtered. The filtrate was concentrated under reduced pressure, and the resulting residue was purified by silica gel column chromatography with eluent system B to obtain the title compound 22f (3.3 g, yield 52%) as a white solid.

Step 6

Methyl 3-bromo-2-chloro-5-(2,2-diethoxyethoxy)benzoate 22g

Compound 22f (3.3 g, 12.5 mmol) was dissolved in 30 mL of N,N-dimethylformamide, then 2-bromo-1,1-diethoxyethane (2.96 g, 15 mmol) and potassium carbonate (3.4 g, 25 mmol) were added. The mixture was stirred for 3 hours at 120° C. After the reaction was completed, 150 mL of water were added, and the mixture was extracted with ethyl acetate (50 mL×3). The organic phases were combined, washed successively with water (100 mL) and saturated sodium chloride solution (100 mL), dried over anhydrous sodium sulfate, and filtered. The filtrate was concentrated under reduced pressure, and the resulting residue was purified by silica gel column chromatography with eluent system B to obtain the title compound 22 g (3.5 g, yield 74%) as a colorless oil.

Step 7

Methyl 6-bromo-5-chlorobenzofuran-4-carboxylate 22h

Polyphosphoric acid (1.0 g) was added to 15 mL of toluene. The mixture was heated to 100° C., and 10 mL of a pre-prepared solution of compound 22g (780 mg, 2.1 mmol) in toluene was added with stirring. The mixture was stirred for 4 hours. After the reaction was completed, the supernatant was separated, and the residue was added with water and extracted with ethyl acetate (20 mL×3). Ethyl acetate phase and the supernatant were combined, washed successively with saturated sodium bicarbonate solution (30 mL) and saturated sodium chloride solution (100 mL), dried over anhydrous sodium sulfate, and filtered. The filtrate was concentrated under reduced pressure, and the resulting residue was purified by thin-layer chromatography with elution system B to obtain the title compound 22h (150 g, yield 25%) as a light yellow solid.

Step 8

Methyl 5-chloro-6-((tetrahydro-2H-pyran-4-yl)amino)benzofuran-4-carboxylate 22i

Compound 22h (120 mg, 0.41 mmol), tetrahydro-2H-pyran-4-amine (60 mg, 0.6 mmol), tris(dibenzylideneacetone)dipalladium (38 g, 0.04 mmol), (±)-2,2'-bis(diphenylphosphino)-1,1'-binaphthalene (26 mg, 0.04 mmol) and cesium carbonate (405 mg, 1.24 mmol) were dissolved in 2 mL of toluene. The reaction system was stirred for 16 hours at 80° C. under an argon atmosphere. After the reaction was completed, the mixture was filtered through a pad of celite. The filtrate was concentrated under reduced pressure, and the resulting residue was purified by thin-layer chromatography with elution system B to obtain the title compound 22i (125 mg, yield 87%) as a yellow solid.

Step 9

Methyl 5-chloro-6-(ethyl(tetrahydro-2H-pyran-4-yl)amino)benzofuran-4-carboxylate 22j Compound 22i (50 mg, 0.16 mmol), acetaldehyde (36 mg, 0.81 mmol) and acetic acid (49 mg, 0.81 mmol) were added to 5 mL of 1,2-dichloroethane. The mixture was stirred for 2 hours, then sodium triacetoxyborohydride (102 mg, 0.48 mmol) was added. The mixture was stirred for 12 hours. After the reaction was completed, the reaction solution was concentrated under reduced pressure, neutralized with saturated sodium bicarbonate solution, and extracted with ethyl acetate (10 mL×3). The organic phases were combined, washed successively with water (50 mL) and saturated sodium chloride solution (50 mL), dried over anhydrous sodium sulfate, and filtered. The filtrate was concentrated under reduced pressure, and the resulting residue was purified by thin-layer chromatography with elution system B to obtain the title compound 22j (26 mg, yield 50%) as a yellow solid.

Step 10

5-Chloro-6-(ethyl(tetrahydro-2H-pyran-4-yl)amino)benzofuran-4-carboxylic acid 22k Compound 22j (51 mg, 0.16 mmol) was dissolved in 3 mL of a mixture of tetrahydrofuran and methanol (V:V=1:2), then 3 mL of 2N sodium hydroxide solution were added. The mixture was stirred for 1 hour at 60° C. After the reaction was completed, the mixture was concentrated under reduced pressure to remove organic solvents, 12 M hydrochloric acid was added to adjust the pH of the reaction solution to 5, and the mixture was extracted with ethyl acetate (10 mL×3). The organic phases were combined, washed with saturated sodium chloride solution (50 mL), dried over anhydrous sodium sulfate, and filtered. The filtrate was concentrated under reduced pressure to obtain the crude title compound 22k (42 mg) as a red-brown oil, which was used directly in the next step without further purification.

Step 11

5-Chloro-6-(ethyl(tetrahydro-2H-pyran-4-yl)amino)-N-((4-methoxy-6-methyl-2-oxo-1,2-dihydropyridin-3-yl)methyl)benzofuran-4-carboxamide 22

The crude 22k (8 mg, 0.025 mmol) was dissolved in 1 mL of N,N-dimethylformamide, then 2-(7-azabenzotriazol-1-yl)-N,N,N',N'-tetramethyluronium hexafluorophosphate (14 mg, 0.037 mmol), N,N-diisopropylethylamine (16 mg, 0.12 mmol) and compound 1o (7 mg, 0.032 mmol) were added to the above solution. The mixture was stirred for 12 hours. After the reaction was completed, 10 mL of water were added, and the reaction solution was extracted with a mixture of dichloromethane and methanol (V:V=8:1) (10 mL×3). The organic phases were combined, washed with water (50 mL) and saturated sodium chloride (50 mL), dried over anhydrous sodium sulfate, and filtered. The filtrate was concentrated under reduced pressure, and the resulting residue was purified by thin-layer chromatography with elution system A to obtain the title compound 22 (8 mg, yield 70%) as a white solid.

MS (ESI) m/z: 474.3 [M+1]

$^1$H NMR (400 MHz, DMSO-d$_6$) δ 11.46 (brs, 1H), 8.17 (s, 1H), 7.97 (s, 1H), 7.56 (s, 1H), 6.78 (s, 1H), 6.10 (s, 1H), 4.27 (d, 2H), 3.85 (brs, 2H), 3.82 (s, 3H), 3.23 (t, 2H), 3.11-3.15 (m, 3H), 2.18 (s, 3H), 1.66-1.69 (m, 2H), 1.50-1.57 (m, 2H), 0.83 (t, 3H).

Example 23

N-((4-Methoxy-6-methyl-2-oxo-1,2-dihydropyridin-3-yl)methyl)-5-methyl-6-(methyl(tetrahydro-2H-pyran-4-yl)amino)benzofuran-4-carboxamide

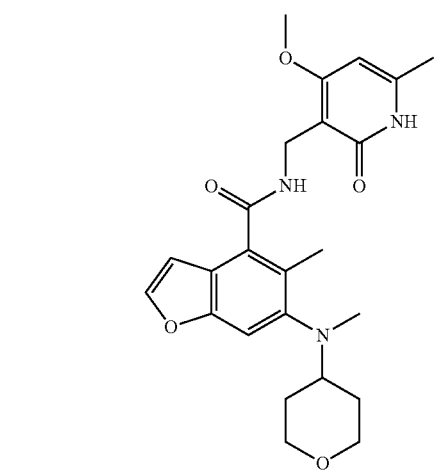

4f

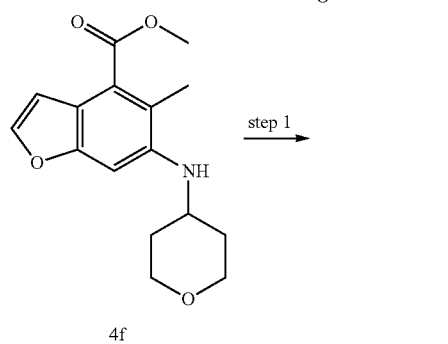

23a

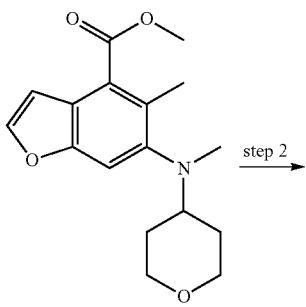

23b

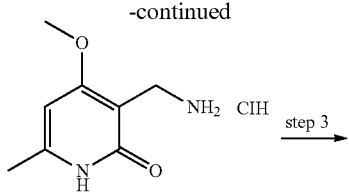

1o

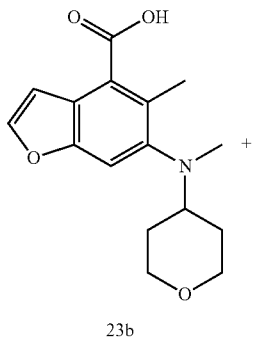

23

Step 1

Methyl 5-methyl-6-(methyl(tetrahydro-2H-pyran-4-yl)amino)benzofuran-4-carboxylate 23a Compound 4f (60 mg, 0.208 mmol) was dissolved in 5 mL of methanol, then formaldehyde (18.7 mg, 0.623 mmol) and acetic acid (62.4 mg, 1.04 mmol) were added. The mixture was stirred for 1 hour at 0° C., then warmed up to room temperature. The mixture was stirred 12 hours, then sodium cyanoborohydride (39.2 mg, 0.624 mmol) was added to the above solution. The reaction was stirred for 6 hours. After the reaction was completed, the reaction solution was concentrated under reduced pressure, then 20 mL of water were added, and extracted with ethyl acetate (10 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system B to obtain the title compound 23a (50 mg, yield 75%) as a colorless liquid.

Step 2

5-Methyl-6-(methyl(tetrahydro-2H-pyran-4-yl)amino)benzofuran-4-carboxylic acid 23b Compound 23a (50 mg, 0.165 mmol) was dissolved in 2 mL mixture of methanol and water (V:V=1:1), then sodium hydroxide (33 mg, 0.825 mmol) was added. The reaction system was stirred for 16 hours at 75° C. After the reaction was completed, the mixture was cooled down to room temperature. 2N hydrochloric acid was added to adjust the pH of the reaction solution to 3-4, and the mixture was extracted with ethyl acetate (10 mL×3). The organic phases were combined, washed with saturated sodium chloride solution (30 mL), dried over anhydrous sodium sulfate, and filtered. The resulting residue was purified by thin-layer chromatography with elution system B to obtain the title compound 23b (20 mg, yield 48%) as a colorless liquid.

Step 3

N-((4-Methoxy-6-methyl-2-oxo-1,2-dihydropyridin-3-yl)methyl)-5-methyl-6-(methyl(tetrahydro-2H-pyran-4-yl)amino)benzofuran-4-carboxamide 23

23b (15 mg, 0.052 mmol) was dissolved in 2 mL of N,N-dimethylformamide, then 2-(7-azabenzotriazol-1-yl)-N,N,N',N'-tetramethyluronium hexafluorophosphate (47.7 mg, 0.125 mmol) and N,N-diisopropylethylamine (18.3 mg, 0.14 mmol) were added. The mixture was stirred 1 hour at 0° C., then compound 1o (11.58 mg, 0.057 mmol) was added. The mixture was stirred for 12 hours. After the reaction was completed, 50 mL of water were added, and the reaction solution was extracted with a mixture of dichloromethane and methanol (V:V=10:1) (10 mL×3). The organic phases were combined, washed with saturated sodium chloride solution (30 mL), dried over anhydrous sodium sulfate, and filtered. The filtrate was concentrated under reduced pressure, and the resulting residue was purified by thin-layer chromatography with elution system A to obtain the title compound 23 (21 mg, yield 91%) as a white solid.

MS (ESI) m/z: 440.3 [M+1]

$^1$H NMR (400 MHz, CDCl$_3$) δ 12.30 (brs, 1H), 7.48 (d, 1H), 7.18 (brs, 1H), 6.74 (s, 1H), 5.94 (s, 1H), 4.64 (d, 2H), 3.95-3.98 (m, 2H), 3.91 (s, 3H), 3.30-3.36 (m, 2H), 2.96-3.01 (m, 1H), 2.65 (s, 3H), 2.39 (s, 3H), 2.19 (s, 3H), 1.69-1.73 (m, 2H), 1.45 (brs, 2H).

Example 24

6-(((1r,4r)-4-(Dimethylamino)cyclohexyl)(ethyl)amino)-N-((4-methoxy-6-methyl-2-oxo-1,2-dihydropyridin-3-yl)methyl)-5-methylbenzofuran-4-carboxamide

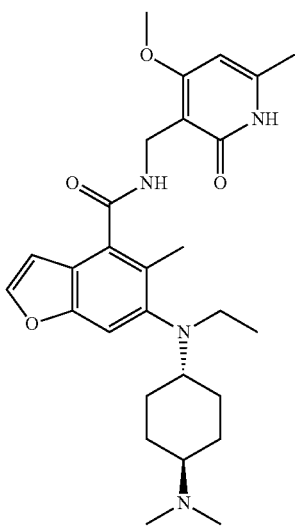

24

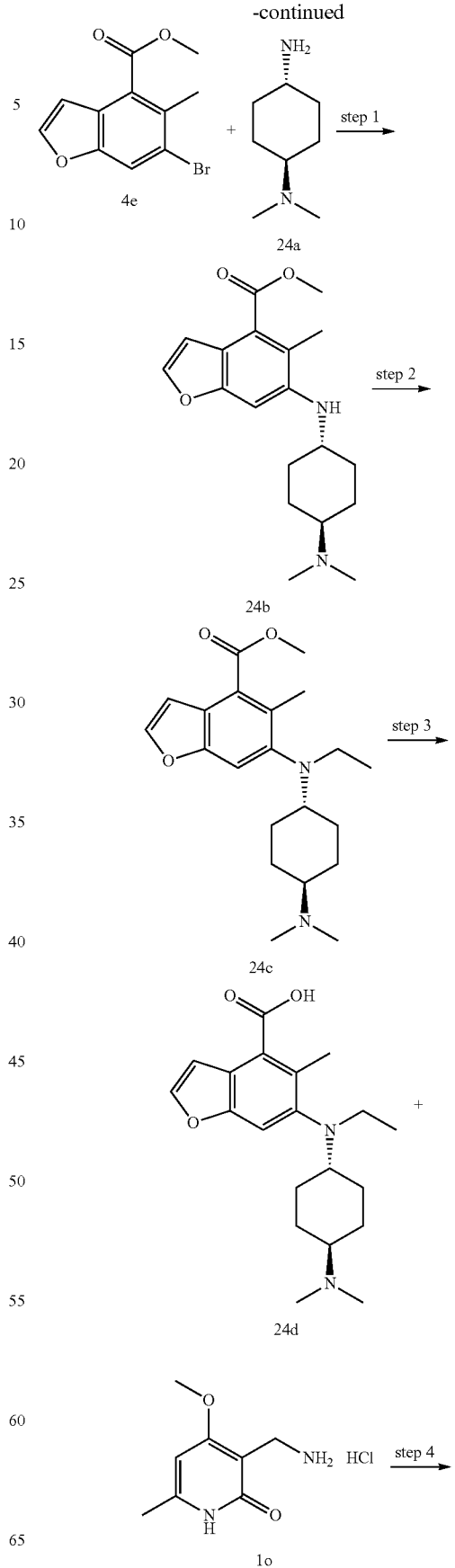

-continued

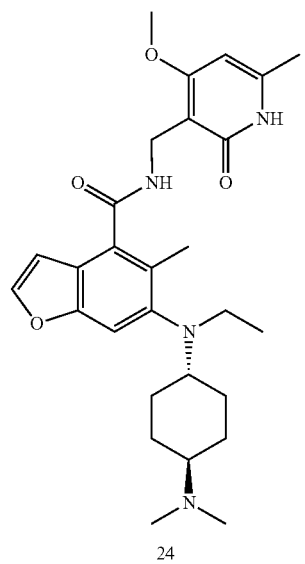

24

Step 1

Methyl 6-(((1 r,4r)-4-(dimethylamino)cyclohexyl) amino)-5-methylbenzofuran-4-carboxylate 24b Compound 4e (200 mg, 0.75 mmol), (1r, 4r)-N1,N1-dimethylcyclohexane-1,4-diamine 24a (260 mg, 1.49 mmol, prepared by a method disclosed in "*Bioorganic & Medicinal Chemistry Letters*, 2011, 21(15), 4622-4628"), tris(dibenzylideneacetone)dipalladium (137 mg, 0.15 mmol), (±)-2,2'-bis(diphenylphosphino)-1,1'-binaphthalene (140 mg, 0.22 mmol) and cesium carbonate (731.25 mg, 2.25 mmol) were dissolved in 20 mL of toluene. The reaction system was stirred under reflux for 12 hours under a nitrogen atmosphere. After the reaction was completed, 100 mL of water were added to the reaction system, and the mixture was extracted with a mixture of dichloromethane and methanol (V:V=10:1) (20 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system A to obtain the title compound 24b (15 mg, yield 6.1%) as a yellow solid.

Step 2

Methyl 6-(((1r,4r)-4-(dimethylamino)cyclohexyl) (ethyl)amino)-5-methylbenzofuran-4-carboxylate 24c Compound 24b (15 mg, 0.045 mmol), acetaldehyde (6.3 mg, 0.136 mmol) and acetic acid (13.3 mg, 0.22 mmol) were added to 3 mL of ethanol. The mixture was stirred for 1 hour at 0° C., then slowly warmed up to room temperature and stirred for 12 hours. Sodium cyanoborohydride (8.5 mg, 0.135 mmol) was added, and the mixture was stirred for 10 hours. After the reaction was completed, the reaction system was added with 20 mL of water and extracted with a mixture of dichloromethane and methanol (V:V=10:1) (10 mL×3). The organic phases were combined, washed with saturated sodium chloride (30 mL), dried over anhydrous sodium sulfate, and filtered. The filtrate was concentrated under reduced pressure to obtain the crude title compound 24c (20 mg) as a yellow solid, which was used directly in the next step without further purification.

Step 3

6-(((r,4r)-4-(Dimethylamino)cyclohexyl)(ethyl) amino)-5-methylbenzofuran-4-carboxylic acid 24d The crude 24c (20 mg, 0.056 mmol) was dissolved in 4 mL of a mixture of methanol and water (V:V=1:1), then potassium hydroxide (18.7 mg, 0.335 mmol) was added. The mixture was stirred for 12 hours at 80° C. After the reaction was completed, 2N hydrochloric acid was added to adjust the pH of the reaction solution to 3-4. After the mixture was concentrated under reduced pressure, the crude product was dissolved in 8 mL of a mixture of methylene chloride and tetrahydrofuran (V:V=1:1), and filtered. The filtrate was concentrated under reduced pressure to obtain the crude title compound 24d (25 mg) as a brown solid, which was directly used in the next step without further purification.

Step 4

6-(((1 r,4r)-4-(Dimethylamino)cyclohexyl)(ethyl) amino)-N-((4-methoxy-6-methyl-2-oxo-1,2-dihydropyridin-3-yl)methyl)-5-methylbenzofuran-4-carboxamide 24

The crude 24d (25 mg, 0.073 mmol) was dissolved in 2 mL of N,N-dimethylformamide, then 2-(7-azabenzotriazol-1-yl)-N,N,N',N'-tetramethyluronium hexafluorophosphate (41.8 mg, 0.110 mmol) and N,N-diisopropylethylamine (28 mg, 0.219 mmol) were added. The reaction was stirred for 1 hour at 0° C. Compound 1o (11.58 mg, 0.057 mmol) was added, and the mixture was stirred for 12 hours. After the reaction was completed, 2 mL of water were added to quench the reaction, and the mixture was filtered. The filtrate was concentrated under reduced pressure, and the resulting residue was purified by thin-layer chromatography with elution system A to obtain the title compound 24 (4.9 mg, yield 14%) as a white solid.

MS (ESI) m/z: 495.4 [M+1]

$^1$H NMR (400 MHz, CDCl$_3$) δ 11.62 (brs, 1H), 7.49 (s, 1H), 7.20 (brs, 1H), 6.77 (s, 1H), 5.93 (s, 1H), 5.35 (brs, 1H), 4.66 (d, 2H), 3.91 (s, 3H), 3.07 (q, 2H), 2.65-2.71 (m, 1H), 2.39 (s, 3H), 2.21 (s, 6H), 2.15 (s, 3H), 2.02 (brs, 1H), 1.85-1.93 (m, 4H), 1.32-1.43 (m, 4H), 0.86 (t, 3H).

Example 25
6-(Ethyl(1-(methylsulfonyl)piperidin-4-yl)amino)-N-((4-methoxy-6-methyl-2-oxo-1,2-dihydropyridin-3-yl)methyl)-5-methylbenzofuran-4-carboxamide
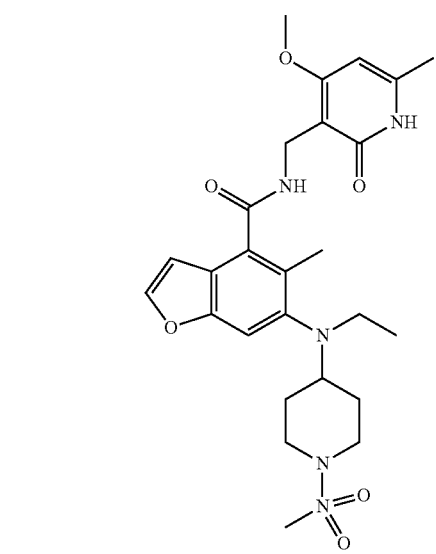
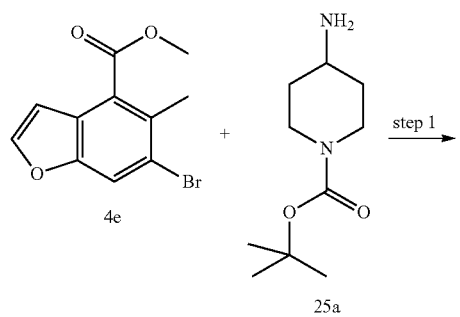
25b
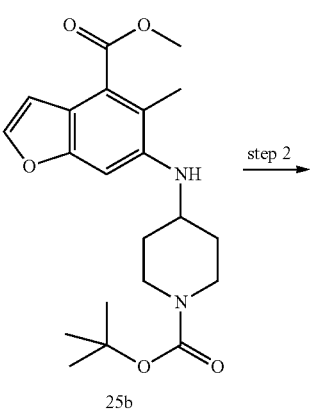
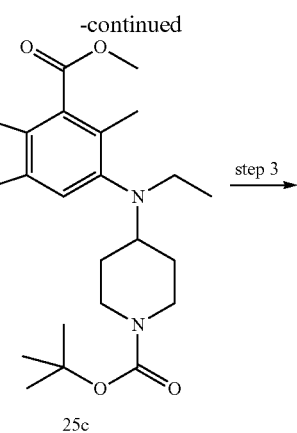
25c
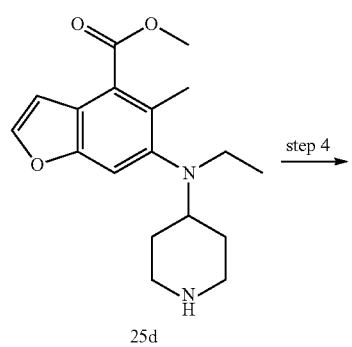
25d
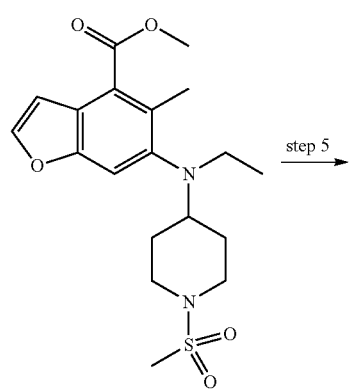
25e
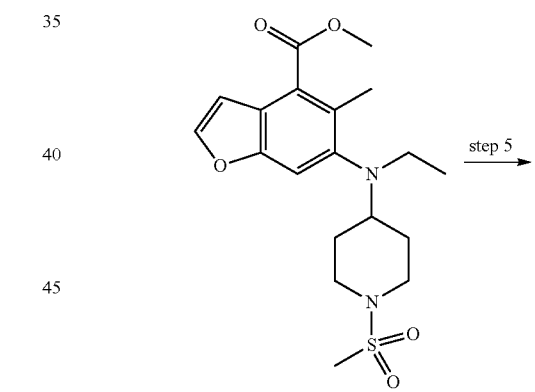
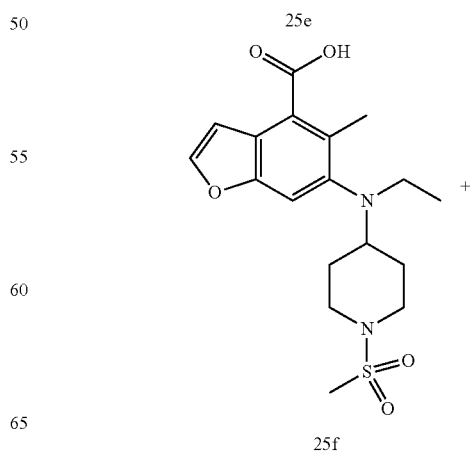
25f -continued

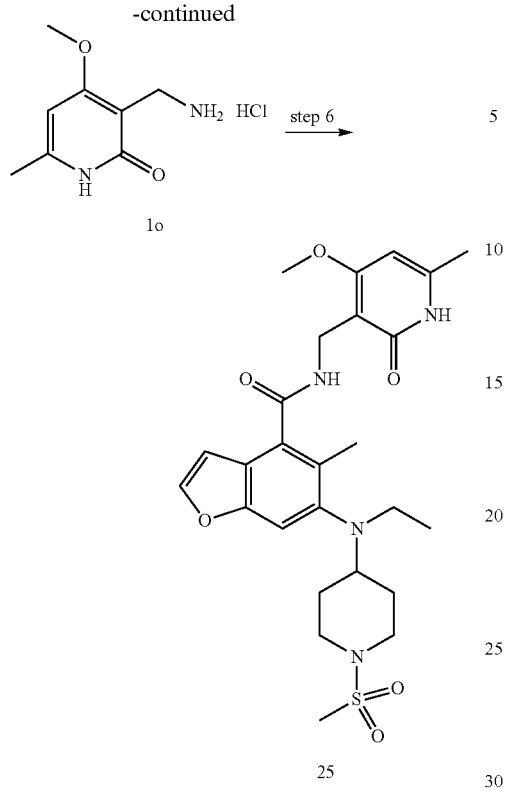

Step 1 tert-Butyl 4-((4-(methoxycarbonyl)-5-methylbenzofuran-6-yl)amino)piperidine-1-carboxylate 25b Compound 4e (810 mg, 3.02 mmol), tert-butyl 4-aminopiperidine-1-carboxylate 25a (1200 mg, 6.04 mmol, prepared by a method disclosed in "*Bioorganic & Medicinal Chemistry Letters,* 2011, 21(3), 983-988"), tris(dibenzylideneacetone)dipalladium (553 mg, 0.604 mmol), (±)-2, 2'-bis(diphenylphosphino)-1,1'-binaphthalene (564 mg, 6.04 mmol) and cesium carbonate (1.96 g, 6.04 mmol) were dissolved in 10 mL of toluene. The mixture was stirred for 72 hours at 110° C. After the reaction was completed, the mixture was filtered through celite. Then, 60 mL of ethyl acetate was added, and the mixture was washed with saturated sodium chloride (100 mL), dried over anhydrous sodium sulfate, and filtered. The filtrate was concentrated under reduced pressure, and the resulting residue was purified by silica gel column chromatography with elution system B to obtain the title compound 25b (1 g, yield 83%) as a yellow liquid.

Step 2 tert-Butyl 4-(ethyl(4-(methoxycarbonyl)-5-methylbenzofuran-6-yl)amino)piperidine-1-carboxylate 25c Compound 25b (1 g, 2.58 mmol) was dissolved in 10 mL of methanol, then acetaldehyde (360 mg, 7.73 mmol) and acetic acid (774 mg, 12.9 mmol) were added. The mixture was stirred at 0° C. for 1 hour, then warmed up to room temperature and stirred for 12 hours. Sodium cyanoborohydride (486 mg, 7.74 mmol) was added, and the mixture was stirred for 10 hours. After the reaction was completed, 50 mL of water were added to the reaction solution, and the mixture was extracted with ethyl acetate (20 mL×3). The organic phases were combined, washed with saturated sodium chloride solution (100 mL), dried over anhydrous sodium sulfate, and filtered. The filtrate was concentrated under reduced pressure, and the resulting residue was purified by silica gel column chromatography with elution system B to obtain the title compound 25c (573.8 mg, yield 62.8%) as a yellow liquid.

Step 3

Methyl 6-(ethyl(piperidin-4-yl)amino)-5-methylbenzofuran-4-carboxylate 25d

Compound 25c (184 mg, 0.58 mmol) was added to 12 mL of dichloromethane, then 3 mL of trifluoroacetic acid were added. The mixture was stirred for 2 hours. After the reaction was completed, the mixture was neutralized with saturated sodium bicarbonate solution, and extracted with ethyl acetate (20 mL×3). The organic phases were combined, dried over anhydrous sodium sulfate, and filtered. The filtrate was concentrated under reduced pressure to obtain the crude title compound 25d (156) as a brown liquid, which was directly used in the next step without further purification.

Step 4

Methyl 6-(ethyl(1-(methylsulfonyl)piperidin-4-yl)amino)-5-methylbenzofuran-4-carboxylate 25e The crude 25d (52 mg, 0.16 mmol) was added to 10 mL dichloromethane, triethylamine (64.6 mg, 0.64 mmol) was added, then methanesulfonyl chloride (37.8 mg, 0.33 mmol) was added at 0° C. The mixture was slowly warmed up to room temperature, and stirred for 12 hours. After the reaction was completed, 50 mL of water were added to the reaction solution, and the mixture was extracted with ethyl acetate (20 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system B to obtain the title compound 25e (20 mg, yield 33%) as a colorless liquid.

Step 5

6-(Ethyl(1-(methylsulfonyl)piperidin-4-yl)amino)-5-methylbenzofuran-4-carboxylic Acid 25f Compound 25e (20 mg, 0.05 mmol) was dissolved in 1 mL of methanol and 1 mL of water, then potassium hydroxide (14.2 mg, 0.25 mmol) was added. The mixture was stirred for 12 hours at 70° C. After the reaction was completed, 2N hydrochloric acid was added to adjust the pH of the reaction solution to 3-4, and the mixture was extracted with a mixture of dichloromethane and tetrahydrofuran (V:V=1:1) (10 mL×3). The organic phases were combined, washed with saturated sodium chloride solution (20 mL), dried over anhydrous sodium sulfate, and filtered. The filtrate was concentrated under reduced pressure to obtain the crude title compound 25f (16 mg) as a colorless liquid, which was directly used in the next step without further purification.

Step 6

6-(Ethyl(1-(methylsulfonyl)piperidin-4-yl)amino)-N-((4-methoxy-6-methyl-2-oxo-1,2-dihydropyridin-3-yl)methyl)-5-methylbenzofuran-4-carboxamide 25

The crude 25f (8 mg, 0.21 mmol) was dissolved in 2 mL of N,N-dimethylformamide, then 2-(7-azabenzotriazol-1-yl)-N,N,N',N'-tetramethyluronium hexafluorophosphate (12 mg, 0.0315 mmol) and N,N-diisopropylethylamine (8 mg, 0.063 mmol) were added to the above solution. The mixture was stirred for 1 hour at 0° C. Compound 1o (5.2 mg, 0.025 mmol) was added, and the reaction was stirred for 48 hours at room temperature. After the reaction was completed, 20 mL of water were added, and the mixture was extracted with a mixture of dichloromethane and methanol (V:V=10:1) (10 mL×3). The organic phases were combined, washed with saturated sodium chloride solution (20 mL), dried over anhydrous sodium sulfate, and filtered. The filtrate was concentrated under reduced pressure, and the resulting residue was purified by thin-layer chromatography with elution system A to obtain the title compound 25 (12.5 mg, yield 11%) as a white solid.

MS (ESI) m/z: 531.2 [M+1]

$^1$H NMR (400 MHz, CDCl$_3$) δ 12.5 (brs, 1H), 7.51 (d, 1H), 7.29 (s, 1H), 7.22 (brs, 1H), 6.77 (s, 1H), 5.96 (s, 1H), 4.65 (d, 2H), 3.92 (s, 3H), 3.72-3.69 (m, 2H), 3.17-3.11 (m, 1H), 3.07 (q, 2H), 2.96-2.89 (m, 2H), 2.74 (s, 3H), 2.67 (t, 2H), 2.39 (s, 3H), 2.19 (s, 3H), 1.90-1.71 (m, 4H), 0.88 (t, 3H).

Example 26

6-((1-Acetylpiperidin-4-yl)(ethyl)amino)-N-((4-methoxy-6-methyl-2-oxo-1,2-dihydropyridin-3-yl)methyl)-5-methylbenzofuran-4-carboxamide 26

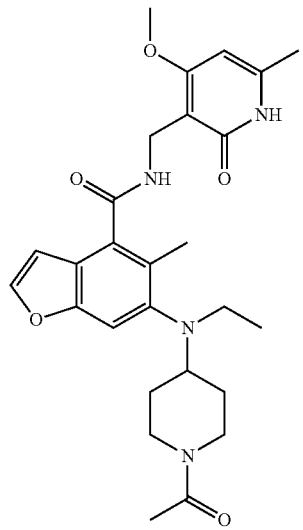

In accordance with the synthetic route of Example 25, the starting material methanesulfonyl chloride used in step 4 was replaced with acetic anhydride, accordingly, the title compound 26 (10.1 mg, yield 50%) as a white solid was prepared.

MS (ESI) m/z: 495.3 [M+1]

$^1$H NMR (400 MHz, CD$_3$OD) δ 7.76 (brs, 1H), 7.45 (brs, 1H), 6.80 (brs, 1H), 6.30 (s, 1H), 4.53 (s, 2H), 3.96 (s, 3H), 3.91 (brs, 2H), 3.36-3.30 (m, 2H), 3.23 (q, 2H), 3.11-3.05 (m, 3H), 2.41 (brs, 3H), 2.33 (s, 3H), 2.07 (s, 3H), 1.85 (brs, 2H), 1.60 (brs, 2H), 0.90 (t, 3H).

Example 27

5-Ethyl-6-(ethyl(tetrahydro-2H-pyran-4-yl)amino)-2-fluoro-N-((4-methoxy-6-methyl-2-oxo-1,2-dihydropyridin-3-yl)methyl)benzofuran-4-carboxamide

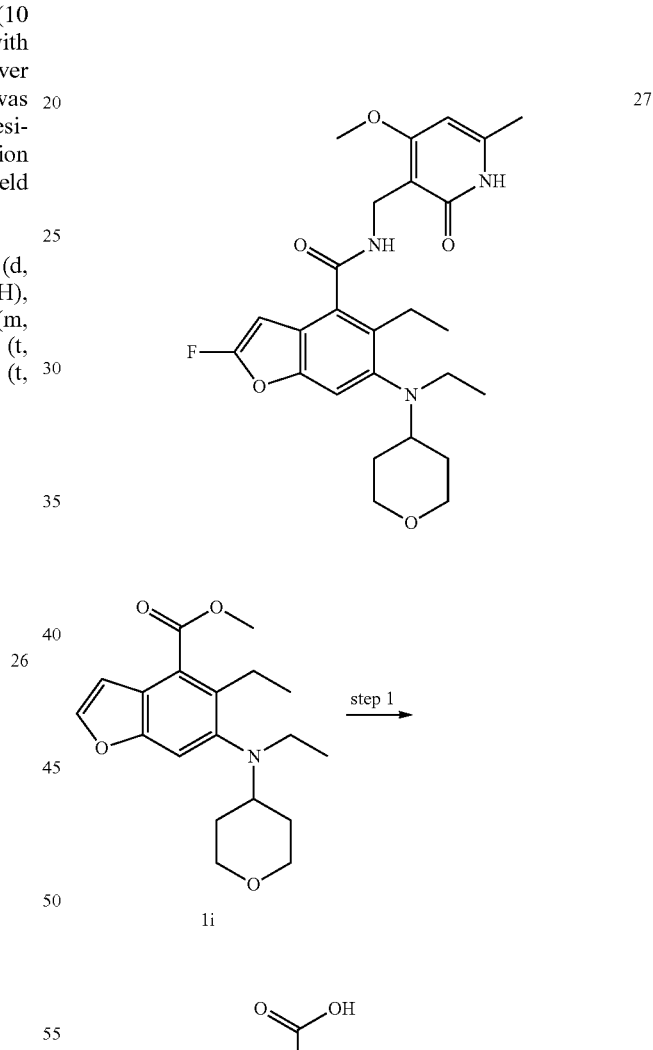

-continued

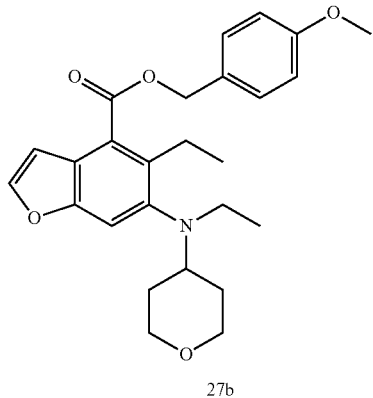

27b

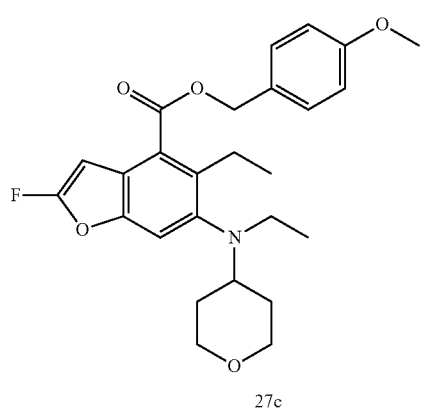

27c

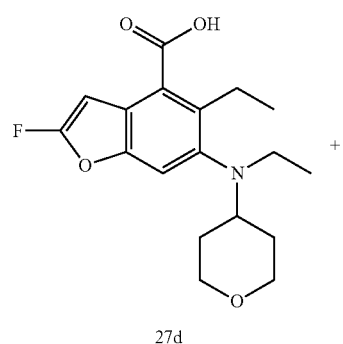

27d

+

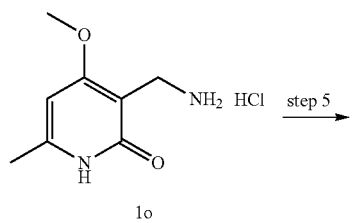

1o

-continued

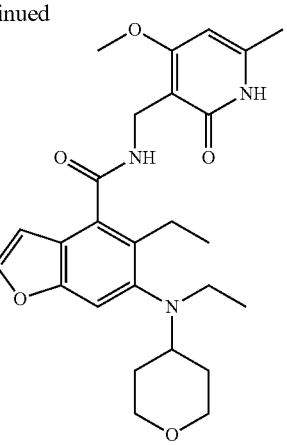

27

Step 1

5-Ethyl-6-(ethyl(tetrahydro-2H-pyran-4-yl)amino)benzofuran-4-carboxylic Acid 27a Compound 1i (260 mg, 0.79 mmol) was dissolved in 15 mL of a mixture of methanol and tetrahydrofuran (V:V=2:1), then 5 mL of 4 N sodium hydroxide solution were added. The mixture was stirred for 12 hours at 60° C. After the reaction was completed, 12 M hydrochloric acid was added to adjust the pH of the reaction solution to 4, and the mixture was extracted with ethyl acetate (20 mL×3). The organic phases were combined, washed with saturated sodium chloride solution (50 mL), dried over anhydrous sodium sulfate, and filtered. The filtrate was concentrated under reduced pressure to obtain the crude title compound 27a (220 mg) as a white solid, which was directly used in the next step within further purification.

Step 2

4-Methoxybenzyl 5-ethyl-6-(ethyl(tetrahydro-2H-pyran-4-yl)amino)benzofuran-4-carboxylate 27b The crude 27a (170 mg, 0.54 mmol) was dissolved in 15 mL of acetone, then 1-(chloromethyl)-4-methoxybenzene (168 mg, 1.07 mol, Accela) and potassium carbonate (148 mg, 1.07 mmol) were added to the above solution. The mixture was stirred for 48 hours. After the reaction was completed, the mixture was concentrated under reduced pressure, and 30 mL of water and 20 mL of ethyl acetate were successively added. Two phases were separated, and the aqueous phase was extracted with ethyl acetate (20 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system B to obtain the title compound 27b (230 mg, yield 99%) as a colorless oil.

Step 3

4-Methoxybenzyl 5-ethyl-6-(ethyl(tetrahydro-2H-pyran-4-yl)amino)-2-fluorobenzofuran-4-carboxylate 27c Compound 27b (230 mg, 0.53 mmol) was added to 8 mL of tetrahydrofuran. The mixture was cooled down to −70°

C., 0.79 mL of 2.0 M lithium diisopropylamide was added, and the mixture was stirred for 1 hour at −70° C. N-fluorodibenzenesulfonamide (182 mg, 0.58 mmol, Bepharm) was added, and the mixture was stirred for 1 hour at −70° C. After the reaction was completed, the mixture was slowly warmed up to room temperature, then 20 mL of saturated ammonium chloride solution was added to quench the reaction. The mixture was extracted with ethyl acetate (10 mL×3). The organic phases were combined, washed with saturated sodium chloride solution (20 mL), dried over sodium sulfate, and filtered. The filtrate was concentrated under reduced pressure, and the resulting residue was purified by thin-layer chromatography with elution system B to obtain the title compound 27c (17 mg, yield 7%) as a yellow oil.

Step 4

5-Ethyl-6-(ethyl(tetrahydro-2H-pyran-4-yl)amino)-2-fluorobenzofuran-4-carboxylic acid 27d Compound 27c (17 mg, 0.037 mmol) was dissolved in 3 mL of dichloromethane, then 0.5 mL of trifluoroacetic acid was added. The reaction was stirred for 1 hour at room temperature. After the reaction was completed, the mixture was concentrated under reduced pressure to to obtain the crude title compound 27d (20 mg) as a yellow oil, which was directly used in the next step without further purification.

Step 5

5-Ethyl-6-(ethyl(tetrahydro-2H-pyran-4-yl)amino)-2-fluoro-N-((4-methoxy-6-methyl-2-oxo-1,2-dihydropyridin-3-yl)methyl)benzofuran-4-carboxamide 27

The crude 27d (20 mg, 0.06 mmol) was dissolved in 3 mL of N,N-dimethylformamide, then 2-(7-azabenzotriazol-1-yl)-N,N,N',N'-tetramethyluronium hexafluorophosphate (32.6 mg, 0.85 mmol) and N,N-diisopropylethylamine (39 mg, 0.30 mmol) were added to the above solution. The mixture was stirred for 1 hour. Then, compound 1o (18 mg, 0.00 mmol) was added, and the mixture was stirred for 12 hours. After the reaction was completed, 20 mL of water were added, and the mixture was extracted with a mixture of dichloromethane and methanol (V:V=8:1). The organic phases were combined, washed with saturated sodium chloride solution, dried over anhydrous sodium sulfate, and filtered. The filtrate was concentrated under reduced pressure, and the resulting residue was purified by thin-layer chromatography with elution system A to obtain the title compound 27 (12 mg, yield 41%) as a white solid.

MS (ESI) m/z: 486.4 [M+1]

$^1$H NMR (400 MHz, DMSO-$d_6$) δ 11.48 (brs, 1H), 8.06 (t, 1H), 7.43 (s, 1H), 1.55 (d, 1H), 6.10 (s, 1H), 4.25 (d, 2H), 3.83 (brd, 2H), 3.81 (s, 3H), 3.21 (t, 2H), 3.03 (q, 2H), 3.90-3.96 (m, 1H), 2.82 (q, 2H), 2.18 (s, 3H), 1.63-1.67 (brd, 2H), 1.45-1.53 (m, 2H), 1.05 (t, 3H), 0.81 (t, 3H).

Example 28

2-Cyclopropyl-6-((cyclopropylmethyl)(tetrahydro-2H-pyran-4-yl)amino)-5-ethyl-N-((4-methoxy-6-methyl-2-oxo-1,2-dihydropyridin-3-yl)methyl)benzofuran-4-carboxamide

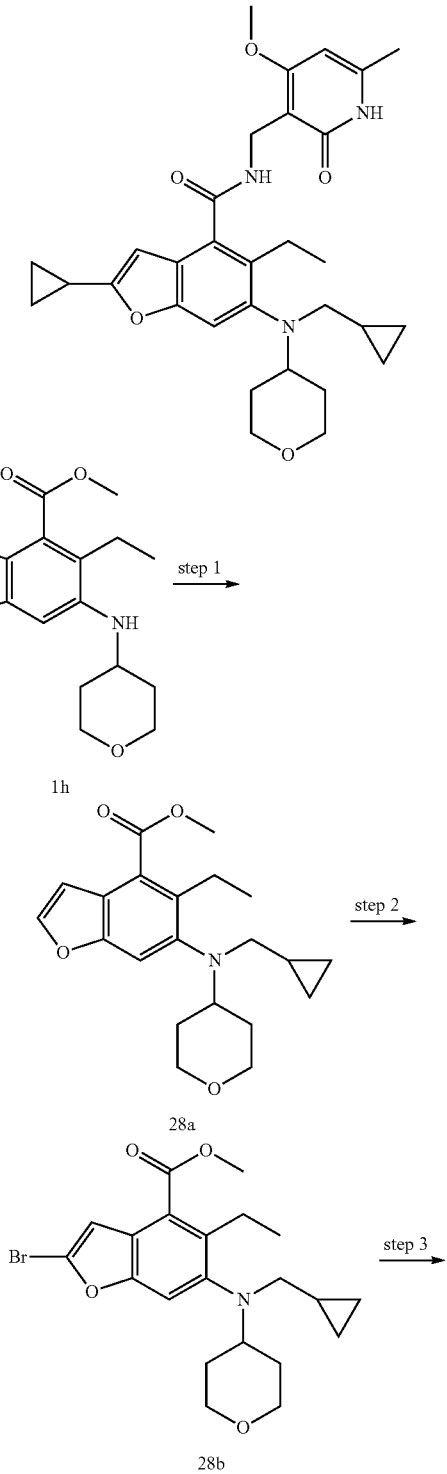

-continued

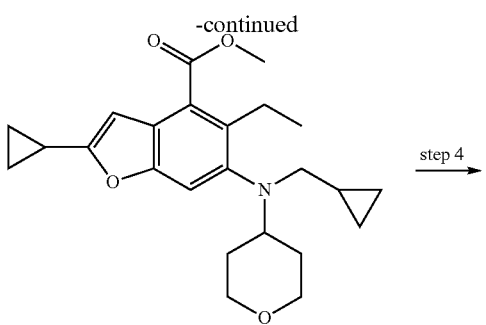

28c

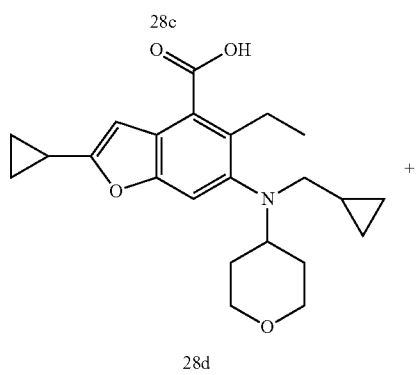

28d

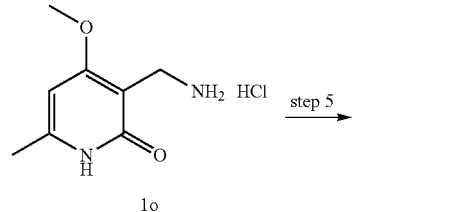

1o

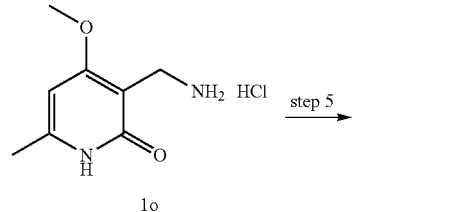

28

Step 1

Methyl 6-((cyclopropylmethyl)(tetrahydro-2H-pyran-4-yl)amino)-5-ethylbenzofuran-4-carboxylate 28a Compound 1h (950 mg, 3.03 mmol) was dissolved in 50 mL of 1,2-dichloroethane, then cyclopropanecarbaldehyde (1.1 g, 15.7 mmol) and acetic acid (940 mg, 15.7 mmol) were added to the above solution. The mixture was stirred for 12 hours, then sodium triacetoxyborohydride (1.97 g, 9.4 mmol) was added. The mixture was stirred for 3 hours. After the reaction was completed, the reaction solution was concentrated under reduced pressure, neutralized with saturated sodium bicarbonate solution, and extracted with ethyl acetate (20 mL×3). The organic phases were combined, washed successively with water (50 mL) and saturated sodium chloride solution (50 mL), dried over anhydrous sodium sulfate, and filtered. The filtrate was concentrated under reduced pressure, and the resulting residue was purified by silica gel chromatography with elution system B to obtain the title compound 28a (850 mg, yield 76%) as a light yellow oil.

Step 2

Methyl 2-bromo-6-((cyclopropylmethyl)(tetrahydro-2H-pyran-4-yl)amino)-5-ethylbenzofuran-4-carboxylate 28b Compound 28a (400 mg, 1.1 mmol) was dissolved in 15 mL of tetrahydrofuran. The mixture was cooled down to −70° C., then 1.65 mL of 2.0 M lithium diisopropylamide was added to the above solution. The mixture was stirred for 1 hour at −70° C. before 15 mL of a pre-prepared solution of 1,2-dibromo-1,1,2,2-tetrachloroethane (429 mg, 1.3 mmol) in tetrahydrofuran were added dropwise to the reaction solution. The reaction was stirred for 1 hour at −70° C. After the reaction was completed, 50 mL of saturated ammonium chloride solution were added to quench the reaction, and the mixture was extracted with ethyl acetate (20 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system B to obtain the title compound 28b (150 mg, yield 31%) as a light yellow oil.

Step 3

Methyl 2-cyclopropyl-6-((cyclopropylmethyl)(tetrahydro-2H-pyran-4-yl)amino)-5-ethylbenzofuran-4-carboxylate 28c Compound 28b (50 mg, 0.11 mmol) was dissolved in 5 mL of toluene, then cyclopropylboronic acid (20 mg, 0.23 mmol), palladium acetate (5 mg, 0.2 mmol), tricyclohexylphosphine (10 mg, 0.03 mmol) and potassium phosphate trihydrate (91 mg, 0.34 mmol) were added to the above solution. The reaction was stirred for 12 hours at 100° C. under an argon atmosphere. After the reaction was completed, the mixture was filtered through celite. The filtrate was concentrated under reduced pressure, and the resulting residue was purified by thin-layer chromatography with elution system B to obtain the title compound 28c (33 mg, yield 73%) as a colorless oil.

Step 4

2-Cyclopropyl-6-((cyclopropylmethyl)(tetrahydro-2H-pyran-4-yl)amino)-5-ethylbenzofuran-4-carboxylic acid 28d Compound 28c (33 mg, 0.08 mmol) was added to 5 mL of tetrahydrofuran and 15 mL of methanol, then 5 mL of 4 M sodium hydroxide solution were added. The reaction system was stirred for 12 hours at 60° C. After the reaction was completed, the mixture was concentrated to remove organic solvents. A small amount of water was added, 12 M hydrochloric acid was added to adjusted the pH to 3, and the mixture was extracted with ethyl acetate (10 mL×3). The organic phases were combined, washed with saturated sodium chloride solution (50 mL), dried over anhydrous sodium sulfate, and filtered. The filtrate was concentrated under reduced pressure to obtain the crude title compound 28d (25 mg) as a white solid, which was directly used in the next step without further purification.

Step 5

2-Cyclopropyl-6-((cyclopropylmethyl)(tetrahydro-2H-pyran-4-yl)amino)-5-ethyl-N-((4-methoxy-6-methyl-2-oxo-1,2-dihydropyridin-3-yl)methyl)benzofuran-4-carboxamide 28

The crude 28d (25 mg, 0.065 mmol) was dissolved in 3 mL of N,N-dimethylformamide, then 2-(7-azabenzotriazol-1-yl)-N,N,N',N'-tetramethyluronium hexafluorophosphate (47 mg, 0.098 mmol) and N,N-diisopropylethylamine (42 mg, 0.33 mmol) were added to the above solution. The mixture was stirred for 1 hour. Compound 1o (20 mg, 0.098 mmol) was added, and the mixture was stirred for 12 hours. After the reaction was completed, 20 mL of water were added to the reaction solution, and the mixture was extracted with a mixture of dichloromethane and methanol (V:V=8:1). The organic phases were combined, washed successively with water and saturated sodium chloride solution, dried over anhydrous sodium sulfate, and filtered. The filtrate was concentrated under reduced pressure, and the resulting residue was purified by thin-layer chromatography with elution system A to obtain the title compound 28 (12 mg, yield 34%) as a light yellow solid.

MS (ESI) m/z: 534.5 [M+1]

$^1$H NMR (400 MHz, DMSO-d$_6$) δ 11.48 (brs, 1H), 7.91 (s, 1H), 7.38 (s, 1H), 6.36 (s, 1H), 6.12 (s, 1H), 4.27 (brs, 2H), 3.83 (s, 3H), 3.79 (brs, 2H), 3.28 (brs, 2H), 3.17-3.23 (m, 2H), 2.96-3.00 (m, 1H), 2.83-2.86 (m, 2H), 2.19 (s, 3H), 2.06 (brs, 1H), 1.38-1.46 (m, 2H), 1.24 (brs, 2H), 1.06 (t, 3H), 0.98 (brs, 2H), 0.83 (brs, 2H), 0.64 (brs, 1H), 0.28 (brs, 2H), 0.03 (brs, 2H).

Example 29

6-(Ethyl(tetrahydro-2H-pyran-4-yl)amino)-N-((4-methoxy-6-methyl-2-oxo-1,2-dihydro pyridin-3-yl)methyl)-5-methyl-2-(trifluoromethyl)benzofuran-4-carboxamide

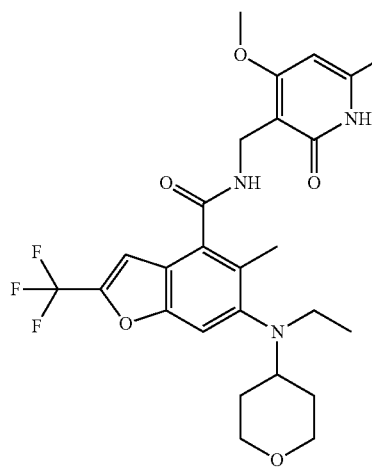

29

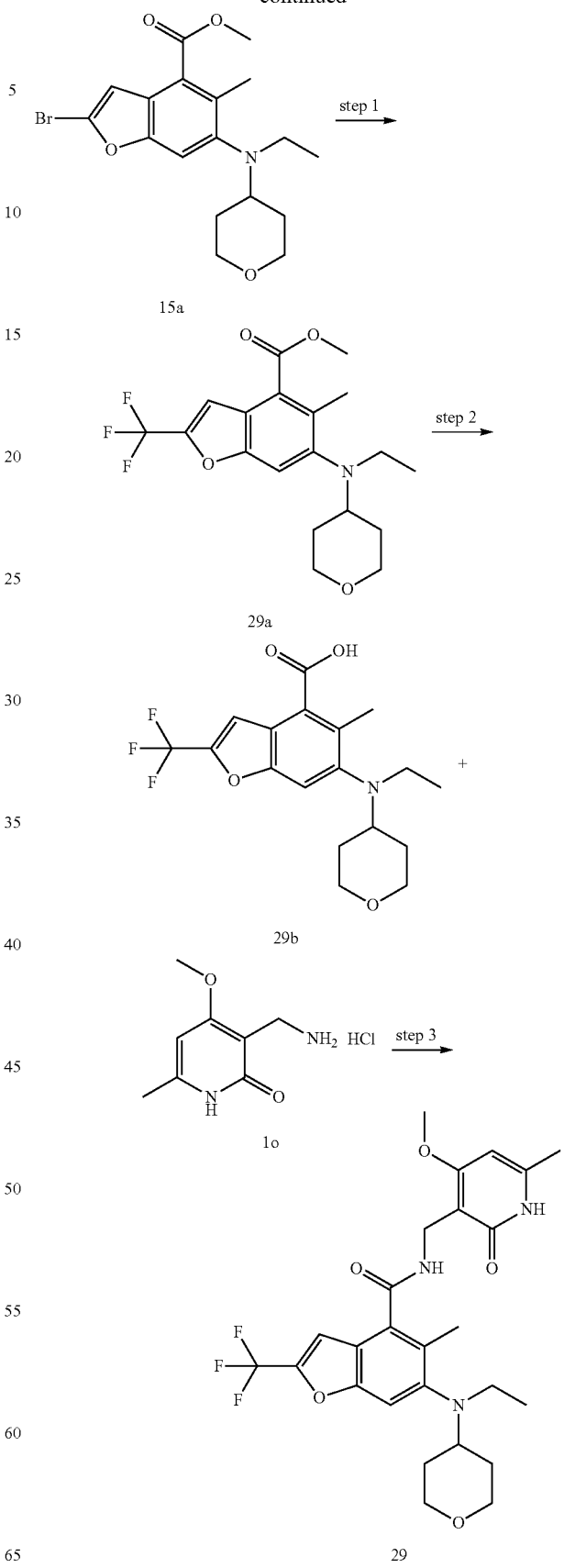

135

Step 1

Methyl 6-(ethyl(tetrahydro-2H-pyran-4-yl)amino)-5-methyl-2-(trifluoromethyl)benzofuran-4-carboxylate 29a Compound 15a (50 mg, 0.126 mmol) was dissolved in 8 mL of N,N-dimethylformamide, then methyl fluorosulfonyl difluoroacetate (500 mg, 2.52 mmol) and cuprous iodide (120 mg, 0.63 mmol) were added to the above solution. The reaction was stirred for 24 hours at 120° C. under a nitrogen atmosphere. After the reaction was completed, 50 mL of water were added to the reaction solution, and the mixture was extracted with ethyl acetate (10 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system B to obtain the title compound 29a (10 mg, yield 20.8%) as a yellow liquid.

Step 2

6-(Ethyl(tetrahydro-2H-pyran-4-yl)amino)-5-methyl-2-(trifluoromethyl)benzofuran-4-carboxylic acid 29b Compound 29a (10 mg, 0.026 mmol) was added to 2 mL of a mixture of water and methanol (V:V=1:1), then sodium hydroxide (5.16 mg, 0.129 mmol) was added. The reaction system was stirred for 16 hours at 70° C. After the reaction was completed, the reaction solution was cooled down to 5° C., 2 N hydrochloric acid was added to adjusted the pH to 3-4, and the mixture was concentrated under reduced pressure to obtain the crude title compound 29b (10 mg) as a white solid, which was directly used in the next step without further purification.

Step 3

6-(Ethyl(tetrahydro-2H-pyran-4-yl)amino)-N-((4-methoxy-6-methyl-2-oxo-1,2-dihydro pyridin-3-yl)methyl)-5-methyl-2-(trifluoromethyl)benzofuran-4-carboxamide 29

The crude 29b (10 mg, 0.027 mmol) was dissolved in 3 mL of N,N-dimethylformamide, then 2-(7-azabenzotriazol-1-yl)-N,N,N',N'-tetramethyluronium hexafluorophosphate (15.4 mg, 0.041 mmol) and N,N-diisopropylethylamine (10.5 mg, 0.081 mmol) were added. The reaction system was cooled down to 0° C. and stirred for 1 hour. Compound 1o (6.6 mg, 0.032 mmol) was added, and the mixture was stirred for 12 hours at room temperature. After the reaction was completed, 40 mL of water was added, and the mixture was extracted with a mixture of dichloromethane and methanol (V:V=8:1) (10 mL×3). The organic phases were combined, washed with saturated sodium chloride solution (50 mL), dried over anhydrous sodium sulfate, and filtered. The filtrate was concentrated under reduced pressure, and the resulting residue was purified by thin-layer chromatography with elution system A to obtain the title compound 29 (1.6 mg, yield 11.4%) as a white solid.

MS (ESI) m/z: 522.3 [M+1]

$^1$H NMR (400 MHz, CDCl$_3$) δ 7.52 (s, 1H), 7.33 (s, 1H), 7.19 (brs, 1H), 5.98 (s, 1H), 4.66 (s, 2H), 4.00-3.95 (m, 2H), 3.95 (s, 3H), 3.36-3.30 (m, 2H), 3.12 (q, 2H), 3.04-2.99 (m, 1H), 2.41 (s, 3H), 2.28 (s, 3H), 1.72 (brs, 4H), 0.89 (t, 3H).

136

Example 30

2-Cyano-6-(ethyl(tetrahydro-2H-pyran-4-yl)amino)-N-((4-methoxy-6-methyl-2-oxo-1,2-dihydropyridin-3-yl)methyl)-5-methylbenzofuran-4-carboxamide

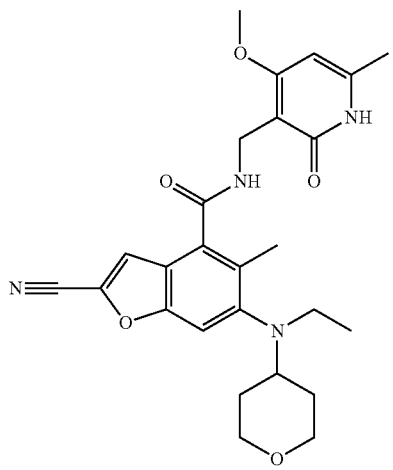

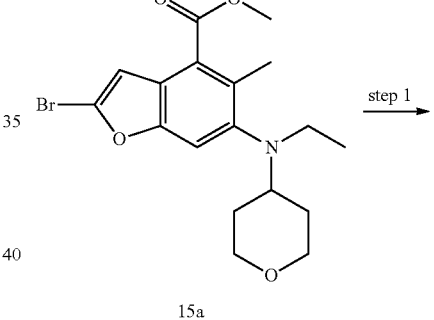

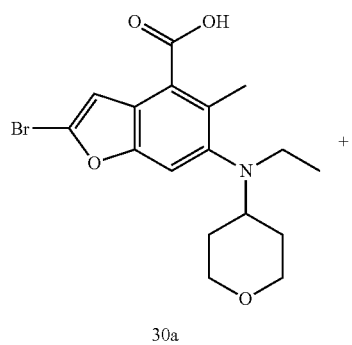

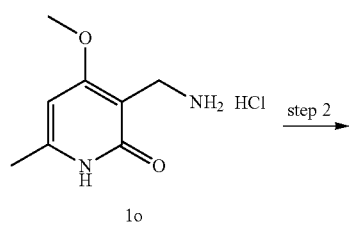

-continued

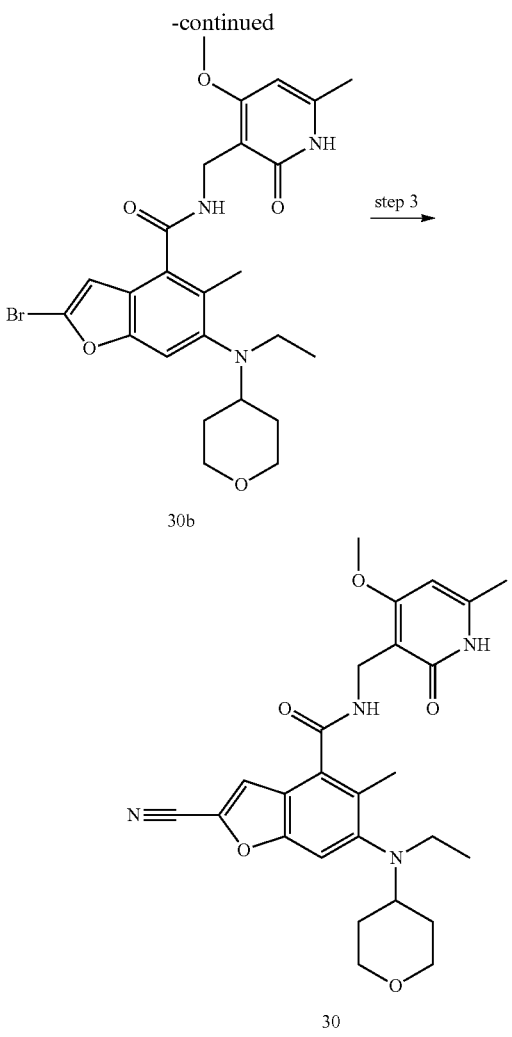

Step 1

2-Bromo-6-(ethyl(tetrahydro-2H-pyran-4-yl)amino)-
5-methylbenzofuran-4-carboxylic Acid Compound 15a (30 mg, 0.076 mmol) was added to 2 mL of a mixture of water and methanol (V:V=1:1), then sodium hydroxide (15.1 mg, 0.378 mmol) was added. The reaction system was stirred for 12 hours at 70° C. After the reaction was completed, the reaction solution was cooled down to 5° C., 2 N hydrochloric acid was added to adjust the pH to 3-4, and the mixture was concentrated under reduced pressure to obtain the crude title compound 30a (30 mg) as a white solid, which was used directly in the next step without further purification.

Step 2

2-Bromo-6-(ethyl(tetrahydro-2H-pyran-4-yl)amino)-
N-((4-methoxy-6-methyl-2-oxo-1,2-dihydropyridin-
3-yl)methyl)-5-methylbenzofuran-4-carboxamide
30b The crude 30a (30 mg, 0.078 mmol) was dissolved in 5 mL of N,N-dimethylformamide, then 2-(7-azabenzotriazol-1-yl)-N,N,N',N'-tetramethyluronium hexafluorophosphate (44.5 mg, 0.117 mmol) and N,N-diisopropylethylamine (30.2 mg, 0.234 mmol) were added to the above solution. The reaction system was cooled down to 0° C. and stirred for 1 hour. Compound 1o (6.6 mg, 0.032 mmol) was added, and the mixture was stirred for 12 hours. After the reaction was completed, 50 mL of water were added, and the mixture was extracted with a mixture of dichloromethane and methanol (V:V=8:1) (10 mL×3). The organic phases were combined, washed with saturated sodium chloride solution (20 mL), dried over anhydrous sodium sulfate, and filtered. The filtrate was concentrated under reduced pressure to obtain the crude title compound 30b (50 mg) as a yellow liquid, which was used directly in the next step without further purification.

Step 3

2-Cyano-6-(ethyl(tetrahydro-2H-pyran-4-yl)amino)-
N-((4-methoxy-6-methyl-2-oxo-1,2-dihydropyridin-
3-yl)methyl)-5-methylbenzofuran-4-carboxamide 30

The crude 30b (40 mg, 0.075 mmol) was dissolved in 5 mL of N,N-dimethylacetamide, then cuprous cyanide (13.6 mg, 0.15 mmol) and cuprous iodide (14.3 mg, 0.075 mmol) were added to the above solution. The reaction system was stirred for 1 hour at 170° C. After the reaction was completed, the mixture was filtered, and the filtrate was washed with a mixture of dichloromethane and methanol (V:V=10:1) (10 mL). The organic phases were combined, concentrated under reduced pressure, and the resulting residue was purified by thin-layer chromatography with elution system A to obtain the title compound 30 (4.7 mg, yield 12.5%) as a white solid.

MS (ESI) m/z: 479.4 [M+1]

$^1$H NMR (400 MHz, CDCl$_3$) δ 11.5 (brs, 1H), 7.55 (s, 1H), 7.26 (s, 1H), 7.16 (brs, 1H), 5.97 (s, 1H), 4.66 (s, 2H), 3.98-3.96 (m, 2H), 3.93 (s, 3H), 3.35-3.30 (m, 2H), 3.11 (q, 2H), 3.04-2.99 (m, 1H), 2.41 (s, 3H), 2.27 (s, 3H), 1.75-1.66 (m, 4H), 0.89 (t, 3H).

Example 31

6-((4,4-Difluorocyclohexyl)(ethyl)amino)-5-ethyl-N-
((4-methoxy-6-methyl-2-oxo-1,2-dihydropyridin-3-
yl)methyl)benzofuran-4-carboxamide 31

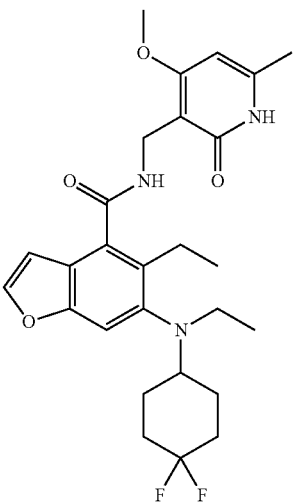

In accordance with the synthetic route of Example 24, the starting material 4e was replaced with compound 1g, and compound 24a was replaced with 4,4-difluorocyclohexylamine, accordingly, the title compound 31 (10 mg, yield 77%) as a white solid was prepared.

MS (ESI) m/z: 502.4 [M+1]

$^1$H NMR (400 MHz, DMSO-d$_6$) δ 11.47 (brs, 1H), 8.02 (t, 1H), 7.88 (d, 1H), 7.46 (s, 1H), 6.75 (d, 1H), 6.11 (s, 1H), 4.29 (d, 2H), 3.82 (s, 3H), 3.05 (brs, 2H), 2.97 (m, 1H), 2.82 (q, 2H), 2.18 (s, 3H), 1.98 (brs, 2H), 1.81 (brs, 2H), 1.73 (m, 2H), 1.58 (q, 2H), 1.08 (t, 3H), 0.83 (t, 3H).

Example 32

6-((3,3-Difluorocyclobutyl)(ethyl)amino)-5-ethyl-N-((4-methoxy-6-methyl-2-oxo-1,2-di hydropyridin-3-yl)methyl)benzofuran-4-carboxamide 32

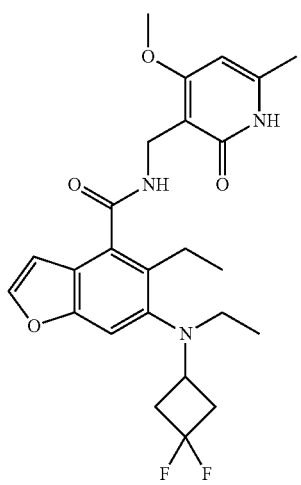

In accordance with the synthetic route of Example 24, the starting material 4e was replaced with compound 1g, and compound 24a was replaced with 3,3-difluorocyclobutanamine, accordingly, the title compound 32 (15 mg, yield 83%) as a white solid was prepared.

MS (ESI) m/z: 474.4 [M+1]

$^1$H NMR (400 MHz, DMSO-d6) δ 11.45 (brs, 1H), 8.04 (t, 1H), 7.88 (d, 1H), 7.41 (s, 1H), 6.75 (d, 1H), 6.10 (s, 1H), 4.28 (d, 2H), 3.81 (s, 3H), 3.79 (brs, 1H), 2.93 (q, 2H), 2.81 (q, 2H), 2.70 (brs, 2H), 2.25 (brs, 2H), 2.18 (s, 3H), 1.07 (t, 3H), 0.86 (t, 3H).

Example 33

6-((1,1-Dioxidotetrahydro-2H-thiopyran-4-yl)(ethyl)amino)-5-ethyl-N-((4-methoxy-6-m ethyl-2-oxo-1,2-dihydropyridin-3-yl)methyl)benzofuran-4-carboxamide 33

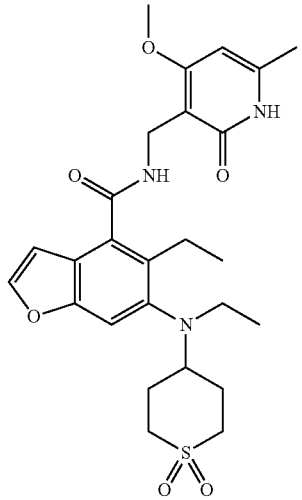

In accordance with the synthetic route of Example 24, the starting material 4e was replaced with compound 1g, and compound 24a was replaced with 4-aminotetrahydro-2H-thiopyran 1,1-dioxide, accordingly, the title compound 33 (9 mg, yield 64%) as a white solid was prepared.

MS (ESI) m/z: 516.3 [M+1]

$^1$H NMR (400 MHz, DMSO-d$_6$) δ 11.46 (brs, 1H), 8.02 (t, 1H), 7.88 (d, 1H), 7.47 (s, 1H), 6.75 (d, 1H), 6.10 (s, 1H), 4.29 (d, 2H), 3.81 (s, 3H), 2.98-3.07 (m, 5H), 3.01 (q, 2H), 2.80 (q, 2H), 2.18 (s, 3H), 2.07 (brs, 4H), 1.09 (t, 3H), 0.83 (t, 3H).

Example 34

6-((Cyclopropylmethyl)(1-(2,2,2-trifluoroethyl)piperidin-4-yl)amino)-5-ethyl-N-((4-methoxy-6-methyl-2-oxo-1,2-dihydropyridin-3-yl)methyl)benzofuran-4-carboxamide 34

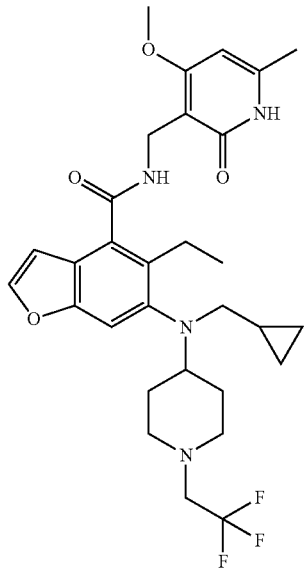

In accordance with the synthetic route of Example 25, the starting material 4e was replaced with compound 1g, the starting material acetaldehyde used in step 2 was replaced with cyclopropanecarboxaldehyde, the starting material methanesulfonyl chloride used in step 4 was replaced with trichloromethyl (2,2,2-trifluoroethyl) sulfate, accordingly, the title compound 34 (14 mg, yield 65%) as a white solid was prepared.

MS (ESI) m/z: 575.5 [M+1]

$^1$H NMR (400 MHz, DMSO-d$_6$) δ 8.01 (brs, 1H), 7.87 (s, 1H), 7.50 (s, 1H), 6.75 (s, 1H), 6.11 (s, 1H), 4.29 (d, 2H), 3.83 (s, 3H), 3.10 (q, 2H), 2.83-2.91 (m, 4H), 2.76 (brs, 1H), 2.26 (t, 2H), 2.19 (3H), 1.70 (brs, 2H), 1.49 (q, 2H), 1.24 (brs, 2H), 1.10 (t, 3H), 0.65 (brs, 1H), 0.28 (d, 2H), 0.003 (d, 2H).

Biological Assay

The present invention will be further described with reference to the following test examples, but the examples should not be considered as limiting the scope of the invention.

Test Example 1. Assay for Determining the Activity of the Example Compounds of the Present Invention on EZH2 Enzyme (A677G Mutant or Y641F Mutant)

The activity of EZH2 enzyme (with A677G mutant or Y641F mutant) was tested by the following method.

The method was used to determine the inhibitory effect of the compounds of the present invention on the activity of EZH2-A677G mutant or EZH2-Y641F mutant.

1. Experimental Materials and Instruments
   (1). EZH2-A677G (BPS Bioscience)
   (2). EZH2-Y641F (BPS Bioscience)
   (3). Histone H3 biotin labeling (AnaSpec)
   (4). S-adenosyl methionine (abbreviated as SAM, Sigma)
   (5). Histone H3K27 Me3 monoclonal antibody (Cisbio)
   (6). Streptavidin-XL665 (Cisbio)
   (7). HTRF detection buffer (Cisbio)
   (8). Multi-functional microplate reader (Tecan)
2. Experimental Procedure EZH2-A677G (or EZH2-Y641F) mutant was diluted to a concentration of 15 ng/μl by using a kinase buffer (5× buffer: 5 mg/ml BSA, 150 mM Tris-Cl, 100 mM MgCl$_2$) and added to a 384-well microtiter plate at 2 μl/well. Histone H3 biotin labeling and S-adenosyl methionine were respectively diluted to 50 nM and 50 μM with a kinase buffer, then added to a 384-well plate at 4 μl/well. The test compound was diluted with a kinase buffer (it was diluted from the highest concentration 30 μM in 10 fold concentration gradient to 7 concentration points), then added to the 384-well microtiter plate at 4 μl/well. The plate was incubated at room temperature for 2 hours. Histone H3K27 Me3 monoclonal antibody and Streptavidin-XL665 were diluted to 30 nM and 500 nM by HTRF detection buffer, then added to the 384-well microplate at 10 l/well and incubated for 1 hour. A well without an EZH2 enzyme and a compound was used as a negative control, and a well with an EZH2 enzyme but without a compound was used as a positive control. The fluorescent values were read on a multi-functional microplate reader at a emission wavelength of 620 nM and 665 nM. The compound logarithm concentration vs the inhibition percentage relative to the positive control well was plotted using GraphPad Prism, then the IC50 values were calculated.

The activity of the compounds of the present invention on enzyme EZH2-A677G was tested by the assay described above, and the IC$_{50}$ values are showed in Table 1.

TABLE 1

IC$_{50}$ of the compounds of the present invention for inhibiting the activity of enzyme EZH2-A677G

| Example No. | IC$_{50}$ (nM) |
| --- | --- |
| 1 | 6.4 |
| 2 | 5.7 |
| 3 | 38 |
| 4 | 14 |
| 5 | 1.2 |
| 6 | 7.8 |
| 7 | 3.5 |
| 8 | 6.2 |
| 9 | 5.7 |
| 10 | 1.7 |
| 11 | 5.6 |
| 12 | 10 |
| 13 | 2.9 |
| 14 | 9.6 |
| 15 | 16 |
| 16 | 31 |
| 17 | 9.9 |
| 18 | 4.0 |
| 19 | 2.9 |
| 20 | 5.9 |
| 22 | 6.5 |
| 23 | 4.8 |
| 25 | 0.9 |
| 26 | 2.9 |
| 27 | 3.5 |
| 28 | 6.8 |
| 29 | 2.7 |
| 30 | 0.8 |
| 31 | 2.7 |
| 32 | 4.0 |
| 33 | 2.7 |
| 34 | 14 |

Conclusion: The compounds of the present invention have a significant inhibitory effect on the activity of enzyme EZH2-A677G The activity of the compounds of the present invention on enzyme EZH2-Y641F was tested by the assay described above, and the IC$_{50}$ values are showed in Table 2.

TABLE 2

IC$_{50}$ of the compounds of the present invention for inhibiting the activity of enzyme EZH2-Y641F

| Example No. | IC$_{50}$ (nM) |
| --- | --- |
| 2 | 4.0 |
| 9 | 4.0 |
| 18 | 2.3 |
| 19 | 2.8 |
| 20 | 5.6 |
| 23 | 0.3 |
| 24 | 3.4 |
| 25 | 3.2 |
| 26 | 2.8 |
| 31 | 4.5 |
| 33 | 0.8 |

Test Example 2. Assay for Determining In Vitro Anti-Tumor Cell Growth Activity of the Example Compounds of the Present Invention This method was used to determinate the inhibitory effect of the compounds of the present invention on the growth activity of tumor cells (Pfeiffer or WSU-DLCL2) in vitro. Pfeiffer cells carry A677G mutant, and WSU-DLCL2 cells carry Y641F mutant.

1. Experimental Materials and Instruments
   (1). RPMI-1640, Inactivated Fetal Bovine Serum, Penicillin, Streptomycin (Life technology)
   (2). Pfeiffer and WSU-DLCL2 cell line (ATCC)
   (3). 96-well cell culture plate (Fisher Scientific)
   (4). Cell incubator (Fisher Scientific)
   (5). CellTiter-Gloluminescent cell vitality detection (Promega)
   (6). Microplate reader (Tecan)
2. Experimental Procedure The lymphoma suspension cell line (Pfeiffer or WSU-DLCL2) was cultured in a RPMI-1640 medium containing 10% inactivated Fetal Bovine Serum, 100 U/mL penicillin, and 100 μg/mL streptomycin, and incubated in an incubator with 5% carbon dioxide at 37° C. under a saturated humidity condition, and passaged every 3-4 days.

A cell sudpension was prepared with a fresh cell medium, added to a 96-well cell culture plate at 8000 cells/well (Pfeiffer) or 2000 cells/well (WSU-DLCL2), and incubated in 5% carbon dioxide at 37° C. incubator overnight. On the day of the experiment, the EZH2 test compounds (final concentration: 20000, 2000, 200, 20, 2, 0.2 nM) were added into the experimental wells for 3 parallel wells per group. A control well with the medium alone but without cells was set up to obtain the background luminescent value. The cell culture plate was incubated in an incubator with 5% carbon dioxide at 37° C. for 5 days.

After the compounds were applied to the cells for 5 days, the cell culture plate was placed at room temperature for 30 minutes, then a CellTiter-Glo reagent equal to the volume of cell culture medium was added to each well. The contents were mixed on a shaker for 10 minutes, and the fluorescent signal values were recorded. The cell growth inhibition rate was calculated, and the formula was: cell growth inhibiton rate=[(negative control control−experimental group)/(negative control group−background luminescent value)]×100%. The $IC_{50}$ values (half inhibition rate $IC_{50}$, i.e., a drug concentration that is required for 50% cell growth inhibition rate) were calculated by software from the cell growth inhibiton rate and the corresponding concentration.

The in vitro anti-tumor cell (Pfeiffer or WSU-DLCL2) growth activity of the compounds of the present invention was tested by the assay described above, and the $IC_{50}$ values are showed in Table 3 and 4.

TABLE 3

$IC_{50}$ of the compounds of the present invention for inhibiting the growth activity of tumor cells (Pfeiffer) in vitro

| Example No. | $IC_{50}$(nM) |
|---|---|
| 1 | 2 |
| 2 | 13 |
| 3 | 4 |
| 4 | 19 |
| 5 | 19 |
| 6 | 3 |
| 7 | 11 |
| 8 | 12 |
| 9 | 7 |
| 10 | 5 |
| 11 | 22 |
| 12 | 22 |
| 13 | 9 |
| 15 | 13 |
| 16 | 18 |

TABLE 3-continued $IC_{50}$ of the compounds of the present invention for inhibiting the growth activity of tumor cells (Pfeiffer) in vitro

| Example No. | $IC_{50}$(nM) |
|---|---|
| 17 | 9 |
| 18 | 20 |
| 19 | 14 |
| 23 | 68 |
| 24 | 19 |
| 25 | 15 |
| 27 | 4 |
| 28 | 78 |
| 29 | 17 |
| 30 | 17 |
| 31 | 69 |
| 32 | 18 |
| 33 | 22 |

Conclusion: The compounds of the present invention have a significant inhibitory effect on the growth of lymphoma cell (Pfeiffer) in vitro.

TABLE 4

$IC_{50}$ of the compounds of the present invention for inhibiting the growth activity of tumor cells (WSU-DLCL2) in vitro.

| Example No. | $IC_{50}$(nM) |
|---|---|
| 2 | 39 |
| 9 | 55 |
| 18 | 113 |
| 19 | 232 |
| 24 | 45 |
| 25 | 160 |
| 32 | 190 |

Conclusion: The compounds of the present invention have a significant inhibitory effect on the growth activity of lymphoma cells (WSU-DLCL2) in vitro.

Pharmacokinetics Assay

Test Example 3. Pharmacokinetics Assay of the Compounds of Examples 1, 2, 3 and 9 of the Present Invention 1. Abstract SD rats were used as test animals. The drug concentration in plasma at different time points was determined by LC/MS/MS after intragastrical administration of the compounds of Examples 1, 2, 3 and 9 to the rats. The pharmacokinetic behavior of the compounds of the present invention was studied and evaluated in rats.

2. Protocol 2.1 Test Compounds

Compounds of Examples 1, 2, 3 and 9

2.2 Test Animals 16 healthy adult Sprague-Dawley (SD) rats, half male and half female, were purchased from SINO-BRITSH SIPPR/BK LAB. ANIMAL LTD., CO, with Certificate No.: SCXK (Shanghai) 2008-0016.

2.3 Preparation of the Test Compounds

The appropriate amount of each compound was weighed, and added with 0.5% CMC-Na (containing 1% Tween 80) to prepare a 1.0 mg/mL suspension by grinding.

2.4 Administration

After an overnight fast, 16 SD rats were divided into 4 groups equally, half male and half female, and administered intragastrically the test compounds at an administration volume of 5 mL/kg.

3. Process

Blood (0.2 mL) was taken from the orbital sinus before administration and at 0.5, 1.0, 2.0, 4.0, 6.0, 8.0, 11.0, and 24.0 hours after administration. The samples were stored in heparinized tubes, and centrifuged for 10 minutes at 3,500 rpm to separate the blood plasma. The plasma samples were stored at −20° C.

The plasma concentration of the test compounds in rat plasma after intragastric administration was determined by LC-MS/MS.

4. Results of Pharmacokinetic Parameters

Pharmacokinetic parameters of the compounds of Examples 1, 2, 3 and 9 of the present invention are shown below:

| | Pharmacokinetics Parameters (5 mg/kg) | | | | | |
|---|---|---|---|---|---|---|
| Example No. | Plasma Conc. Cmax (ng/mL) | Area Under Curve AUC (ng/mL * hour) | Half-Life $t_{1/2}$ (hour) | Mean Residence Time MRT (hour) | Clearance CL/F (ml/minute/kg) | Apparent Distribution Volume Vz/F (ml/kg) |
| 1 | 88.9 ± 77.1 | 246 ± 127 | 0.80 ± 0.13 | 2.37 ± 0.18 | 390 ± 201 | 28127 ± 18370 |
| 2 | 105 ± 44.5 | 378 ± 4 2 | 2.20 ± 0.68 | 3.18 ± 0.30 | 222 ± 23.0 | 41367 ± 7914 |
| 3 | 91.5 ± 5.6 | 487 ± 12 | 2.73 ± 0.53 | 4.65 ± 0.184 | 171 ± 4.4 | 40480 ± 7967 |
| 9 | 79.1 ± 50.7 | 274 ± 180 | 0.719 ± 0.15 | 3.48 ± 0.107 | 562 ± 592 | 35102 ± 37075 |

Conclusion: The compounds of the present invention are well absorbed and have a remarkable pharmacological absorption effect.

What is claimed is:

1. A compound of formula (I):

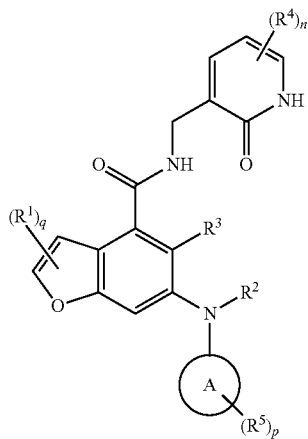

(I)

or a tautomer, mesomer, racemate, enantiomer, diastereomer, or mixture thereof, or a pharmaceutically acceptable salt thereof,
wherein:
ring A is selected from the group consisting of heterocyclyl and cycloalkyl;
each $R^1$ is identical or different and each is independently selected from the group consisting of hydrogen, halogen, alkyl, haloalkyl, alkoxy, haloalkoxy, amino, nitro, hydroxy, cyano, cycloalkyl, heterocyclyl, aryl, heteroaryl, —$OR^6$, —C(O) $R^6$, —C(O)O $R^6$, —$S(O)_mR^6$, —$S(O)_mNR^7R^8$ and —$(CH_2)_xR^a$, wherein the alkyl, haloalkyl, heterocyclyl, aryl and heteroaryl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl and heteroaryl;

$R^a$ is selected from the group consisting of halogen, cycloalkyl, heterocyclyl and —$NR^7R^8$, wherein the cycloalkyl and heterocyclyl are each independently and optionally substituted by one or more groups selected from the group consisting of alkyl, haloalkyl, halogen, amino, nitro, cyano, hydroxy, alkoxy, haloalkoxy, hydroxyalkyl, cycloalkyl, heterocyclyl, aryl, and heteroaryl;

$R^2$ is hydrogen or alkyl, wherein the alkyl is optionally substituted by one or more groups selected from the group consisting of halogen, hydroxy, cyano, cycloalkyl and heterocyclyl;

$R^3$ is selected from the group consisting of hydrogen, alkyl, halogen, cyano, alkoxy and haloalkyl;

each $R^4$ is identical or different and each is independently selected from the group consisting of hydrogen, alkyl, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$;

each $R^5$ is identical or different and each is independently selected from the group consisting of hydrogen, alkyl, oxo, halogen, haloalkyl, hydroxy, amino, alkoxy, haloalkoxy, cycloalkyl, heterocyclyl, aryl, heteroaryl, —$OR^6$, —$C(O)R^6$, —$C(O)OR^6$, —$S(O)_mR^6$, —$S(O)_mNR^7R^8$ and —$NR^7R^8$;

$R^6$ is selected from the group consisting of hydrogen, alkyl, haloalkyl, alkoxy, hydroxyalkyl, hydroxy, amino, cycloalkyl, heterocyclyl, aryl and heteroaryl;

$R^7$ and $R^8$ are identical or different and each is independently selected from the group consisting of hydrogen, alkyl, alkoxy, hydroxyalkyl, hydroxy, amino, alkoxycarbonyl, cycloalkyl, heterocyclyl, aryl and heteroaryl, wherein the alkyl, amino, cycloalkyl, heterocyclyl, aryl and heteroaryl are each independently and optionally substituted by one or more groups selected from the group consisting of alkyl, halogen, hydroxy, amino, alkoxycarbonyl, nitro, cyano, alkoxy, hydroxyalkyl, cycloalkyl, heterocyclyl, aryl and heteroaryl;

m is 0, 1 or 2;
n is 0, 1, 2 or 3;
p is 0, 1, 2, 3, 4 or 5;
q is 0, 1 or 2; and
x is 0, 1, 2 or 3.

2. The compound according to claim 1, wherein n is 2.

3. The compound according to claim 1, wherein p and q are each 0, 1 or 2.

4. The compound according to claim 1, wherein each $R^1$ is identical or different and each is independently selected from the group consisting of hydrogen, halogen, alkyl, haloalkyl, cyano, cycloalkyl, heterocyclyl and —$(CH_2)_xR^a$, wherein the alkyl and heterocyclyl are each independently and optionally substituted by one or more groups selected from the group consisting of alkyl, hydroxyalkyl and halogen; and $R^a$ is selected from the group consisting of halogen, cycloalkyl, heterocyclyl and —$NR^7R^8$, wherein the cycloalkyl and heterocyclyl are each independently and optionally substituted by one or more groups selected from the group consisting of hydroxyalkyl, alkyl and halogen; and $R^7$, $R^8$ and x are as defined in claim 1.

5. The compound according to claim 1, wherein each $R^1$ is identical or different and each is independently selected from the group consisting of hydrogen, alkyl, haloalkyl, cyano and —$(CH_2)_xR^a$, wherein x is 0, and $R^a$ is halogen or cycloalkyl.

6. The compound according to claim 1, wherein $R^2$ is alkyl optionally substituted by cycloalkyl.

7. The compound according to claim 1, wherein $R^3$ is selected from the group consisting of alkyl, halogen and haloalkyl.

8. The compound according to claim 1, wherein each $R^4$ is identical or different and each is independently selected from the group consisting of hydrogen, alkyl and alkoxy.

9. The compound according to claim 1, wherein each $R^5$ is identical or different and each is independently selected from the group consisting of hydrogen, halogen, oxo, haloalkyl, —$C(O)R^6$, —$S(O)_mR^6$ and —$NR^7R^8$.

10. The compound according to claim 1, which is a compound of formula (II):

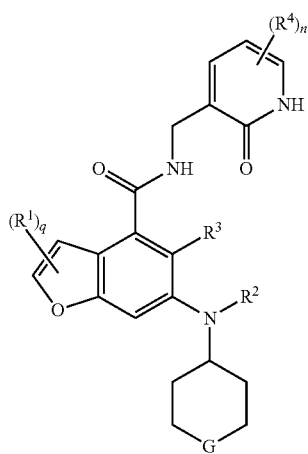

(II)

or a tautomer, mesomer, racemate, enantiomer, diastereomer, or mixture thereof, or a pharmaceutically acceptable salt thereof, wherein:

G is selected from the group consisting of $CR^bR^c$, C═O, $NR^d$, $S(O)_m$ and oxygen;

$R^b$ and $R^c$ are each independently selected from the group consisting of hydrogen, alkyl, alkoxy, halogen, amino, hydroxy, cycloalkyl, heterocyclyl, aryl, heteroaryl, —$OR^6$, —$C(O)R^6$, —$C(O)OR^6$, —$S(O)_mR^6$ and —$NR^7R^8$;

$R^d$ is selected from the group consisting of hydrogen, alkyl, cycloalkyl, haloalkyl, heterocyclyl, aryl, heteroaryl, —$C(O)R^6$, —$C(O)OR^6$ and —$S(O)_mR^6$; and $R^1$ to $R^4$, $R^6$ to $R^8$, n, m and q are as defined in claim 1.

11. The compound according to claim 1, which is a compound of formula (III):

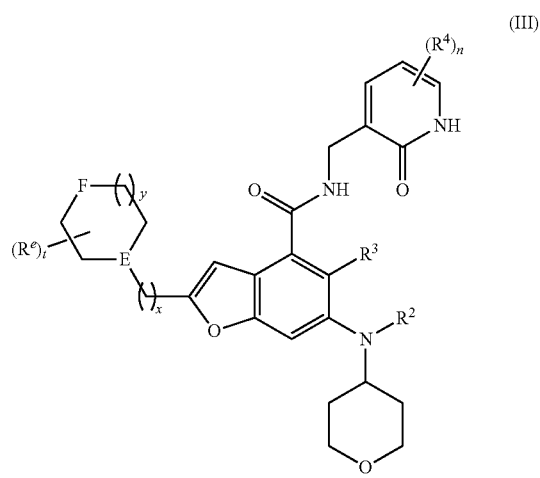

(III)

or a tautomer, mesomer, racemate, enantiomer, diastereomer, or mixture thereof, or a pharmaceutically acceptable salt thereof, wherein:

E is CH or nitrogen;

F is selected from the group consisting of $CR^bR^c$, $NR^d$ and oxygen;

$R^b$ and $R^c$ are each independently selected from the group consisting of hydrogen, alkyl, alkoxy, halogen, amino, nitro, hydroxy, cyano, cycloalkyl, heterocyclyl, aryl and heteroaryl;

$R^d$ is selected from the group consisting of hydrogen, alkyl, cycloalkyl, haloalkyl, hydroxyalkyl, heterocyclyl, aryl and heteroaryl;

each $R^e$ is identical or different and each is independently selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl;

t is 0, 1, 2, 3, 4 or 5;

x is 0, 1, 2 or 3;

y is 0, 1, 2 or 3; and $R^2$ to $R^4$, and n are as defined in claim 1.

12. The compound according to claim 11, which is a compound of formula (IV):

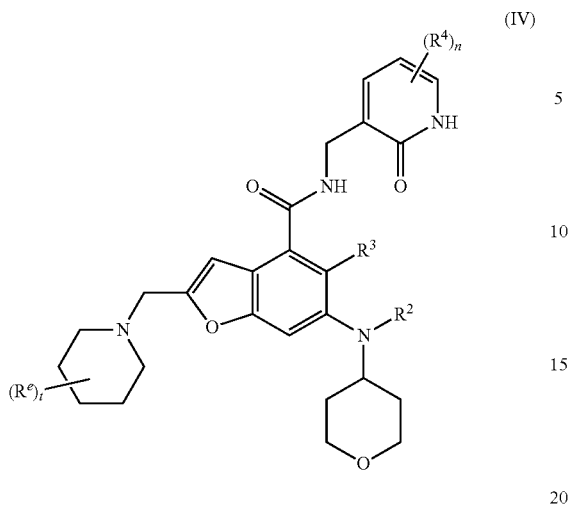

or a tautomer, mesomer, racemate, enantiomer, diastereomer, or mixture thereof, or a pharmaceutically acceptable salt thereof, wherein:

each $R^e$ is identical or different and each is independently selected from the group consisting of hydrogen, alkyl and halogen;

t is 0, 1, 2, 3, 4 or 5; and $R^2$ to $R^4$ and n are as defined in claim 11.

13. The compound according to claim 1, which is a compound of formula (V):

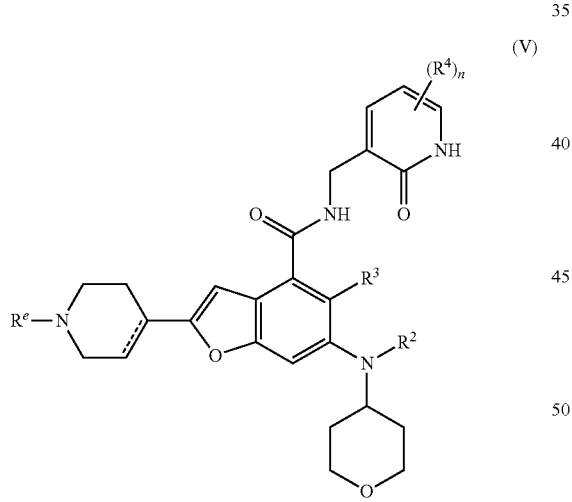

or a tautomer, mesomer, racemate, enantiomer, diastereomer, or mixture thereof, or a pharmaceutically acceptable salt thereof, wherein:

$R^e$ is selected from the group consisting of hydrogen, alkyl, haloalkyl, halogen, amino, nitro, cyano, hydroxy, alkoxy, haloalkoxy, hydroxyalkyl, cycloalkyl, heterocyclyl, aryl and heteroaryl;

$R^2$ to $R^4$ and n are as defined in claim 1, and the dotted line represents a single bond or a double bond.

14. A compound selected from the group consisting of:

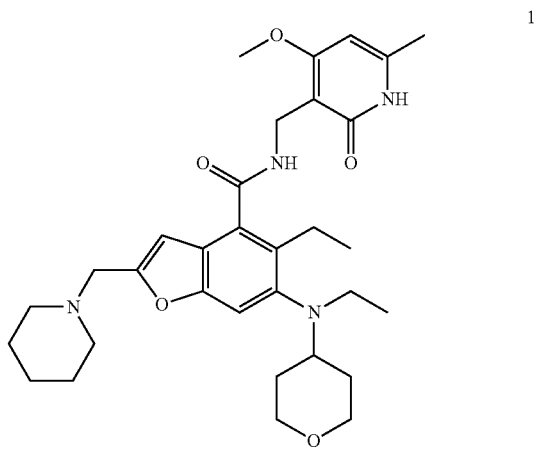

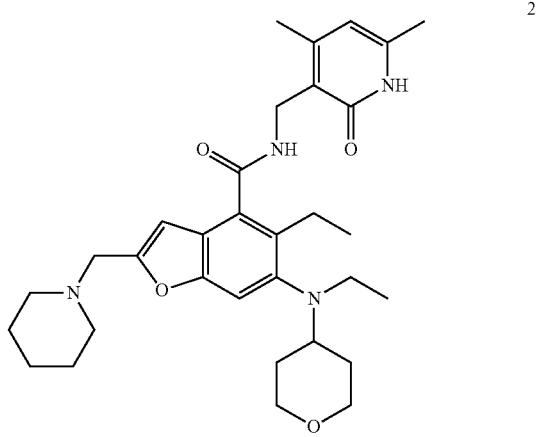 [SMILES: CCc1c(N(CC)C2CCOCC2)cc2oc(CN3CCCCC3)cc2c1C(=O)NCc1c(C)cc(C)[nH]c1=O]

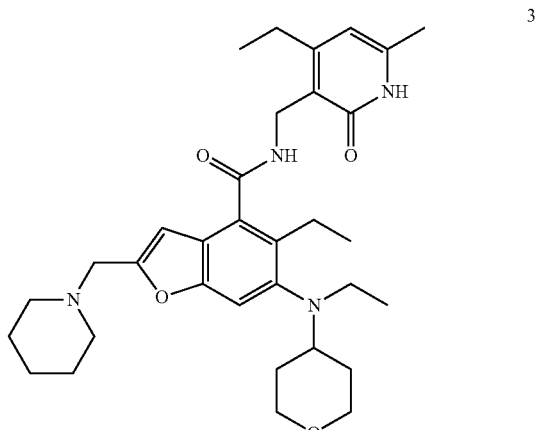

151
-continued
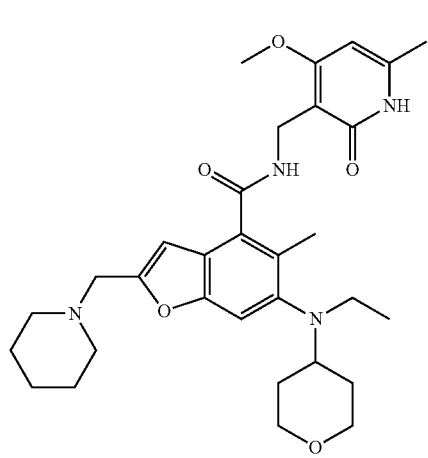
4
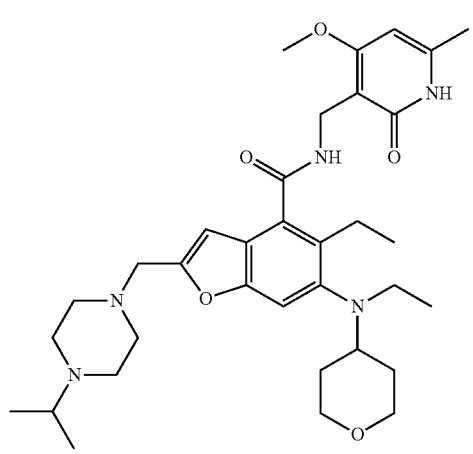
5
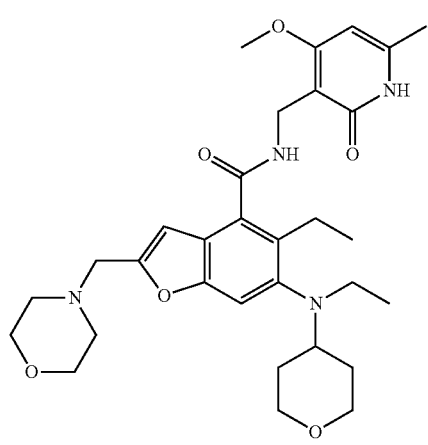
6
152
-continued
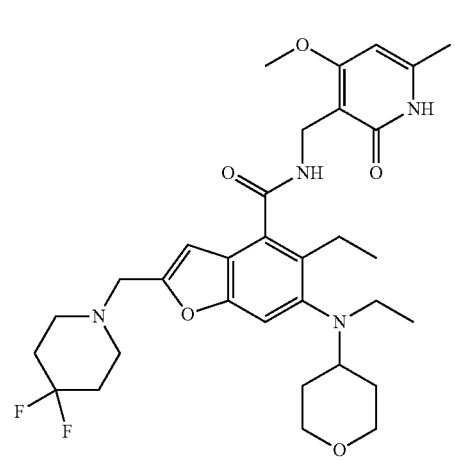
7
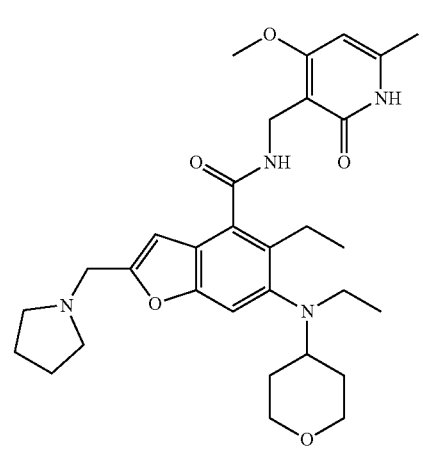
8
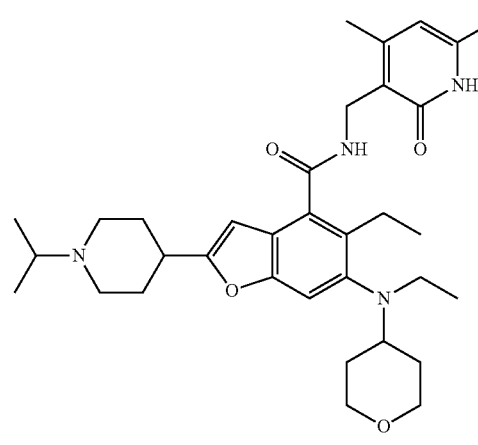
9

153
-continued
10
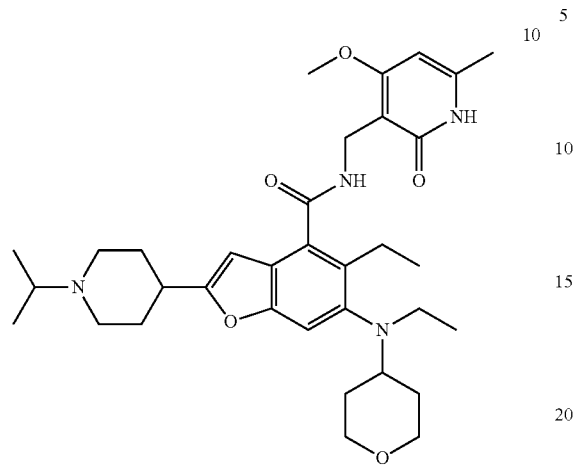
11
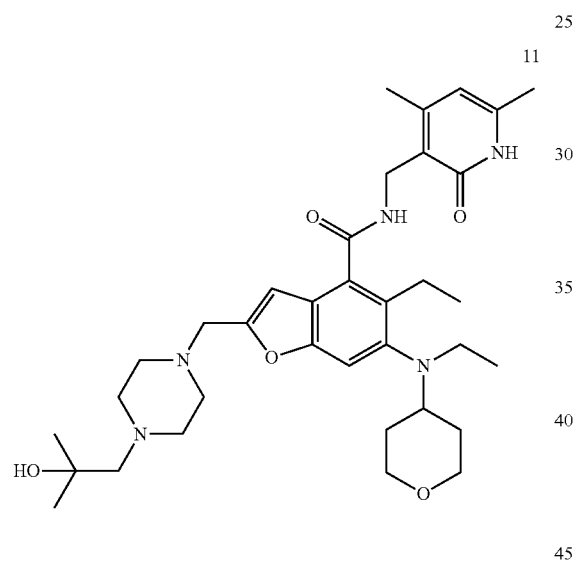
12
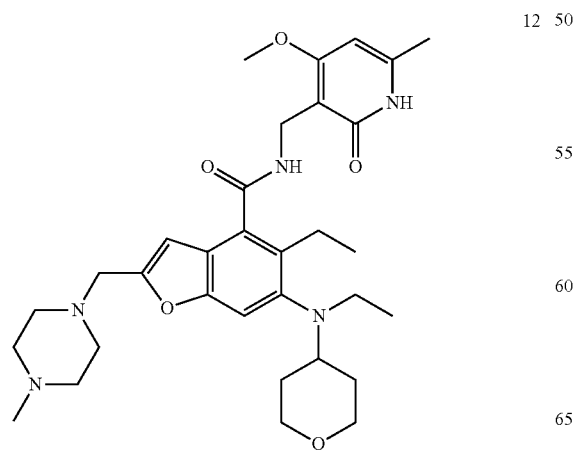
154
-continued
13
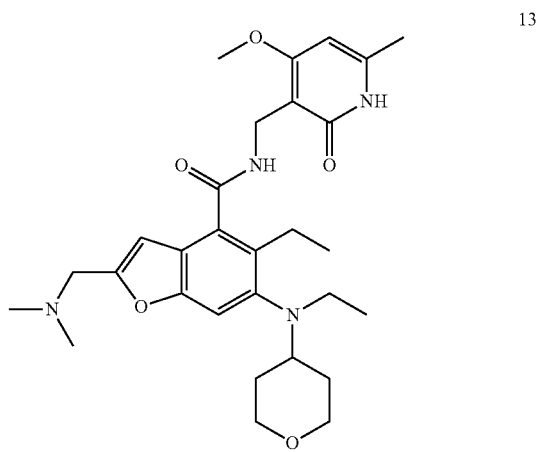
14
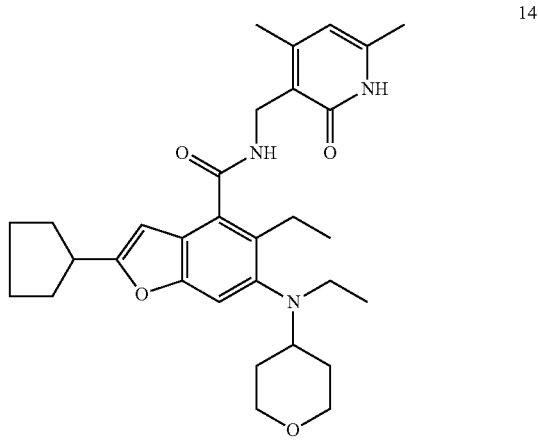
15
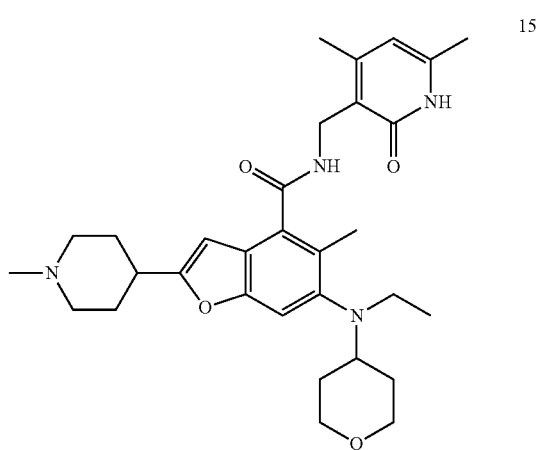

16
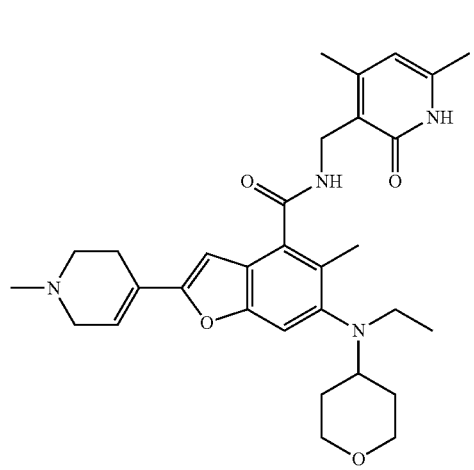
17
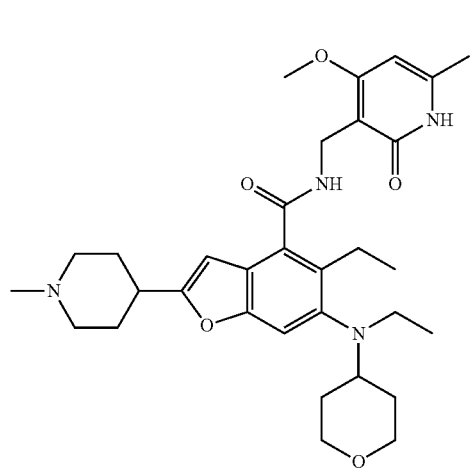
18
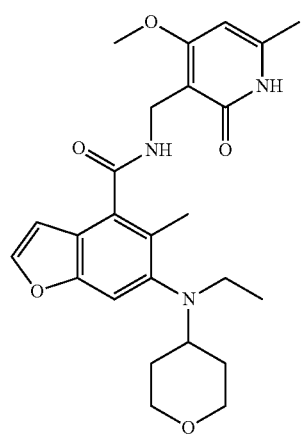
19
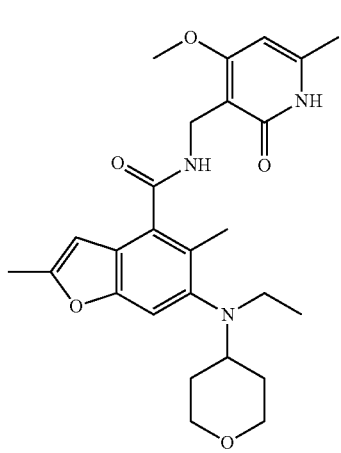
20
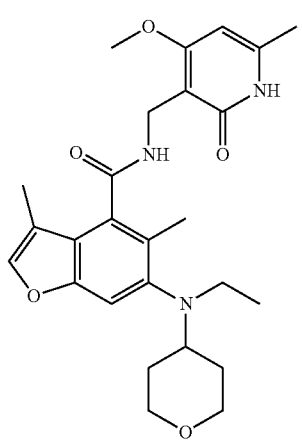
21
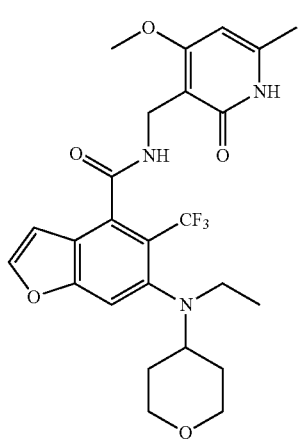

22
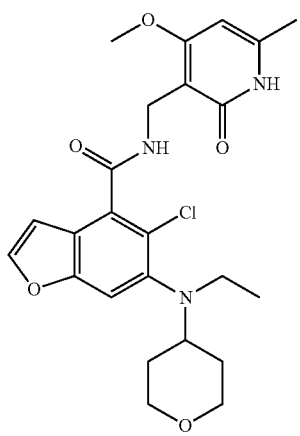
23
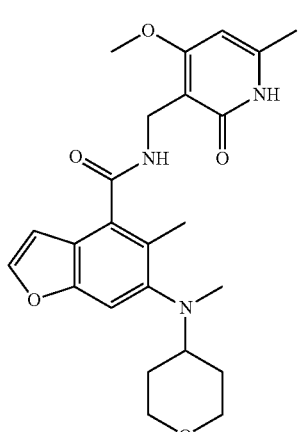
24
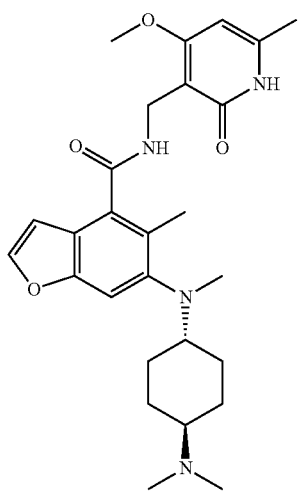
25
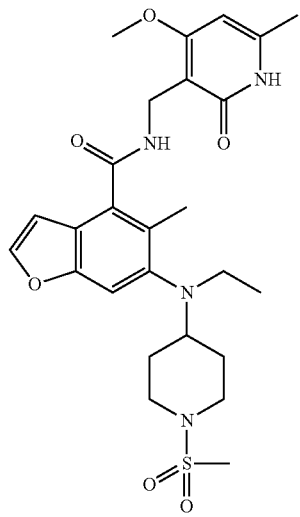
26
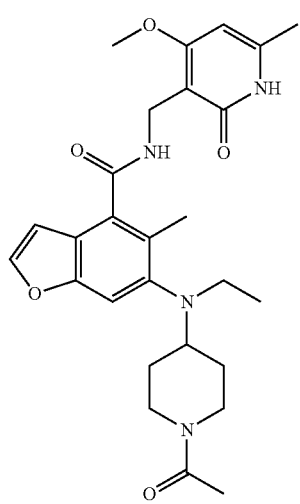
27
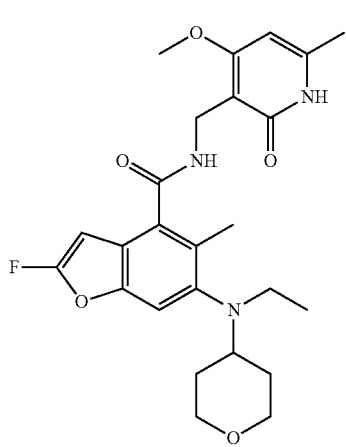

28
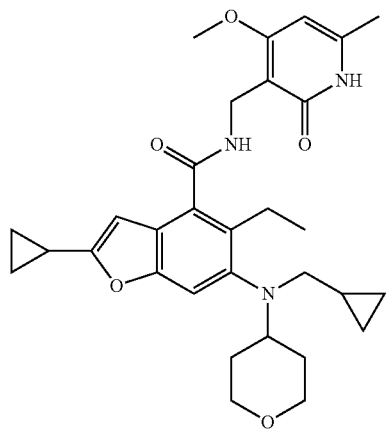
29
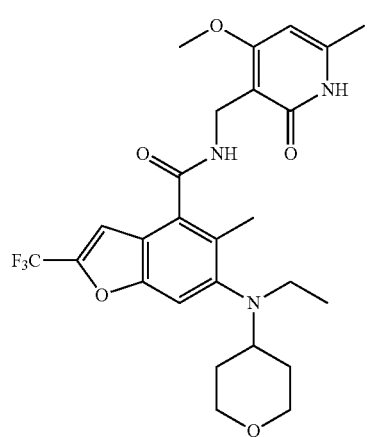
30
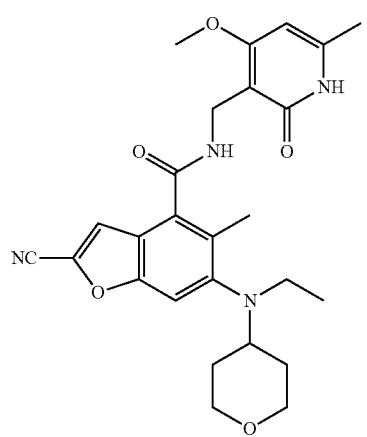
31
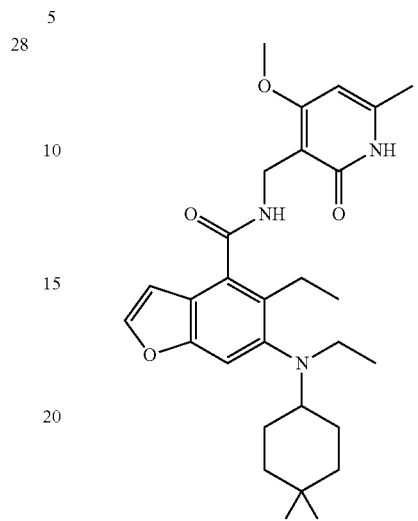
32
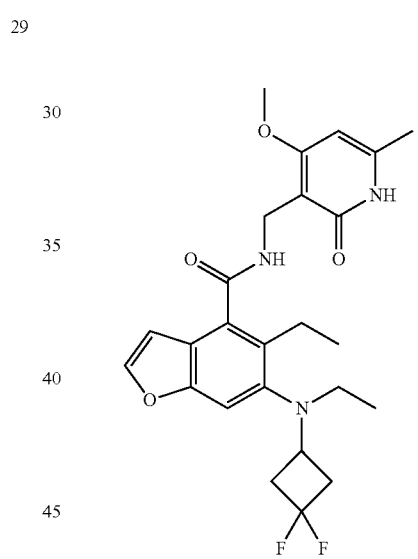
33
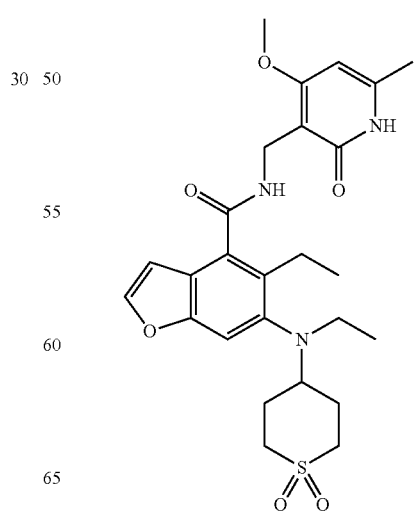
and -continued

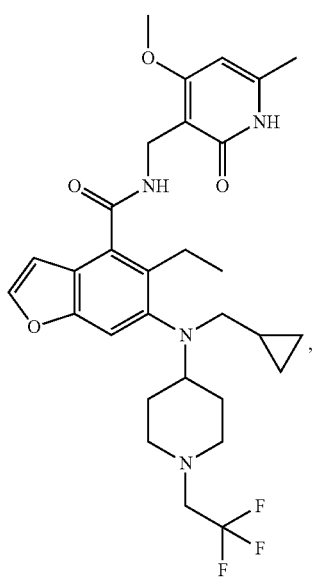

or a tautomer, mesomer, racemate, enantiomer, diastereomer, or mixture thereof, or a pharmaceutically acceptable salt thereof.

15. The compound according to claim 14, wherein the compound is

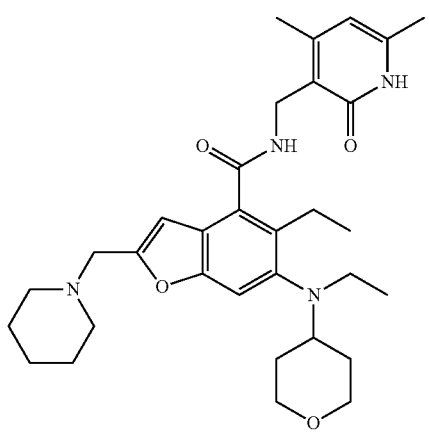

or a pharmaceutically acceptable salt thereof.

16. The compound according to claim 14, wherein the compound is

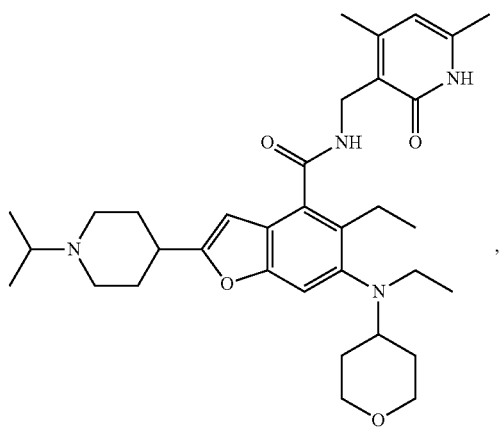

or a pharmaceutically acceptable salt thereof.

17. The compound according to claim 14, wherein the compound is

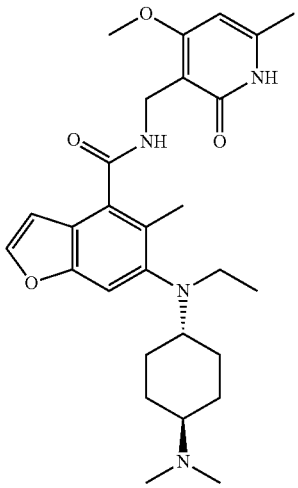

or a pharmaceutically acceptable salt thereof.

18. A pharmaceutical composition comprising a therapeutically effective amount of the compound according to claim 1, and one or more pharmaceutically acceptable carriers, diluents or excipients.

19. A method for inhibiting EZH2 in a patient in need thereof, comprising administering to the patient the pharmaceutical composition according to claim 18.

20. A method for treating a tumor or cancer, comprising administering to a patient in need thereof the pharmaceutical composition according to claim 18.

21. The method according to claim 20, wherein the tumor and cancer are selected from the group consisting of lymphoma, leukemia, breast cancer, lung cancer, prostate cancer, ovarian cancer, liver cancer, melanoma, rhabdomyosarcoma, synovial sarcoma, mesothelioma, cervical cancer, colon cancer, rectal cancer, stomach cancer, pancreatic cancer, brain cancer, skin cancer, oral cancer, bone cancer, kidney cancer, bladder cancer, fallopian tube tumor, ovarian tumor, peritoneal tumor, glioma, glioblastoma, head and neck cancer, and myeloma.

22. The method according to claim 21, wherein the leukemia is chronic myeloid leukemia, acute myeloid leukemia, or mixed lineage leukemia; and the lymphoma is non-Hodgkin's lymphoma, diffuse large B-cell lymphoma, or follicular lymphoma.

23. A process for preparing the compound of formula (I) according to claim 1, comprising:

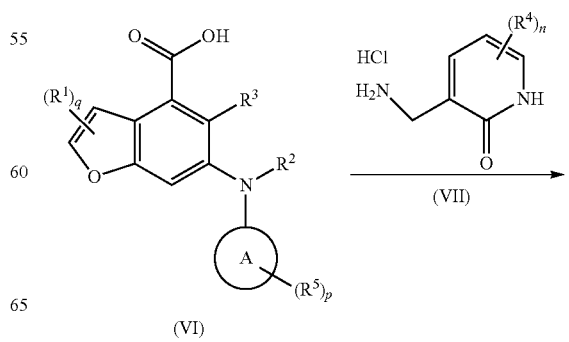

-continued
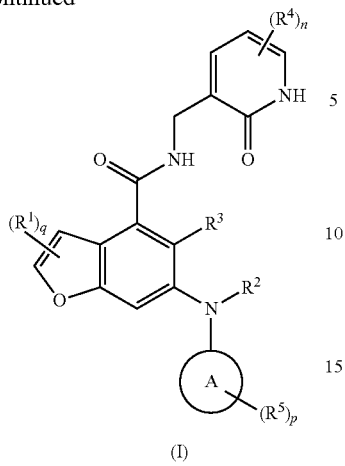
(I)
condensing a compound of formula (VI) with a compound of formula (VII) at room temperature to obtain the compound of formula (I);
wherein:
$R^1$ to $R^5$, ring A, p, q and n are as defined in claim 1.
* * * * *